United States Patent
Cho et al.

(10) Patent No.: US 10,051,425 B2
(45) Date of Patent: Aug. 14, 2018

(54) SMART TERMINAL SERVICE SYSTEM AND SMART TERMINAL PROCESSING DATA

(71) Applicant: LG ELECTRONICS INC., Seoul (KR)

(72) Inventors: Jinho Cho, Seoul (KR); Hokyung Ka, Seoul (KR); Jinseok Ko, Seoul (KR); Chul Park, Seoul (KR); Woong Jeong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/596,207

(22) Filed: May 16, 2017

(65) Prior Publication Data

US 2017/0339524 A1 Nov. 23, 2017

(30) Foreign Application Priority Data

May 18, 2016 (KR) .................. 10-2016-0060953

(51) Int. Cl.
*H04W 24/00* (2009.01)
*H04W 4/02* (2018.01)
(Continued)

(52) U.S. Cl.
CPC .......... *H04W 4/027* (2013.01); *A43B 3/0005* (2013.01); *A61B 5/1112* (2013.01);
(Continued)

(58) Field of Classification Search
CPC ....... H04W 4/027; H04W 4/008; G01S 19/25; H04M 1/72569; H04M 1/7253;
(Continued)

(56) References Cited

U.S. PATENT DOCUMENTS

2007/0123391 A1* 5/2007 Shin .................. A43B 3/0005
482/8
2012/0316843 A1* 12/2012 Beno ................. G06Q 10/0639
703/2
(Continued)

OTHER PUBLICATIONS

European Search Report dated Oct. 16, 2017 issued in Application No. 17171667.3.

*Primary Examiner* — Ajit Patel
(74) *Attorney, Agent, or Firm* — KED & Associates, LLP

(57) ABSTRACT

A smart terminal service system and a smart terminal processing data are disclosed. The smart terminal service system comprises smart shoes and the smart terminal. The smart shoes comprises a memory, a pressure sensor sensed by a predetermined pressure of a user, and a controller for calculating sensor velocity data on the basis of sensor data sensed by the pressure sensor and transmitting the calculated sensor velocity data to the smart terminal. And, the smart terminal comprises a communication unit for transmitting and receiving a signal to and from the smart shoes, a receiving unit for receiving GPS velocity data and sensor velocity data of the smart shoes, a memory, and a controller for controlling an execution of a smart shoes application and for calculating movement data of the smart shoes based on the received GPS velocity data and sensor velocity data which is sensed by the pressure sensor provided in the smart shoes.

10 Claims, 40 Drawing Sheets

(51) Int. Cl.
*A43B 3/00* (2006.01)
*A61B 5/11* (2006.01)
*A61B 5/00* (2006.01)
*G01S 19/25* (2010.01)
*H04L 29/08* (2006.01)
*H04M 1/725* (2006.01)
*G01C 21/16* (2006.01)
*G01S 19/49* (2010.01)
*H04W 4/80* (2018.01)

(52) U.S. Cl.
CPC .......... *A61B 5/1118* (2013.01); *A61B 5/6807* (2013.01); *G01C 21/165* (2013.01); *G01S 19/25* (2013.01); *G01S 19/49* (2013.01); *H04L 67/125* (2013.01); *H04M 1/7253* (2013.01); *H04M 1/72569* (2013.01); *H04W 4/80* (2018.02); *H04M 1/72572* (2013.01)

(58) Field of Classification Search
CPC ... A43B 3/0005; A61B 5/6807; A61B 5/1118; A61B 5/1112; H04L 67/125
See application file for complete search history.

(56) References Cited

U.S. PATENT DOCUMENTS

| | | | |
|---|---|---|---|
| 2013/0006528 A1 | 1/2013 | Napolitano | |
| 2013/0197857 A1 | 8/2013 | Lu et al. | |
| 2015/0022447 A1* | 1/2015 | Hare | G06F 3/017 345/158 |
| 2015/0151160 A1* | 6/2015 | Balakrishnan | G01P 13/00 700/91 |
| 2015/0257679 A1 | 9/2015 | Ross | |
| 2015/0285659 A1* | 10/2015 | Curtis | G01C 22/006 702/97 |
| 2015/0382321 A1* | 12/2015 | Ryu | H04W 68/02 455/458 |
| 2016/0016041 A1 | 1/2016 | Giedwoyn et al. | |
| 2016/0023043 A1* | 1/2016 | Grundy | A63B 24/0062 482/8 |
| 2016/0210838 A1* | 7/2016 | Yan | G08B 21/043 |
| 2016/0324445 A1* | 11/2016 | Kim | A61B 5/112 |
| 2016/0366266 A1* | 12/2016 | Chung | H04B 1/385 |
| 2017/0155978 A1* | 6/2017 | Noh | A43B 3/0005 |
| 2017/0227375 A1* | 8/2017 | Parikh | G01C 22/006 |
| 2017/0277138 A1* | 9/2017 | Kaji | G04G 21/025 |
| 2017/0300598 A1* | 10/2017 | Akavia | G06F 17/50 |
| 2017/0308663 A1* | 10/2017 | Moya | G06F 19/3406 |

* cited by examiner

FIG. 7
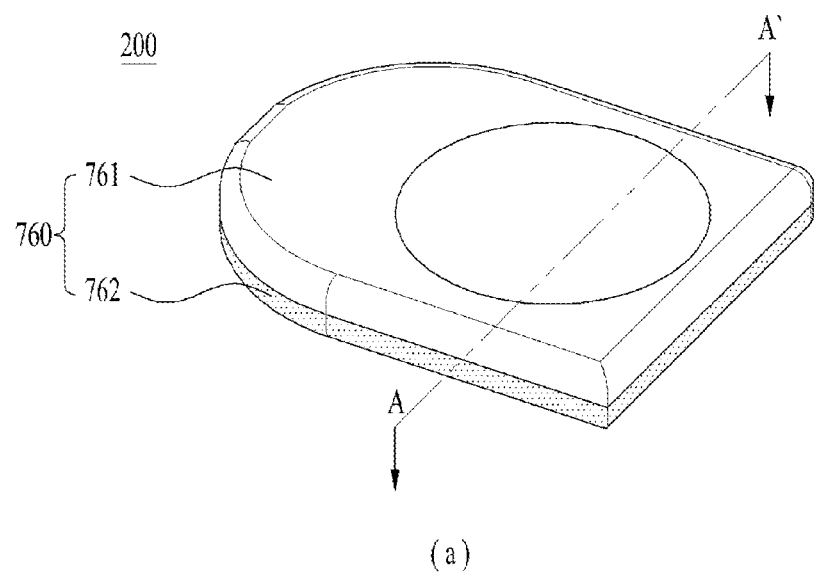
(a)
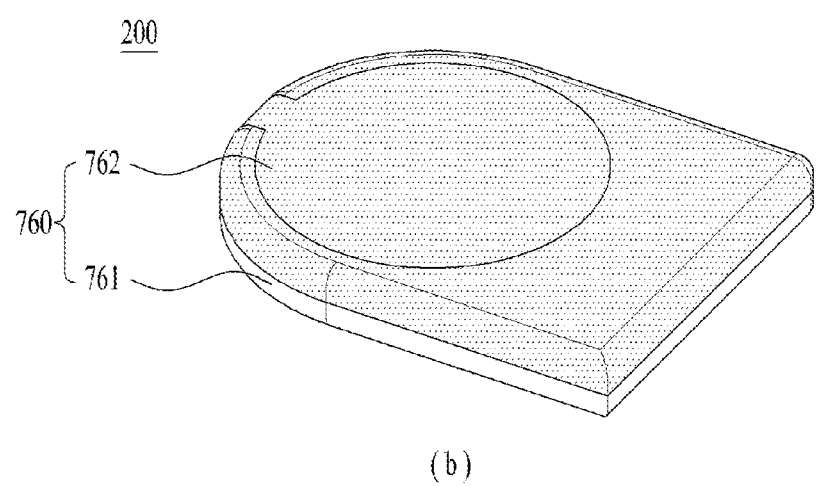
(b)

| | | left smart shoe | right smart shoe |
|---|---|---|---|
| measurement | pressure sensor | 0.9 | 1.1 |
| | motion sensor | 0.8 | 1.2 |

| | calibration algorithm |
|---|---|
| left smart shoe value A measured by pressure sensor | A * 0.8/0.9 |
| left smart shoe value B measured by pressure sensor | B * 1.2/1.1 |

FIG. 24
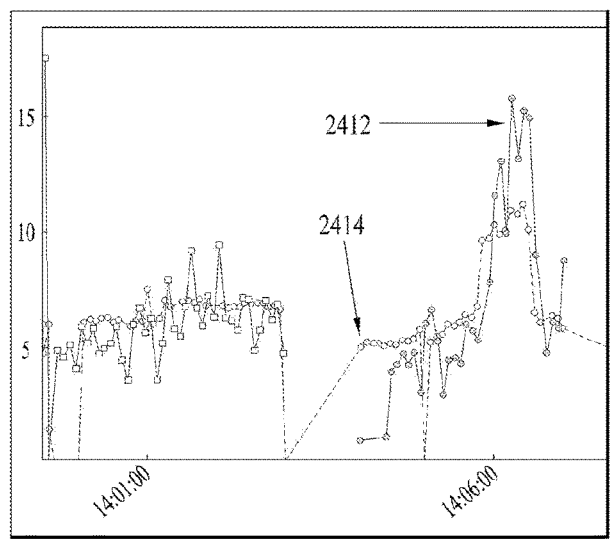
(a)
(c)
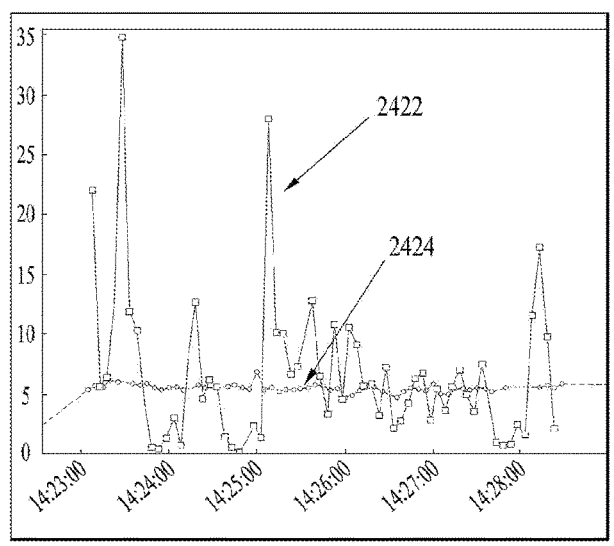
(b)

FIG. 25

(a) $\text{filtered} = \underbrace{\left(\dfrac{W_{gps}}{W_{sensor} + W_{gps}}\right)}_{2510} \text{Velocity}_{sensor} + \underbrace{\left(\dfrac{W_{sensor}}{W_{sensor} + W_{gps}}\right)}_{2520} \text{Velocity}_{gps}$ (b) $w_{gps} = |\text{Velocity Deviation}_{gps}| \times p1^{(gps_{accuracy} \cdot p2)}$ (c) $w_{sensor} = |\text{Velocity Deviation}_{sensor}|$

SMART TERMINAL SERVICE SYSTEM AND SMART TERMINAL PROCESSING DATA

CROSS-REFERENCE TO RELATED APPLICATIONS

Pursuant to 35 U.S.C. § 119(a), this application claims the benefit of earlier filing date and right of priority to Korean Application No. 10-2016-0060953, filed on May 18, 2016, the contents of which are hereby incorporated by reference herein in their entirety.

BACKGROUND OF THE INVENTION

Field of the Invention

The present invention relates to a smart terminal service system and a smart terminal processing data.

Discussion of the Related Art

A mobile terminal has been implemented as a multimedia player having diverse functions in addition to a simple communication function of the related art. A main example of the mobile terminal may include a smart phone. In addition, the mobile terminal has been upgraded or developed to a user wearable type, for example, a wearable device. In this case, the wearable device includes products such as clothes and shoes, which are worn by a user, as well as products such as a smart watch, smart glasses, a head mounted display (HMD).

Meanwhile, the mobile terminal leads implementation of IoT (Internet of Things) through data communication with various things together with or separately from a conventional stationary terminal.

In this way, various attempts for fulfilling needs of users or improving convenience through data communication between terminals have been recently made in a digital environment. However, active services have not been provided yet due to incomplete related specification or system for data communication between terminals. For example, a user who wears smart shoes may use GPS (Global Positioning System) data for external activity. In this case, if reception of GPS data is good, the corresponding data may be reliable but it is difficult to rely on the corresponding data if not so. In other words, since the GPS data may frequently be changed depending on position, environment, etc., and may also have many errors, it is likely to generate an error when movement data for external activity of a user who wears smart shoes are processed by the GPS data only, whereby inexact data may be provided. This could lead to dissatisfaction of the user.

SUMMARY OF THE INVENTION

Accordingly, the present invention is to address the above-noted and other problems.

An object of the present invention is to exactly calculate movement data for activity of a user who wears smart shoes.

Another object of the present invention is to calculate exact movement data even in various statuses by performing filtering using sensing data through a pressure sensor provided in smart shoes in spite of an error of GPS data for external activity of a user who wears the smart shoes.

Still another object of the present invention is to improve satisfaction of a user who wears smart shoes as movement data of the user is exactly calculated and provided.

The technical objects that can be achieved through the present invention are not limited to what has been particularly described hereinabove and other technical objects not described herein will be more clearly understood by persons skilled in the art from the following detailed description.

This specification discloses a smart terminal service system and a smart terminal processing data according to the present invention.

To achieve these objects and other advantages and in accordance with the purpose of the specification, as embodied and broadly described herein, a smart terminal for performing data communication with smart shoes according to one embodiment of the present invention may include a communication unit for transmitting and receiving a signal to and from the smart shoes; a receiving unit for receiving GPS velocity data and sensor velocity data of the smart shoes; a memory; and a controller for controlling an execution of a smart shoes application and calculating movement data of the smart shoes based on the received GPS velocity data and sensor velocity data which is sensed by a pressure sensor provided in the smart shoes.

In another aspect of the present invention, a smart terminal service system comprises smart shoes and a smart terminal. The smart shoes may comprise a memory; a pressure sensor sensed by an inputted pressure for a reference of the smart shoes; and a controller for calculating sensor velocity data on the basis of sensor data sensed by the pressure sensor and transmitting the calculated sensor velocity data to the smart terminal. And, the smart terminal may comprise a communication unit for transmitting and receiving a signal to and from the smart shoes; a receiving unit for receiving GPS velocity data and sensor velocity data of the smart shoes; a memory; and a controller for controlling an execution of a smart shoes application and calculating movement data of the smart shoes based on the received GPS velocity data and sensor velocity data which is sensed by the pressure sensor provided in the smart shoes.

In other aspect of the present invention, smart shoes for performing data communication with a smart terminal may comprise a communication unit for transmitting and receiving a signal to and from the smart terminal; a GPS receiving unit for receiving GPS velocity data; a pressure sensor unit for sensing sensor velocity data; a memory; and a controller for controlling the GPS receiving unit and the pressure sensor unit to compress and store the GPS velocity data and the sensor velocity data in the memory, calculate or calibrate movement data of the smart shoes on the basis of the stored GPS velocity data and sensor velocity data, and transmit the calculated or calibrated movement data of the smart shoes to the smart terminal.

In other aspect of the present invention, a method of performing data in a smart terminal communicated with smart shoes, the method may include transmitting and receiving a signal to and from the smart shoes; receiving GPS velocity data and sensor velocity data of the smart shoes; executing a smart shoes application; and calculating movement data of the smart shoes based on the received GPS velocity data and sensor velocity data which is sensed by a pressure sensor included in the smart shoes.

In other aspect of the present invention, a method of processing data in a smart terminal service system including smart shoes and a smart terminal, the method may include sensing an inputted pressure for a reference of the smart shoes; calculating sensor velocity data based on the sensed predetermined pressure of the user; transmitting the calculated sensor velocity data to the smart terminal; transmitting and receiving a signal to and from the smart shoes; receiving GPS (Global Positioning System) velocity data and sensor velocity data of the smart shoes; executing a smart shoes application; and calculating movement data of the smart shoes based on the received GPS velocity data and sensor velocity data which is sensed by a pressure sensor included in the smart shoes.

In other aspect of the present invention, a method of processing data in smart shoes communicated with a smart terminal, the method may include transmitting and receiving a signal to and from the smart terminal; receiving GPS velocity data; sensing sensor velocity data; compressing and storing the GPS velocity data and the sensor velocity data; calculating or calibrating movement data of the smart shoes based on the stored GPS velocity data and sensor velocity data; and transmitting the calculated or calibrated movement data of the smart shoes to the smart terminal.

The above technical solutions are merely some parts of the embodiments of the present invention and various embodiments into which the technical features of the present invention are incorporated can be derived and understood by persons skilled in the art from the following detailed description of the present invention.

According to the present invention, the following advantageous effects can be obtained.

According to at least one of the embodiments of the present invention, movement data for activity of a user who wears smart shoes can be calculated exactly.

According to at least one of the embodiments of the present invention, exact movement data can be calculated even in various statuses by performing filtering using sensing data through a pressure sensor provided in smart shoes in spite of an error of GPS data for external activity behavior of a user who wears the smart shoes.

According to at least one of the embodiments of the present invention, satisfaction of a user who wears smart shoes can be improved as movement data of the user is exactly calculated and provided.

The effects that can be achieved through the present invention are not limited to what has been particularly described hereinabove and other effects not described herein will be more clearly understood by persons skilled in the art from the following detailed description.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 7 is a view illustrating an example of an external appearance of a smart shoes sensor module 200 including a circuit configuration of FIG. 6;

FIG. 24 is a GPS data graph according to the present invention;

FIG. 25 illustrates filtering technique for GPS velocity calibration in accordance with one embodiment of the present invention;

DETAILED DESCRIPTION OF THE PREFERRED EMBODIMENTS

Figure 1:
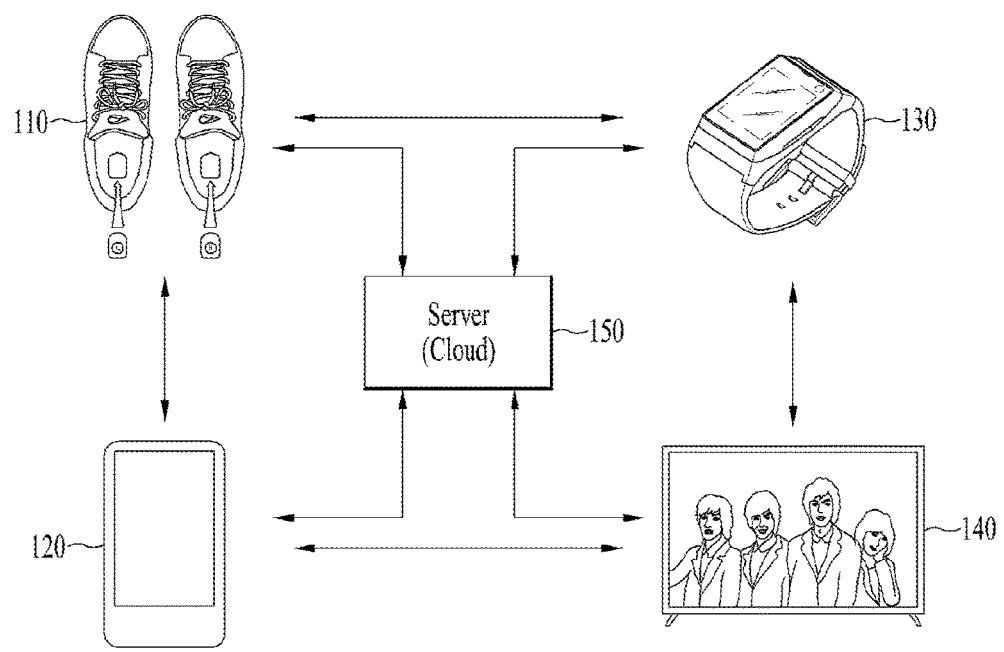
FIG. 1 is a view briefly illustrating a smart terminal service system that includes smart shoes according to one embodiment of the present invention.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated.

The suffixes "module" and "unit" for the elements used in the following description are given or used in common by considering facilitation in writing this disclosure only but fail to have meanings or roles discriminated from each other.

Also, in description of the embodiments disclosed in this specification, if detailed description of the disclosure known in respect of the present invention is determined to make the subject matter of the embodiments disclosed in this specification obscure, the detailed description will be omitted. Also, the accompanying drawings are only intended to facilitate understanding of the embodiments disclosed in this specification, and it is to be understood that technical spirits disclosed in this specification are not limited by the accompanying drawings and the accompanying drawings include all modifications, equivalents or replacements included in technical spirits and technical scope of the present invention.

A mobile terminal has been enlarged to a type for performing various functions in association with various things including a smart phone that performs production and consuming functions of contents in addition to a communication function. Examples of the mobile terminal may include an object that may be worn by a user, that is, a wearable device such as a smart watch, smart glasses, a head mounted display (HMD), an eye mounted display (EMD), clothes, and shoes.

Hereinafter, in this specification, for understanding of the present invention and convenience of description, a wearable device will be described based on shoes, especially smart shoes. The smart shoes may provide various kinds of information such as the result of analysis for information on activity or movement of a wearer and recommended information related to the analysis result and a feedback for the information through a mobile terminal such as a smart phone and a smart watch. In this case, the smart shoes may perform sensing, tracing, analyzing, recording, and proposal functions of information on movement of a user who wears the smart shoes, for example, activity time, activity distance, and activity track. The information on movement of the wearer may be sensed using a motion sensor. Examples of the motion sensor may include a global positioning system (GPS), an acceleration sensor, and a gyro sensor.

A smart terminal for performing data communication with smart shoes according to one embodiment of the present invention may include: a communication unit transmits and receives a signal to and from the smart shoes, a receiving unit receives GPS velocity data and sensor velocity data from the smart shoes, a memory, and a controller controls an execution of a smart shoes application and calculates movement data of the smart shoes or a user who wears the smart shoes based on the received GPS velocity data and sensor velocity data which is sensed by a pressure sensor provided in the smart shoes.

A smart terminal service system according to one embodiment of the present invention may include smart shoes and a smart terminal. The smart shoes may include a memory, a pressure sensor sensing sensor data sensed by an inputted pressure for a reference of the smart shoes (or a user), and a controller calculating sensor velocity data based on the sensor data sensed by the pressure sensor and transmitting the sensor velocity data to the smart terminal. And, the smart terminal may include a communication unit transmitting and receiving a signal to and from the smart shoes, a receiving unit receiving GPS velocity data and sensor velocity data from the smart shoes, a memory, and a controller controlling an execution of a smart shoes application and calculating movement data of the smart shoes based on the received GPS velocity data and sensor velocity data sensed by the pressure sensor provided in the smart shoes.

In accordance with one embodiment of the present invention, the smart shoes for performing a data communication with the smart terminal may include: a communication unit transmits and receives a signal to and from the smart terminal, a GPS receiving unit receives GPS velocity data, a pressure sensor unit senses sensor velocity data, a memory, and a controller controls the memory to compress and stores the GPS velocity data received from the GPS receiving unit and the sensor velocity data sensed by the pressure sensor, calculates, calibrates or corrects movement data of the smart shoes on the basis of the stored GPS velocity data and sensor velocity data, and transmits the calculated, calibrated or corrected movement data of the smart shoes to the smart terminal.

FIG. 1 is a view briefly illustrating a smart terminal service system that includes smart shoes according to one embodiment of the present invention.

Referring to FIG. 1, the smart terminal service system includes smarts shoes 110, a server 150, and one or more mobile terminals. At this time, the server 150 may not be required necessarily depending on a system.

The smart shoes 110 are implemented as a pair that includes one (hereinafter, 'left (L) smart shoe') of shoes for a left foot and one (hereinafter, 'right (R) smart shoe') of shoes for a right foot. At this time, a sensor module for smart shoes related to the present invention may be included in at least one of the left (L) smart shoe and the right (R) smart shoe. However, in this specification, for understanding of the present invention and convenience of description, the case that the sensor module for the smart shoes is included in both the left (L) smart shoe and the right (R) smart shoe will be described exemplarily.

The smart shoes 110 senses movement of a user, that is, a wearer who wears the smart shoes, and transmits movement information of the sensed user to one or more mobile terminals directly or indirectly through the server 150. In this case, a smart phone 120, a smart watch 130, etc. may be included in one or more mobile terminals. Also, the smart shoes 110 may also transmit the movement information to a digital TV 140, a digital signage (not shown), etc. However, it will be apparent that the smart shoes 110 may perform data communication with various devices in addition to the aforementioned terminals or shown device.

Meanwhile, the smart shoes 110 may perform data communication with terminals located at a short distance by using a short-range communication protocol or perform data communication with terminals located at a long distance by using the server 150. Alternatively, regardless of the distance, the smart shoes 110 may upload movement information of the user on the server 150 such as a cloud or conveniently download the movement information through the terminal at a desired place at any time.

In addition, the smart shoes 110 may perform data communication with at least two or more terminals simultaneously or sequentially.

Figure 2:
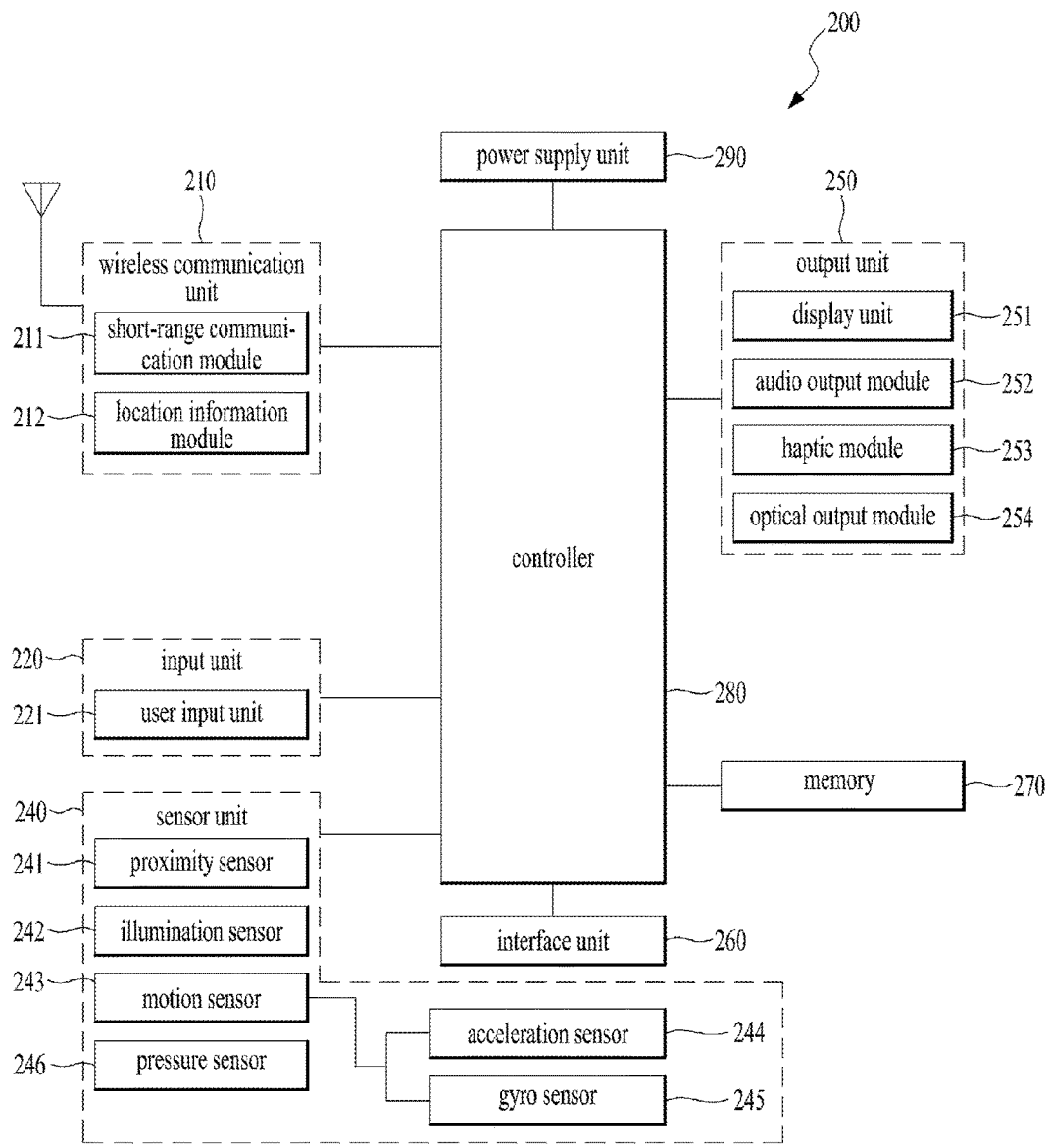
FIG. 2 is a block diagram illustrating a smart shoes sensor module 200 according to one embodiment of the present invention.

FIG. 2 is a block diagram illustrating a smart shoes sensor module 200 according to one embodiment of the present invention. In this case, a configuration of the smart shoes sensor module 200 will be described in FIG. 2 but its configuration may be regarded as a configuration of the mobile terminal. At this time, some components of the smart shoes sensor module 200 may be different from those shown.

The smart shoes sensor module 200 may include a wireless communication unit 210, an input unit 220, a sensor unit 240, an output unit 250, an interface unit 260, a memory 270, a controller 280, and a power supply unit 290. The components shown in FIG. 2 are not required necessarily for implementation of the smart shoes sensor module 200. The smart shoes sensor module 200 described in this specification may have components more than or smaller than the components listed above.

In more detail, the wireless communication unit 210 of the aforementioned components may include one or more modules that enable wireless communication between the smart shoes sensor module 200 and a wireless communication system, between the smart shoes sensor module 200 and another mobile terminal, or between the smart shoes sensor module 200 and an external server. Also, the wireless communication unit 210 may include one or more modules that connect the smart shoes sensor module 200 to one or more networks.

The wireless communication unit 210 may include at least one of a short-range communication module 211 and a location information module 212.

The short-range communication module 211 may be connected with the smart shoes module 200 through a Bluetooth mode and transmit and receive data to and from the smart shoes module 200.

The location information module 211 serves to measure or transmit location information of the smart shoes module 200, and may include a concept redundant with a motion sensor 243 which will be described later.

The input unit 220 may include a user input unit 221 (for example, touch key, push key (mechanical key), etc.) for receiving information from a user. Audio data or image data collected by the input unit 220 may be analyzed and processed as a control command of a user. The input unit 220 may serve to input an on/off function for enabling or disabling a function of the smart shoes module 200, or may be omitted for saving of the production cost or lightweight if necessary.

The sensor unit 240 may include one or more sensors for sensing at least one of information in the smart shoes module 20, peripheral environment information surrounding the smart shoes module 200 and user information. For example, the sensor unit 240 may include at least one of a proximity sensor 241, an illumination sensor 242, a touch sensor, an acceleration sensor 244, a magnetic sensor, a gravity sensor (G-sensor), a gyroscope sensor 245 (hereinafter, 'gyro sensor'), a motion sensor 243, an RGB sensor, an infrared (IR) sensor, a finger scan sensor, an ultrasonic sensor, an optical sensor, a battery gauge, an environment sensor (for example, a barometer, a hygrometer, a thermometer, a radiation detection sensor, a thermal sensor, and a gas sensor), and a chemical sensor (for example, an electronic nose, a health care sensor, a biometric sensor, and the like). Meanwhile, the smart shoes module 200 disclosed in this specification may be configured to utilize information obtained from one or more sensors of the sensor unit 240 and combinations thereof.

Particularly, the acceleration sensor 244 and the gyro sensor 345, which are mentioned in the present invention, may be included in the motion sensor 243.

The motion sensor 243 packaged in the smart shoes sensor module 200 may mean a component for directly sensing movement of the smart shoes sensor module 200. The motion sensor 243 may include the acceleration sensor 244 and the gyro sensor 245. If necessary, the motion sensor 243 may include any one of the acceleration sensor 244 and the gyro sensor 245.

Movement such as location change relative to two-dimensional or three-dimensional location and time of the smart shoes sensor module 200 may be sensed through the motion sensor 243.

The motion sensor 243 and the controller 280 may be included in the smart shoes sensor module 200 or may be packaged in the smart shoes 110 as a separate component.

The pressure sensor 246 is packaged in the smart shoes sensor module 200 and senses a pressure. The pressure sensor 246 may functionally be included in the motion sensor 243. In the present invention, the motion sensor 243 includes the acceleration sensor 244 and the gyro sensor 245, and the pressure sensor 246 will be described as a separate component independent from the motion sensor 243.

The output unit 250 is configured to output various types of information, such as audio, video, tactile output, and the like. The output unit 250 may include at least one of a display unit 251, an audio output module 252, a haptic module 253, and an optical output module 24.

The interface unit 260 serves as an interface with various types of external devices that can be coupled to the smart shoes sensor module 200. The interface unit 260, for example, may include at least one of external power supply ports, wired or wireless data ports, memory card ports, and ports for connecting a device having an identification module. The smart shoes sensor module 200 may perform assorted control functions associated with a connected external device, in response to the external device being connected to the interface unit 260.

Also, the memory 270 is implemented to store data to support various functions or features of the smart shoes sensor module 200. The memory 270 may be configured to store data or instructions for operations of the controller driven in the smart shoes sensor module 200.

The controller 280 typically functions to control an overall operation of the smart shoes sensor module 200, in addition to the operations associated with an application. The controller 280 may process signals, data, information and the like inputted or outputted through the above-mentioned components and/or runs the data or instructions stored in the memory 170, thereby processing or providing a user with appropriate information and/or functions.

The power supply unit 290 can be configured to receive external power or provide internal power in order to supply appropriate power required for operating elements and components included in the smart shoes sensor module 200. The power supply unit 290 may include a battery, and the battery may be configured to be embedded in the smart shoes sensor module, or configured to be detachable from the smart shoes sensor module.

At least one portion of the respective components mentioned in the foregoing description can cooperatively operate to embody operations, controls or controlling methods of the smart shoes sensor module 200 according to various embodiments of the present invention mentioned in the following description. Moreover, the operations, controls or controlling methods of the smart shoes sensor module 200 can be embodied in the smart shoes sensor module 200 by running at least one or more data or instructions stored in the memory 170.

Figure 3:
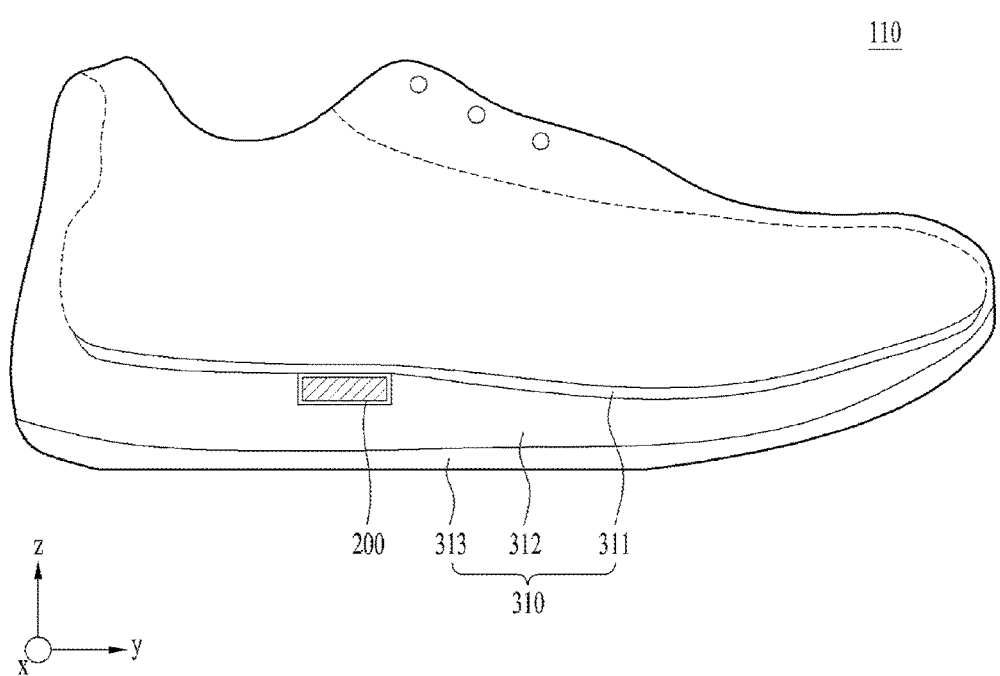
FIG. 3 is a cross-sectional view of a y-z plane of smart shoes 110 provided with a smart shoes sensor module 200 according to one embodiment of the present invention.

FIG. 3 is a cross-sectional view of a y-z plane of smart shoes 110 provided with a smart shoes sensor module 200 according to one embodiment of the present invention.

A sole frame 310 of the smart shoes 110 means a direct/indirect area in which the soles of the wearer are in contact. In other words, the sole frame 310 may mean a frame of an area provided between a foot and sole of the wearer in the smart shoes sensor module 200. The sole frame 310 may include an insole 311 in which the sole of the wearer is directly in contact, an outsole 313 provided on the lowest end of the smart shoes sensor module 200, being directly in contact with the outside, that is, ground, and a midsole 312 provided between the insole 311 and the outsole 313, forming a certain volume.

The insole 311 may be a shoe insert which is commonly mentioned, but may be configured in a single body with the midsole 312 without distinction of the insole 311 and the midsole 312, if necessary, or may be provided in a coupled type with the midsole 312 by an adhesive although provided as a separate member.

The smart shoes sensor module 200 may be provided on the sole frame 310. The smart shoes sensor module 200 may process the sole frame 310 as signal or data in accordance with a pressure applied by walking or driving of the wearer.

Figure 4:
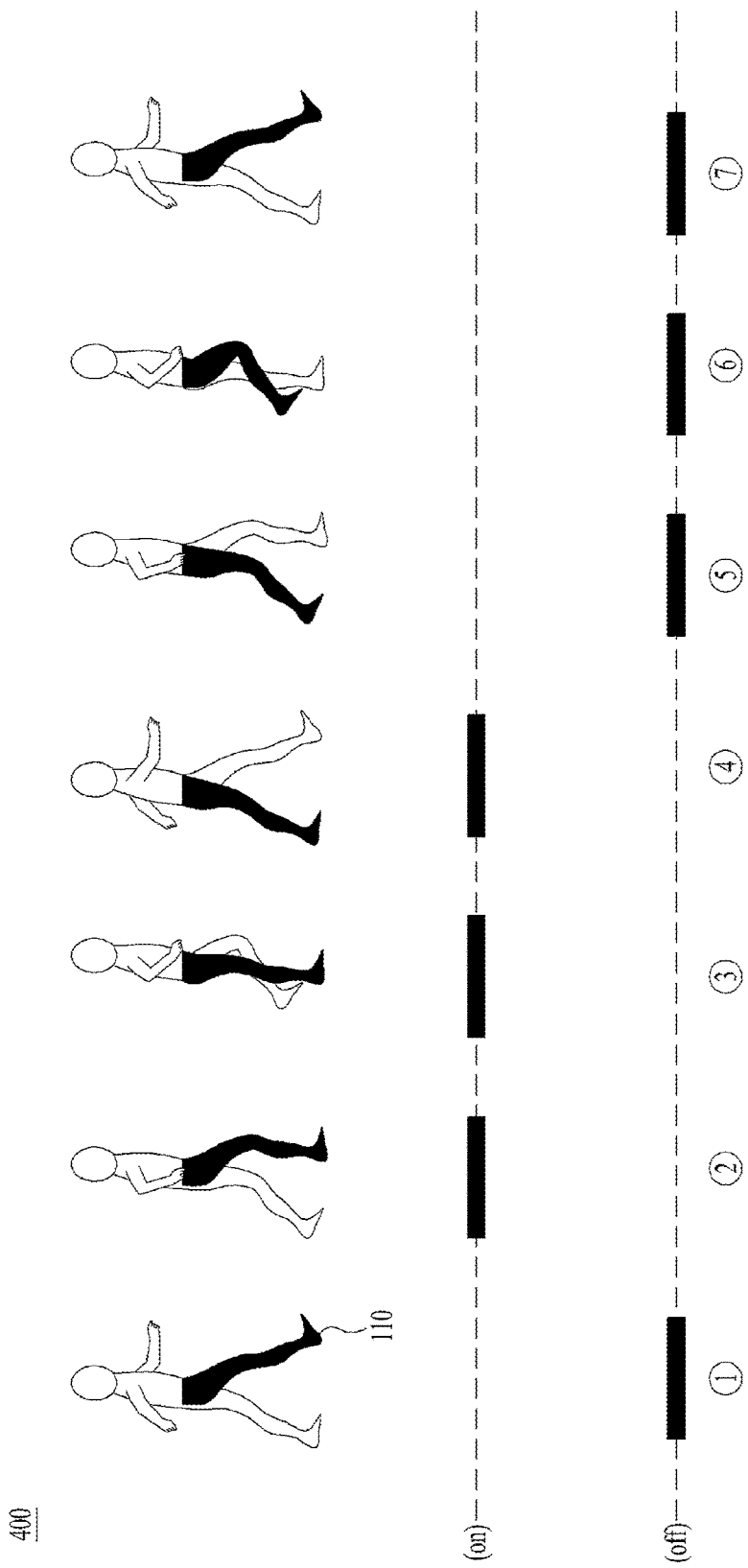
FIG. 4 is a view illustrating time sequential correspondence to walking of a smart shoes wearer 400 provided with a smart shoes sensor module 200 according to one embodiment of the present invention and a signal generated in accordance with walking.

FIG. 4 is a view illustrating time sequential correspondence to walking of smart shoes wearer 400 provided with a smart shoes sensor module 200 according to one embodiment of the present invention and a signal generated in accordance with walking.

An on signal '1' may be generated in the smart shoes sensor module 200 when the wearer 400 who wears the smart shoes 110 steps on the ground, whereas an off signal '0' may be generated in the smart shoes sensor module 200 when the wearer 400 does not step on the ground.

A value of '1', that is, the on signal may be generated in the smart shoes sensor module 200 as a pressure value of a specific value or more acts on states ② to ④ of FIG. 4, and a value of '0', that is, the off signal may be generated in the smart shoes sensor module 200 as a pressure value less than a specific value acts on the other states ① and ⑤-⑦.

The on signal generated in the smart shoes sensor module 200 may be generated by a predetermined threshold pressure value.

The predetermined threshold pressure value may be determined in accordance with material rigidity and elasticity of the smart shoes sensor module 200, a size of the smart shoes sensor module 200, or an interval between a conductive member and a first circuit.

For example, if the predetermined threshold pressure value is more increased, a pressure threshold value that may generate the on signal is more increased. Therefore, the value of '1', that is, the on signal may be generated in the smart shoes sensor module 200 in case of the states ② and ③, and the value of '0', that is, the off signal may be generated in the smart shoes sensor module 200 in case of the other states ① and ④-⑦.

Therefore, through this result, start and end of one step of the wearer may be determined, and if the step is repeated, a cycle of each step may be identified.

Referring to FIG. 4, ② may be construed as a start of one step and a point of ① after passing through ⑦ may be construed as an end of one step.

Also, if a change from ② to ① is repeated, a plurality of steps may be construed by identifying one cycle as one step.

In the case that a unit of a step is construed using the acceleration sensor 244 (see FIG. 2) and/or the gyro sensor 245 (see FIG. 2) of the motion sensor 243 (see FIG. 2), an error may occur due to various factors, that is, noise in case of a point where a velocity value of the smart shoes sensor module 200 is '0'. However, in the present invention, the noise may be removed through the on/off signal based on the pressure sensor in the smart shoes sensor module 200, whereby an exact step unit may be identified.

The smart shoes sensor module 200 may be operated depending on whether a pressure acts on a direction toward the sole frame 310 (see FIG. 3) from the sole of a foot, that is, a lower direction. However, the lower direction is not required necessarily, and the smart shoes sensor module 200 may be operated based on a pressure for a direction dislocated at a certain angle with respect to the lower direction if necessary. If a plurality of smart shoes sensor modules 200 are provided, they may be operated with respect to various directions.

The direction of the pressure may be based on a normal step and power action of the wearer, or may be varied depending on a step and power action of another wearer.

The predetermined threshold pressure value may be applied differently depending on physical habitual factors of the wearer, such as height, weight, foot size, sex, and age. However, since on/off of the smart shoes sensor module 200 may depend on material and structure, the smart shoes sensor module 200 of which material and structure are determined may have a predetermined threshold pressure value. This threshold pressure value may be changed randomly considering sensing data exactness for the wearer, noise, etc.

Figure 5:
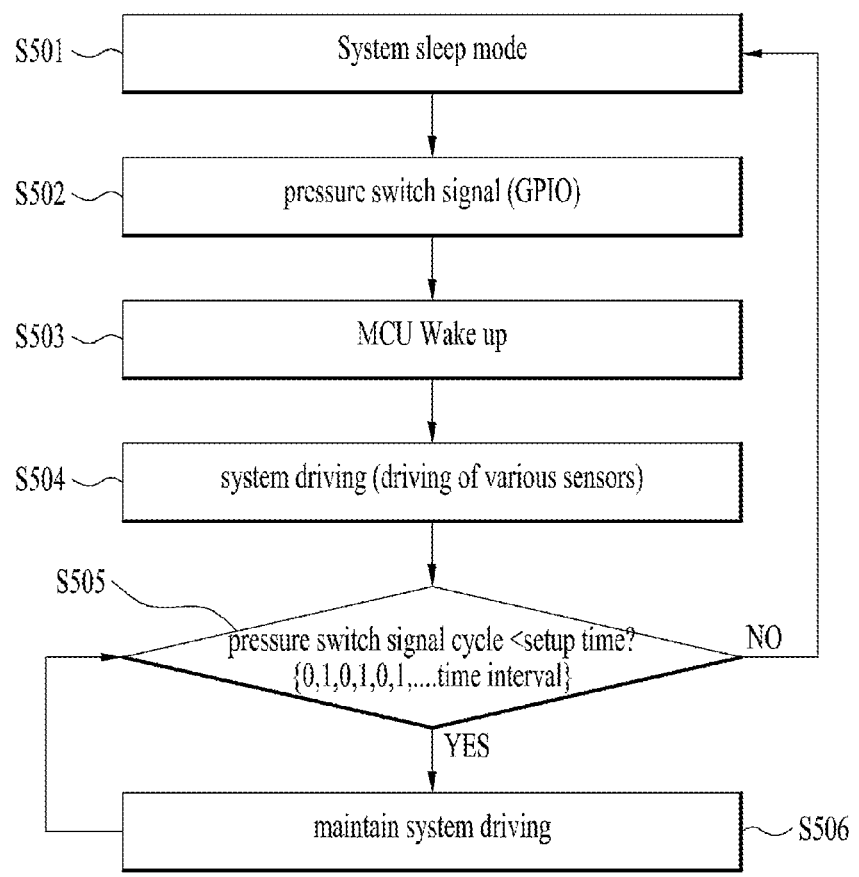
FIG. 5 is a flow chart illustrating an operation of a smart shoes sensor module 200 according to one embodiment of the present invention.

FIG. 5 is a flow chart illustrating an operation of a smart shoes sensor module 200 according to one embodiment of the present invention.

The controller 280 may perform current supply and control of the motion sensor 243 on the basis of the on or off signal of the smart shoes sensor module 200.

If the off signal of the smart shoes sensor module 200 is continuously generated for a certain time or more, it may be construed that the user has not worn the smart shoes 110 or does not move even though the user has worn the smart shoes 110. Alternatively, it may be construed that the user has not performed movement that generates the predetermined threshold pressure or more even though the user has worn the smart shoes 110. For example, this case may include a case that the user who wears the smart shoes 110 sits on a chair and moves slightly even though the user steps on the ground or not.

Therefore, the controller 280 may perform a system sleep mode for minimizing a power consumed for the smart shoes sensor module 200 by disabling the motion sensor 243 (S501).

If the on signal is generated in the smart shoes sensor module 200 during the system sleep mode, it may be construed that the user performs activity while wearing the smart shoes 110 (S502).

Therefore, the one signal of the smart shoes sensor module 200, which is generated during the system sleep mode, may enable the controller 280 (S503). If the controller 280 is already enabled, this step may be omitted.

The controller 280 may release the system sleep mode of the smart shoes sensor module 200 and drive the system (S504). In this case, driving of the system may mean that various electronic parts, circuits and sensors provided in the smart shoes sensor module 200 are turned on.

The controller 280 compares a time interval of occurrence of the on and off signals of the smart shoes sensor module 200 with a predetermined time interval in real time (S505).

If the time interval of occurrence of the on and off signals of the smart shoes sensor module 200 is within the predetermined time interval, that is, if the value of 1 of the on signal is received within a predetermined time, system driving of the smart shoes sensor module 200 may be maintained (S506).

On the other hand, if the time interval of occurrence of the on and off signals of the smart shoes sensor module 200 exceeds the predetermined time interval, that is, if the value of '0' of the off signal is received continuously for a predetermined time or more, the controller 280 may disable the overall system of the smart shoes sensor module 200. That is, the controller 280 may switch system driving to the system sleep mode. In this case, the controller 280 may perform current breaking and deactivation for the motion sensor 243.

Figure 6:
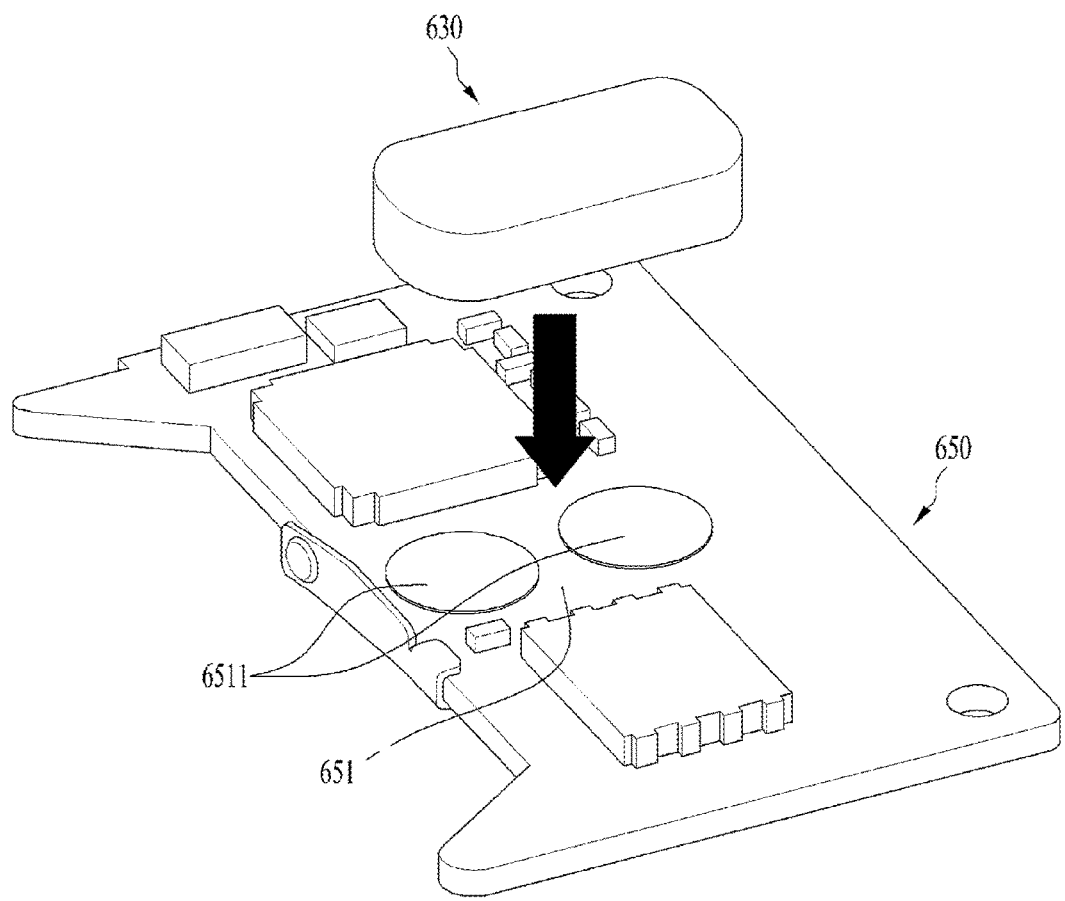
FIG. 6 is a view illustrating a system or circuit configuration of a smart shoes sensor module 200 according to one embodiment of the present invention.

FIG. 6 is a view illustrating a system or circuit configuration of a smart shoes sensor module 200 according to one embodiment of the present invention.

A pressure conductive member 630 according to the present invention, which is one of core components of the smart shoes sensor module 200 may be operated in association with a first circuit 651. The first circuit 651 may be packaged on a substrate 650 and then at least one area of the first circuit 651 may be exposed on the substrate 650.

In this case, for convenience, FIG. 6 illustrates a state before coupling between the conductive member 630 and the first circuit 651, wherein the conductive member 630 may be fixed to the substrate 650 by being spaced apart from the substrate 650 by another member, or may be fixed to the substrate 650 in contact with the substrate 650.

If a pressure less than a threshold value acts on the smart shoes sensor module 200, the conductive member 630 is electrically detached from the first circuit 651.

The first circuit 651 may maintain an open circuit, that is, an electrically open state until the first circuit 651 is connected to the conductive member 630.

If a pressure more than a threshold value acts on the smart shoes sensor module 200, the conductive member 630 may electrically be connected with contact terminals 6511 of the first circuit 651.

The two contact terminals 6511 which are spaced apart from each other may electrically be connected with each other by the conductive member 630, whereby the first circuit 651 may maintain a closed circuit. If the first circuit 651 configures a closed circuit, an electric signal may be generated.

The controller 280 may recognize the electric signal generated in the first circuit 651 as the aforementioned on/off signal of FIG. 5, and may control various operations on the basis of the recognized on/off signal.

Since the controller 280 recognizes the electric signal generated as the on/off signal, although the recognized operation may be construed as a separate independent procedure, it may be construed as one operation performed by one circuit.

Meanwhile, as one embodiment, although two contact terminals 6511 related to electric connection and connection release between the pressure conductive member 630 and the first circuit 651 are shown in FIG. 6, the present invention is not limited to the example of FIG. 6. For example, at least one or more contact terminals 6511 may be provided. Also, although not shown, electric connection and connection release between the pressure conductive member 630 and the first circuit 651 may be implemented in a non-contact mode instead of a contact mode based on the contact terminals 6511.

FIG. 7 is a view illustrating an example of an external appearance of a smart shoes sensor module 200 including a circuit configuration of FIG. 6.

FIG. 7*a* is a front perspective view illustrating an external appearance of the smart shoes sensor module 200, and FIG. 7*b* is a rear perspective view illustrating an external appearance of the smart shoes sensor module 200.

A housing 760 constituting the external appearance of the smart shoes sensor module 200 may include an upper case 761 and a lower case 762. Although the upper case 761 and the lower case 762 may be formed in a uni-body type. 300, the upper case 761 and the lower case 762 may be formed respectively in a separate body and then coupled to each other in the present invention.

Also, in this specification, although the smart shoes sensor module 200 is formed by coupling between two cases, that is, the upper case 761 and the lower case 762, the present invention is not limited to this case, and the smart shoes sensor module 200 may be formed by coupling between two or more cases as the case may be.

Figure 8:
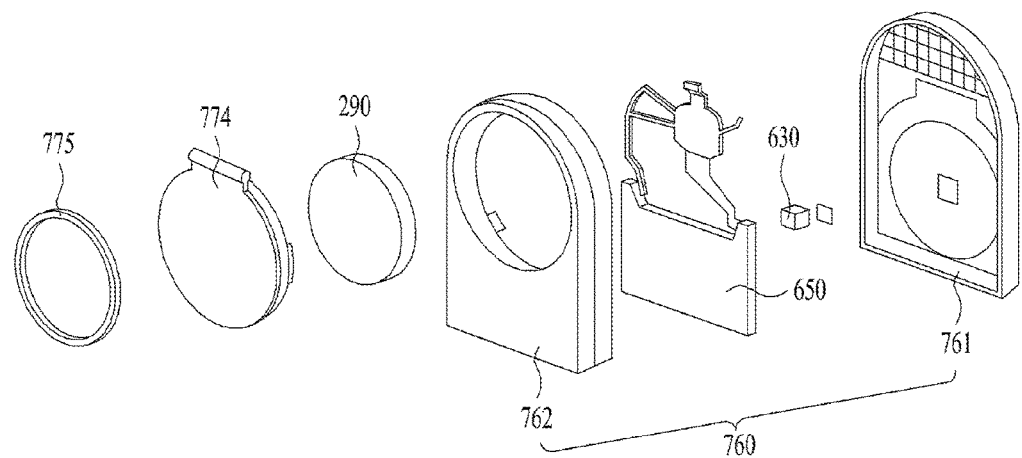
FIG. 8 is a view illustrating an individual configuration of a smart shoes sensor module 200 according to one embodiment of the present invention.

FIG. 8 is a view illustrating an individual configuration of a smart shoes sensor module 200 according to one embodiment of the present invention.

The smart shoes sensor module 200 may mean a structural unit for packaging components that perform functions of the pressure sensor 246 (see FIG. 2), and may physically include all the components packaged in the housing 760.

The housing 760 may package the components such as the substrate 650. The housing 760 may be configured by coupling between the upper case 761 and the lower case 762, which are provided on a front surface thereof.

The power supply unit 290 may be packaged in the housing 760 to serve to supply a power to the controller 280, etc. For active exchange of the power supply unit 290, the power supply unit 290 may include a battery cover 774 coupled to the lower case 762. A gap between the battery cover 774 and the lower case 762 may be stopped by a waterproof ring 775, whereby no problem may occur in waterproof.

Figure 9:
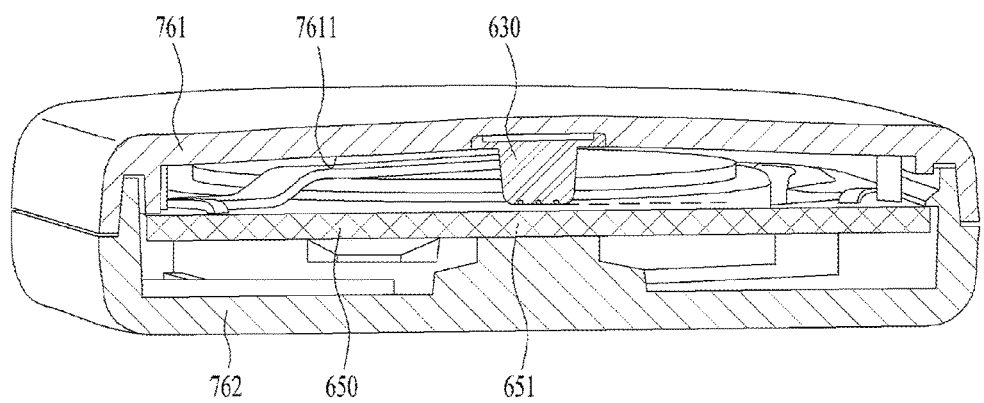
FIG. 9 is a cross-sectional view taken along line A-A' of FIG. 7.

FIG. 9 is a cross-sectional view taken along line A-A' of FIG. 7.

The upper case 761 may form an upper appearance of the smart shoes sensor module 200, and may elastically move by means of a pressure of a threshold value or more which acts on a first direction. The first direction may mean a ground direction from feet of the wearer. In other words, the first direction may mean a direction from the upper case 761 to the lower case 762.

The upper case 761 may be formed in a thin plane shape to transfer a pressure from the sole of the wearer to the conductive member 630, and may be provided to directly adjoin the conductive member 630. An outer surface of the upper case 761 is formed to be convex, whereby a pressure from feet of the wearer or a pressure from a shoe insert, which is transferred from the feet of the wearer, may be well transferred to the upper case 761. The upper case 761 may include an elastic material if necessary to well transfer the pressure to the conductive member 630. For example, the upper case 761 may be formed of a silicon material.

The lower case 762 may be coupled to the lower end of the upper case 761 to form a lower appearance of the smart shoes sensor module 200.

The first circuit 651 may be provided by being packaged in the housing 760 in which the upper case 761 and the lower case 762 are formed, and especially may be fixed to the lower case 762.

The first circuit 651 may partially be exposed from one surface on the substrate 650 and then may be in contact with the conductive member 630 which will be described later.

The first circuit 651 may be implemented as a coupling type of a film and a metal electrode or may be implemented as a coupling type of a film and a conductive polymer. Or, the first circuit 651 may be implemented in a type of a film and CNT or a type of a film and Graphene.

Or, the first circuit 651 may be provided in a type of a molding material and MID (Mold Interconnect Devices).

The substrate 650 may package the first circuit 651. The substrate 650 may package a second circuit for driving the motion sensor 243. The substrate 650 may package the controller 280. However, it is not required that the motion sensor 243, the second circuit or the controller 280 should be provided in the smart shoes sensor module 200. The smart shoes 110 may include the motion sensor, 243, the second circuit or the controller 280, which is separately provided, in accordance with the need or the system.

The conductive member 630 may generate an electric signal in the first circuit 651.

The conductive member 630 may be packaged in the housing 760 in which the upper case 761 and the lower case 762 are formed, and especially may be provided at an inner side of the upper case 761.

The conductive member 630 may be provided at the inner side 7611 of the upper case to form a first gap with the first circuit 651, and may elastically move by means a pressure of a threshold value or more which acts on the upper case 761 in a first direction, whereby the conductive member 630 may be in contact with the first circuit 651 and may generate a signal.

That is, the conductive member 630 may perform the function of the pressure sensor 246 (see FIG. 2) in accordance with the pressure of a threshold value or more, which acts on the upper case 761, in contact with the first circuit 651. If the pressure of a threshold value or more acts on the smart shoes sensor module 200, an electric signal may be generated in the first circuit 651.

The conductive member 630 may serve to electrically connect the first circuit 651 when it is in contact with the first circuit 651. The conductive member 630 may include a conductive material. Therefore, the conductive member 630 may be implemented as a conductive silicone, metal gasket, metal plate material or metal deposition, conductive polymer, CNT, Graphene, etc.

Or, the first circuit 651 may be configured by combination of a molding material and MID (Mold Interconnect Device).

For convenience of description, the state that no pressure acts on the smart shoes sensor module 200 will be referred to as a first state, and the state that a pressure acts on the smart shoes sensor module 200 will be referred to as a second state.

At the first state, the conductive member and the first circuit 651 may form a first gap G1. The first gap G1 may be a specific value that exceeds 0 mm.

At the first state, the first gap G1 may be maintained, and at the second state, the conductive member 630 and the first circuit 651 may be in contact with each other by elastic movement of the upper case 761.

When the smart shoes sensor module 200 is formed, the first gap G1 may be varied depending on manufacturing tolerance of the upper and lower cases 761 and 762, manufacturing tolerance and coupling tolerance of the conductive member 630 and the substrate 650 provided with the first circuit 651, coupling tolerance of the conductive member 630 and the upper case 761, and coupling tolerance between the upper case 761 and the lower case 762.

If the first gap G1 does not have a fixed value, a threshold pressure value of signal occurrence is varied, whereby a boundary of the on signal and the off signal may be formed.

If a step generated due to offset in identification of the on signal and the off signal is not recognized, or if it is recognized that a step is generated although the step is not generated, a problem may occur in that an error is generated in analysis of a step pattern of the wearer and an accumulated error is generated to cause a different result.

Therefore, at the first state, the first gap G1 is maintained, that is, the conductive member 630 and the first circuit 651 are in contact with each other so as not to generate the on signal, whereby reliability may be maintained.

The upper case 761 and the lower case 762 may be coupled to each other as a pair of a coupling groove and a coupling protrusion.

The coupling groove and the coupling protrusion may be fixed to each other by a fitting manner, and may prevent the upper case 761 and the lower case 762 from being opened unintentionally.

The coupling groove may be provided at one side of the upper case 761 or the lower case 762, and the coupling protrusion may be provided at the other side.

The coupling groove and the coupling protrusion may be in contact with each other at their respective sides to exert a fitting effect.

The coupling groove and the coupling protrusion may form a second gap G2 with respect to a longitudinal direction. The second gap G2 may prevent a width of the first gap G1 from being varied due to tolerance generated between the coupling groove and the coupling protrusion.

Similarly, a third gap G3 may be formed at an outer boundary between the upper case 761 and the lower case 762.

A support rib may be protruded from the inner side of the upper case 761 toward a downward direction to support the substrate 651 that includes the first circuit 651. If the first circuit 651 is packaged in the lower case 762, the support rib may serve to allow the substrate 651, which includes the first circuit 651, not to move, thereby minimizing tolerance generated in the first gap G1 due to a space.

A hook portion may be provided to be protruded at the inner side of the lower case 762 and fix the substrate 650 that includes the first circuit 651.

The conductive member 730 may be coupled to the inner side 7611 of the upper case 761. In this case, the conductive member 730 may be coupled to the inner side 7611 of the upper case 761 through an adhesive tape, or may be coupled to the inner side 7611 of the upper case 761 simultaneously with the formation of the upper case 761 or at another time different from the formation of the upper case 761 by a double injection molding.

If the conductive member 730 is coupled to the inner side 7611 of the upper case 761, the conductive member 630 may be provided in a recess area of the upper case 761 to improve reliability of the coupling. The recess area may increase a contact area between the conductive member 630 and the inner side 7611 of the upper case, and may serve to assure a space to allow the conductive member 630 to have a predetermined thickness or more.

Figure 10:
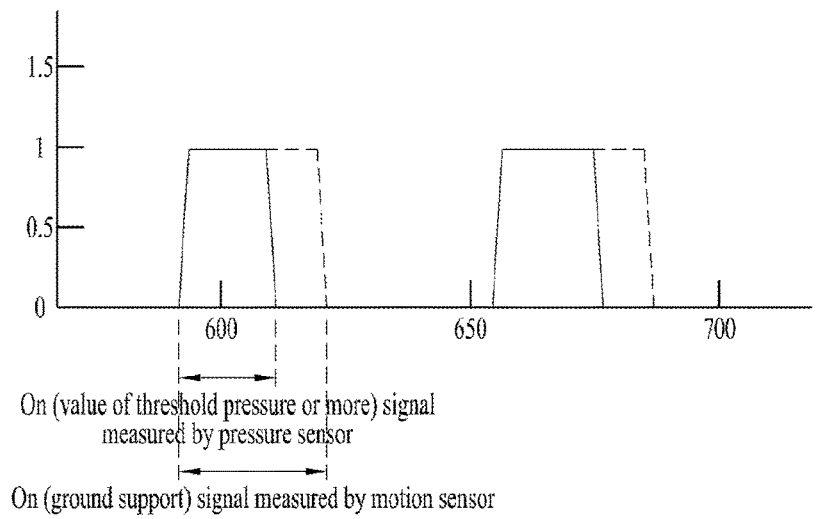
FIG. 10 is a view illustrating time difference between an on-signal measured by a motion sensor 243 of smart shoes 100 and an on-signal measured by a pressure sensor 246 in accordance with one embodiment of the present invention.

FIG. 10 is a view illustrating time difference between an on-signal measured by a motion sensor 243 of smart shoes 100 and an on-signal measured by a pressure sensor 246 in accordance with one embodiment of the present invention.

The motion sensor 243 may identify a three-dimensional location of the smart shoes 110 through the acceleration sensor 244 and the gyro sensor 245 in real time.

As a result, the controller 280 may identify and analyze whether the smart shoes sensor module 200 is an on signal state supported on the ground, that is, a value of '1' or an off signal state far away from the ground, that is, a value of '0'.

Meanwhile, the pressure sensor 246 may analyze the on signal state estimated to be supported on the ground or the off signal state estimated to be far away from the ground depending on the threshold pressure value or more for signal occurrence.

However, if the on signal or the off signal is determined through the pressure sensor 246, an error may occur due to manufacturing tolerance or coupling tolerance of the smart shoes sensor module 200.

Therefore, it is required that the state of the on signal or off signal, which is measured and analyzed through the pressure sensor 246 should be corrected to the on signal or off signal state measured or analyzed through the motion sensor 243, or vice versa.

Figure 11:
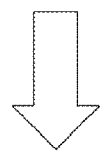
FIGS. 11 and 12 are algorithm and flow chart illustrating that a smart shoes on-signal value measured through a pressure sensor 246 is calibrated to a smart shoes on-signal value measured through a motion sensor 243 in accordance with one embodiment of the present invention.
Figure 12:
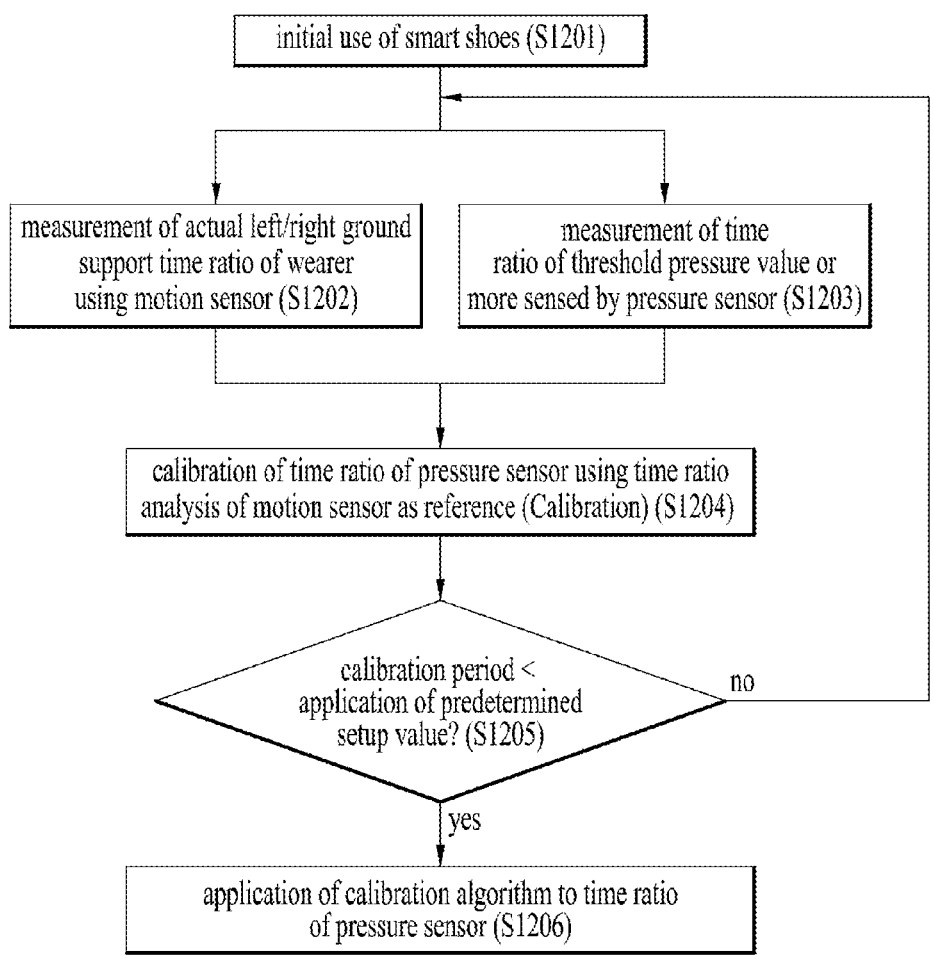

FIGS. 11 and 12 are an algorithm and a flow chart illustrating that a smart shoes on-signal value measured through a pressure sensor 246 is calibrated to a smart shoes on-signal value measured through a motion sensor 243 in accordance with one embodiment of the present invention.

The smart shoes sensor module 200 may be provided at each of a left (L) smart shoe and a right (R) smart shoe to analyze a step pattern of the wearer.

The smart shoes sensor module 200 provided at the left (L) smart shoe will be defined as a left (L) smart shoe sensor module, and the smart shoes sensor module 200 provided at the right (R) smart shoe will be defined as a right (R) smart shoe sensor module. A unit of organically measure and analyze the left (L) smart shoe sensor module and the right (R) smart shoe sensor module is defined as a smart shoes sensor module system.

That is, a measured value or analyzed value of any one of the left (L) smart shoe sensor module and the right (R) smart shoe sensor module may be transmitted to the smart shoe sensor module of the other side, or a separate mobile terminal may perform correction by receiving the measured value and analyzed value of each smart shoe sensor module.

In the former case, the left (L) smart shoe sensor module and the right (R) smart shoe sensor module may be regarded as the smart shoes sensor module system. In the latter case, the left (L) smart shoe sensor module, the right (R) smart shoe sensor module and the separate mobile terminal may be regarded as the smart shoes sensor module system.

The aforementioned error between the pressure sensor 246 and the motion sensor 243 in FIG. 10 may be enlarged to a problem of an on signal time of the left smart shoe and the right smart shoe.

The time supported on the ground depending on the step pattern of the wearer, that is, the time or ratio that a pressure of a threshold value or more is applied may differently be applied to the left (L) smart shoe and the right (R) smart shoe. Therefore, this difference may cause an inexact result during analysis of the step pattern of the wearer. It is therefore required to correct such a difference in balance.

A difference in left and right sides for analysis of the time of the left and right (L/R) smart shoes sensor module 200 supported on the ground may occur due to complex factors such as a difference caused by imbalance between left and right weights of the wearer as well as a factor caused by manufacturing tolerance of each of the left/right (L/R) smart shoes sensor modules 200.

Therefore, it is required to calibrate time difference of the left/right (L/R) smart shoes supported on the ground, which is measured by the pressure sensor 246.

Such calibration may be performed through support time analysis of the motion sensor 243 supported on the ground, wherein the motion sensor 243 is provided at each of the left/right (L/R) smart shoes.

The motion sensor 243 may measure three-dimensional locations of the left/right (L/R) smart shoes 110 through the acceleration sensor 244 and the gyro sensor 245 in real time, as described above.

The motion sensor 243 may analyze a start point and an end point of the smart shoes 110 supported on the ground on the basis of the measured locations.

The difference in the on signal time ratio of the left/right smart shoes 110, which is identified through the pressure sensor 246, may be calibrated based on the ratio of the support time of each of the left/right (L/R) smart shoes supported on the ground, which is analyzed through the motion sensor 243.

For example, if the smart shoes 110 are initially used, a calibration algorithm may be actuated automatically (S1201).

The controller 280 may analyze the ground support time ratio through three-dimensional movement of the left/right (L/R) smart shoes 110, which is measured by the motion sensor 243 that includes the acceleration sensor 244 and the gyro sensor 245 (S1202), and may analyze the time ratio acted on the left/right smart shoes 110 at a threshold pressure value or more, which is measured by the pressure sensor 246 (S1203).

The measuring or analyzing steps may be performed at the same time or different times.

For example, it is assumed that the ground support time ratio measured and analyzed through the motion sensor 243 is 0.8:1.2, and the time ratio acted on the left/right smart shoes 110 at a signal occurrence threshold pressure value or more, which is measured and analyzed through the pressure sensor 246, is 0.9:1.1.

In this case, the controller 280 may apply a calibration algorithm that multiplies 0.8/0.9 by the value measured by the pressure sensor 246 of the left (L) smart shoe and multiples 1.2/1.1 by the value measured by the pressure sensor 246 of the right (R) smart shoe (S1204, S1206).

However, in order to minimize power consumption, the controller 280 may drive the motion sensor 243 at only the initial correction step of the pressure sensor 246 and disable driving of the motion sensor 243 if it is not necessary.

That is, the controller 280 may temporarily enable the motion sensor 243, which is disabled, when performing calibration.

Calibration of the controller 280 may be performed by a cycle set by the wearer, or may be performed automatically at a predetermined cycle (S1205).

The smart shoes system according to the present invention has been described with reference to FIGS. 1 to 12. Hereinafter, a smart shoes tracing algorithm based on sensing data of the pressure sensor in a PDR (Pedestrian Dead Reckoning) algorithm, will be described in detail.

Hereinafter, the smart shoes system operated based on the smart shoes tracing algorithm will be described in more detail.

In this case, the smart shoes tracing algorithm may refer to sensing data of the pressure sensor in the PDR algorithm to exactly sense movement (for example, every step) of the smart shoes wearer without missing the movement. If the smart shoes tracing algorithm is used, movement data such as step track, step direction, stride and height of the smart shoes wearer may be calculated more easily and exactly. Moreover, if the smart shoes tracing algorithm is used, power consumption may be minimized and efficiency may be maximized as compared with the smart shoes system of the related art, in association with the aforementioned pressure switch or pressure sensor circuit or module.

The smart shoes according to the present invention may perform tracing, sensing and recording of movement data such as moving time, velocity, distance or position, orientation, trace or path, altitude and stride in a state that the user wears the smart shoes. At this time, it is important to exactly perform tracing and sensing without missing every step of the smart shoes wearer.

In respect of the present invention, in sensing movement data of the smart shoes wearer, if movement data of the wearer is measured using only the motion sensor (or referred to as PDR sensor or inertia sensor) such as the acceleration sensor and the gyro sensor, the motion sensor should always maintain a measurable state. However, enabling of the motion sensor causes continuous battery consumption. Also, when the movement data is sensed using the motion sensor, a step of the wearer may not be identified exactly due to noise generated in the motion sensor, for example, an error such as missing of one step may occur. If this error is accumulated, an error occurs in the movement data of the wearer, which is acquired through sensing, whereby reliability is reduced. To solve this problem, the motion sensor of the present invention further includes a pressure switch or pressure sensor as described above. The pressure switch or pressure sensor will be described based on the aforementioned description, and its repeated description will be omitted.

Hereinafter, the smart shoes tracing algorithm, movement data sensing through the smart shoes tracing algorithm, and the smart shoes system for the movement data sensing will be described in more detail.

Figure 13:
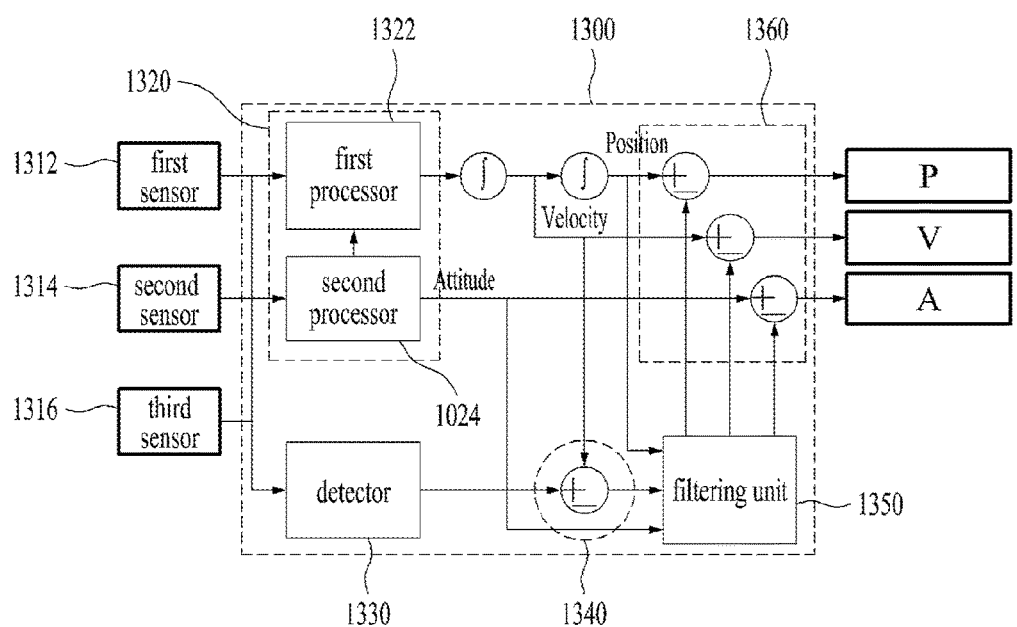
FIG. 13 is a schematic block diagram illustrating a tracing algorithm in a smart shoes system according to one embodiment of the present invention.

FIG. 13 is a schematic block diagram illustrating a tracing algorithm in a smart shoes system according to one embodiment of the present invention.

Referring to FIG. 13, the smart shoes tracing algorithm may be processed by a component called a smart shoes tracing data processor 1300 (hereinafter, referred to as 'tracing data processor'). The scope of the tracing data processor 1300 should be determined with reference to its function or role. The tracing data processor 1300 may be implemented by hardware such as circuit or module or embedded software embedded in one component of the aforementioned smarts shoes system. However, it is not required that the tracing data processor 1300 disclosed in FIG. 13 and this specification should be one component of the smart shoes. The tracing data processor 1300 may be designed as one component included in another device (including server) such as a mobile terminal that may receive and process sensing data of the sensors of the smart shoes.

The tracing data processor 1300 may accumulate and calculate a moving distance (position (3D)) by estimating a moving velocity (3D)) and a moving direction (attitude (3D)) of the smart shoes wearer through a sensor module mounted in the smart shoes.

The tracing data processor 1300 may process tracing data for the smart shoes wearer by using a processor 1320 and a filtering unit 1350 on the basis of sensing data of the sensor module mounted in the smart shoes. This is related to a PDR algorithm related to an inertia navigation system of the related art, and its detailed description will be based on the PDR algorithm of the related art. In this case, the detailed description of the PDR algorithm will be omitted.

First of all, a procedure of processing tracing data through the processor 1320 and the filtering unit 1350 will be described.

The processor 1320 includes a first processor 1322 and a second processor 1324.

The first processor 1322 receives data sensed by a first sensor 1312, processes the received sensing data and outputs the processed data to a first integrator. In this case, the first sensor 1312 includes an acceleration sensor, for example. Particularly, the first processor 1322 subtracts gravity from the data sensed by the first sensor 1312.

The second processor 1324 receives data sensed by a second sensor 1314, and processes the received sensing data. The processed data are output to the first processor 1322 and a mixer. In this case, the second sensor 1314 includes a gyro sensor, for example. Moving direction data may include yaw data, pitch data, roll data, etc. The second processor calculates a moving direction A of an insole of the smart shoes on the basis of the data sensed by the second sensor 1314.

The output data of the first integrator may be moving velocity data V, and the data processed by the second processor 1324 may be moving direction data A of the smart shoes wearer.

The data excluding the moving velocity data v1 from the output data of the first integrator, that is, moving distance data p0 are input to a second integrator and then accumulated. The moving velocity data v1, the output data of the second integrator, that is, moving distance data p1, and moving direction data a1 of the second processor 1324 are input to the filtering unit 1350. The filtering unit 1350 filters the moving velocity data v1, moving distance data p1 and moving direction data a1, which are input, using a Kalman filter, which is mainly used in the aforementioned PDR algorithm. The input moving velocity data v1, moving distance data p1 and moving direction data a1 are filtered by the filtering unit 1350, whereby moving velocity data v2, moving distance data p2 and moving direction data a2 are output. The output moving velocity data v2, moving distance data p2 and moving direction data a2 are output to a mixer 1360.

The mixer 1360 includes a first mixer related to a moving distance, a second mixer related to a moving velocity, and a third mixer related to a moving direction.

The first mixer calculates final moving distance data P by mixing the moving distance data p1 which are the output of the second integrator with the moving distance data p2 which are the output of the filtering unit 1350.

The second mixer calculates final moving velocity data V by mixing the moving velocity data v1 extracted from the first integrator with the moving velocity data v2 which are the output of the filtering unit 1350.

The third mixer calculates final moving direction data A by mixing the moving direction data a1 which are the output of the second processor 1324 with the moving direction data a2 which are the output of the filtering unit 1350.

Figure 14:
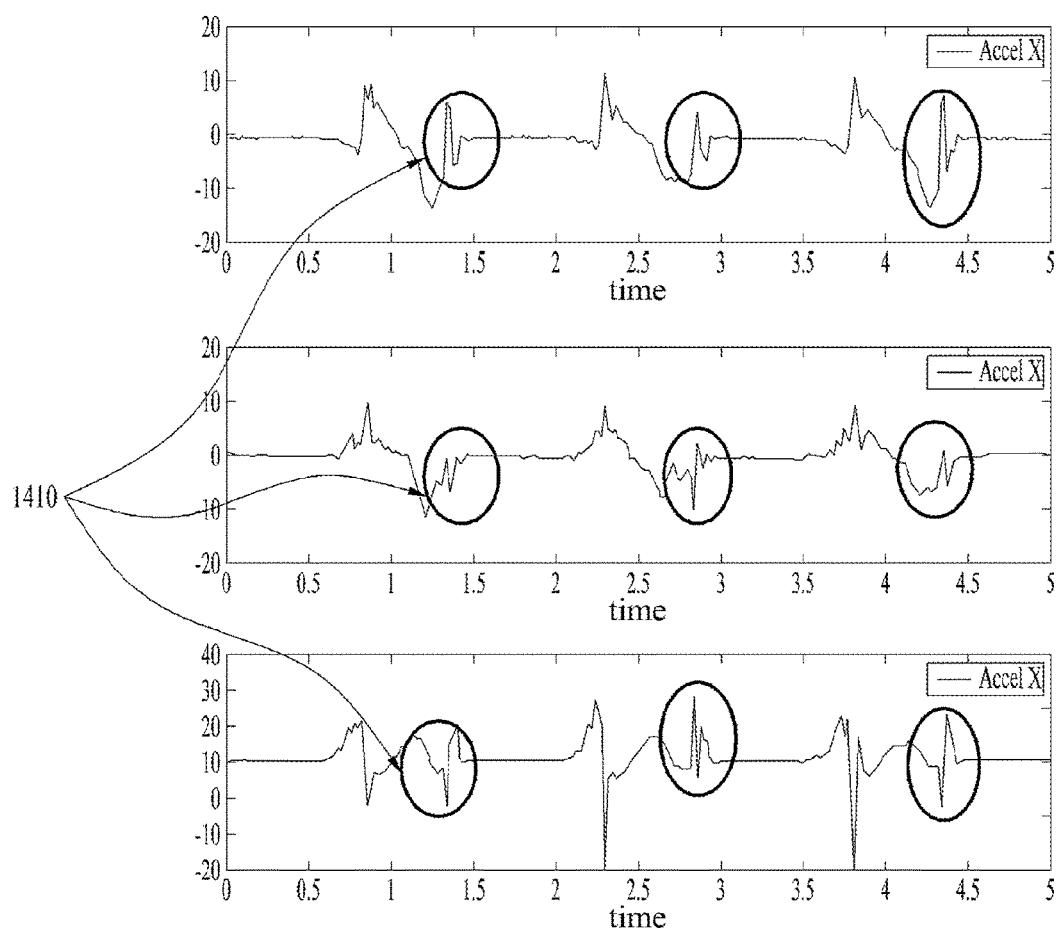
FIG. 14 is a smart shoes tracing data graph according to one embodiment of the present invention.

If the tracing data processor 1300 processes the tracing data of the smart shoes wearer by using the processor 1320 and the filtering unit 1350 of FIG. 13 on the basis of the sensing data of the sensor module mounted in the smart shoes, sensing data such as a graph shown in FIG. 14 may be obtained.

However, referring to FIG. 14, if the tracing data are processed based on only the data sensed by the first sensor 1312 and the second sensor 1314, every step of the smart shoes wearer may not be detected exactly due to a noise area 1410. This is because that one step of the smart shoes wearer may be missed as it is difficult to exactly measure zero velocity for every step of the smart shoes wearer in accordance with an effect of the noise and thus it is ambiguous to identify a previous step from next step. This may not cause a big problem in a state that the smart shoes wearer simply walks or does not move. However, if a moving velocity is increased or stride is narrow, it may affect an effect of whole data to cause an error. Therefore, since the error according to the noise area may affect reliability of the sensed tracing data, there may be a problem. Meanwhile, the noise area 1410 in this specification may not mean only an area where noise is generated but mean a point or area where an error may occur during data sensing related to the present invention.

To minimize or remove the error according to the noise, the present invention will be described with reference to sensing data of the aforementioned pressure sensor.

Referring to FIG. 13, the tracing data processor 1300 further includes a detector 1330 and a fourth mixer 1340.

The detector 1330 receives data sensed by a third sensor 1316, processes the received data, and outputs the processed data to the fourth mixer 1340. In this case, the third sensor 1316 may be the aforementioned pressure sensor according to the present invention. Therefore, the aforementioned description of the pressure sensor is applied to the third sensor, and the detailed description of the third sensor will be omitted. The data sensed by the pressure sensor may be generated per step of the smart shoes wearer. This may be a graph shown in FIG. 15 or 16.

The detector 1330 detects a zero velocity from the data input by being sensed by the third sensor 1316. The zero velocity may easily be detected from the graph data shown in FIG. 14, which are sensed as the third sensor 1316 is operated as a pressure switch according to every step of the wearer.

Zero velocity data z1 detected from the detector 1330 are mixed with the moving velocity data v1 extracted from the first integrator by the fourth mixer 1340, and the mixed data become an input v1' different from the input v1 of the filtering unit 1350. Afterwards, as described above, the data are filtered by the filtering unit 1350 and then moving distance P, moving velocity V and moving direction A data are calculated.

Figure 15:
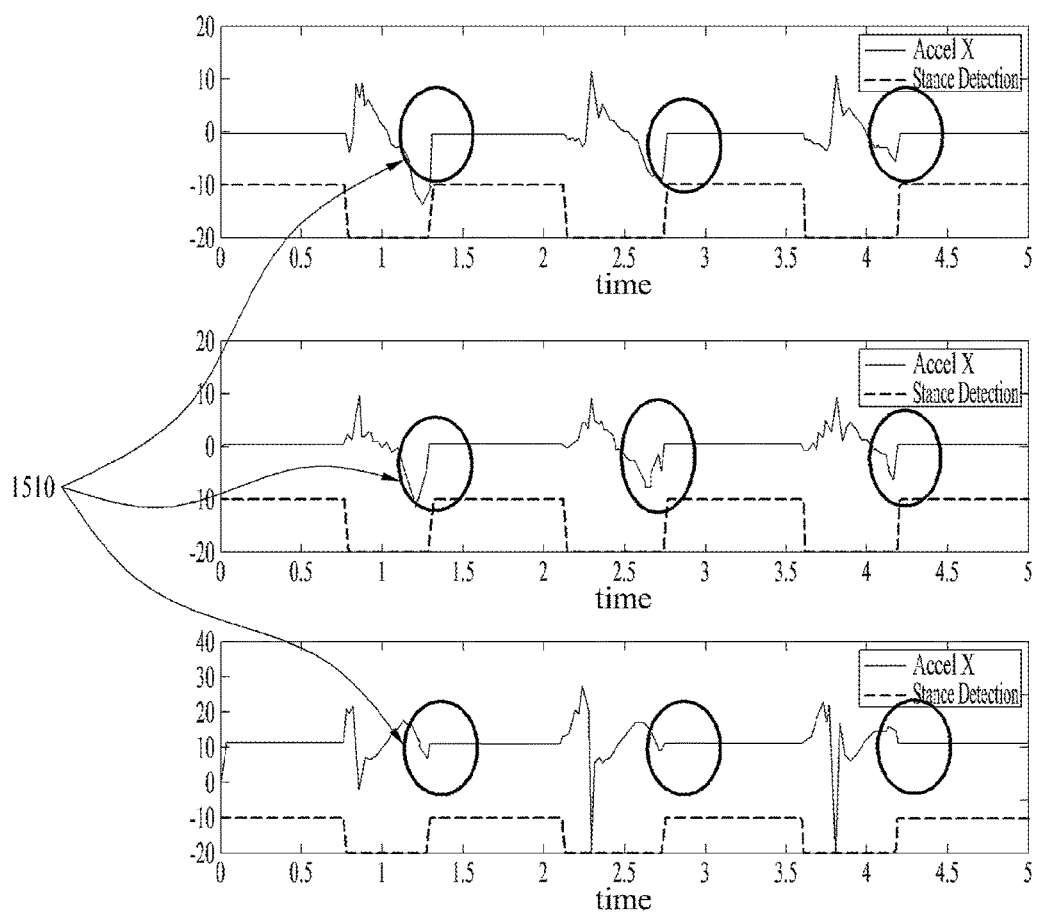
FIGS. 15 and 16 are smart shoes tracing data graphs according to another embodiment of the present invention.

This will be described with reference to FIGS. 14 and 15. As described above, the noise area 1410 exists in FIG. 14. However, referring to FIG. 15, the data 1510 filtered through the detector 1330 and the fourth mixer 1340 counterbalance the noise shown in FIG. 14 to minimize the zero velocity, whereby every step of the wearer may be recognized and processed definitely. Therefore, referring to FIG. 14, a portion that may be missed with respect to a specific step that may occur may be compensated, whereby exact data may be calculated.

Figure 16:
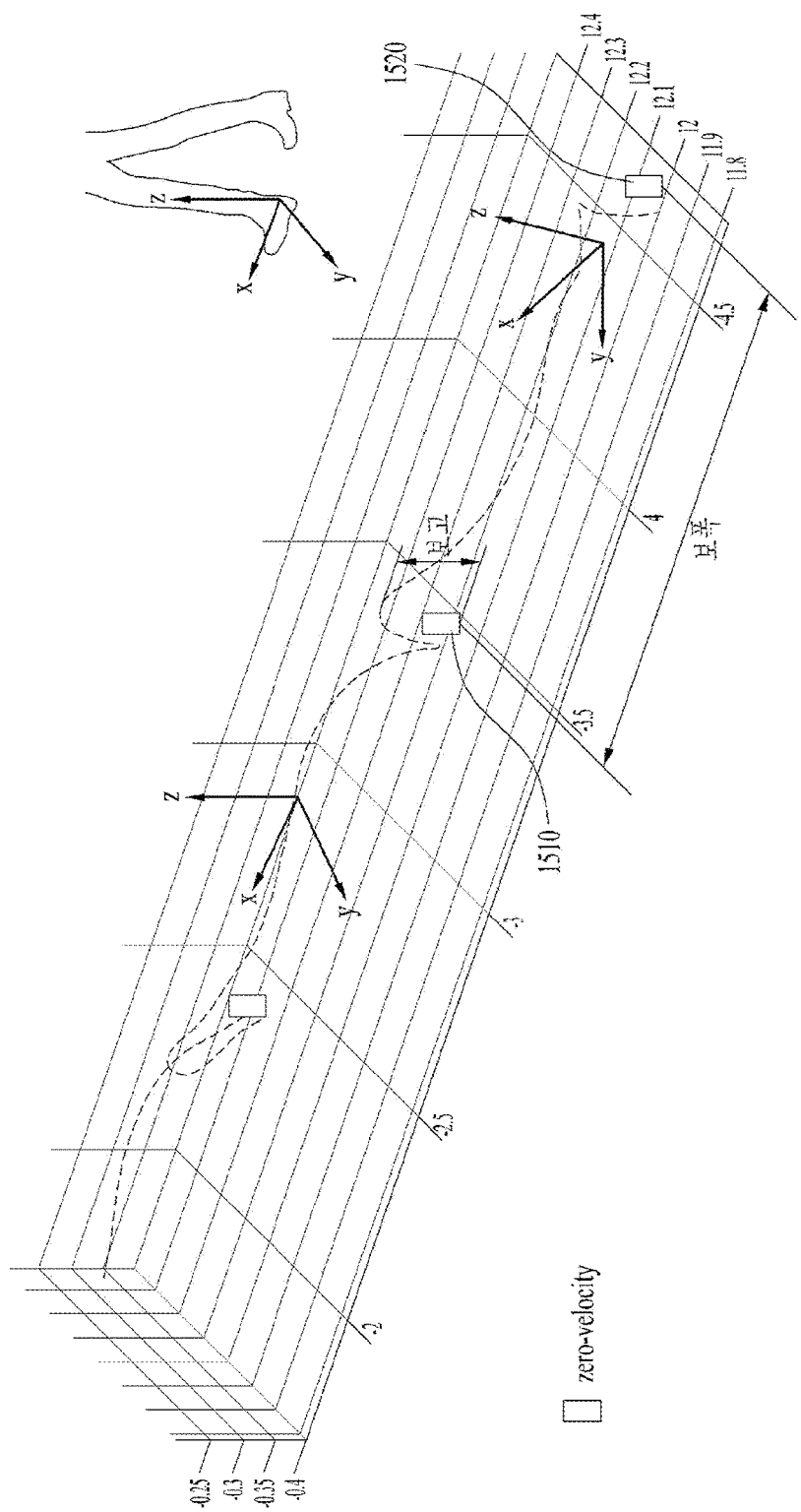

Therefore, referring to FIG. 16, the zero velocity is minimized with respect to movement data of the smart shoes wearer, that is, movement of axes x, y and z, whereby every step of the smart shoes wearer may be calculated exactly. Based on this result, according to the present invention including the PDR algorithm, foot angle data or foot angle correction data may be calculated easily and exactly, whereby step track, step velocity, step direction, stride and height of the smart shoes wearer may be calculated more easily and exactly as shown in FIG. 16. This may enhance efficiency of the system and reduce power consumption as compared with the case that correction is required due to the accumulated error as zero velocity of one step is not acquired exactly by the PDR sensor or inertia sensor only. Also, if only the data of the PDR sensor are used, wireless positioning calibration is required based on Wi-Fi or Bluetooth. However, if the data of the pressure data are also used, data sensing may be performed more exactly even without the wireless positioning calibration.

Also, in respect of stride or height, a barometer sensor based on altitude is used in case of hiking or building stairs in the related art. However, in this case, ambient pressure is rapidly changed due to weather change, wind, etc., or pressure change is serious and exact data sensing cannot be performed due to factors such as opening or closing of a window or door in case of stairs. Also, a problem occurs in that reliability of the sensed data is low. On the other hand, in the present invention, zero velocity is minimized based on the sensing data of the simple pressure sensor (pressure switch), whereby data may be calculated easily and exactly even without barometer sensor or other component.

The tracing data processing algorithm according to the present invention may be used for a movement information tracing and management service of the smart shoes wearer to measure calories consumption and weight change of the smart shoes wearer, and may automatically recognize bike riding, walking, running, etc. to enable navigation or scheduling service according to the recognized result. The tracing data processing algorithm of the present invention enables various services such as a step posture tracing and management service of a wearer (soldier, etc.), an indoor navigation service of mart, library, public institution, etc., a movement amount measurement and management service based on outdoor bike, walking navigation accuracy correction service, a tracing history management of a walking area, stride, and height, and a wearer tracing management service in a GPS or Wi-Fi unavailable area.

Figure 17:
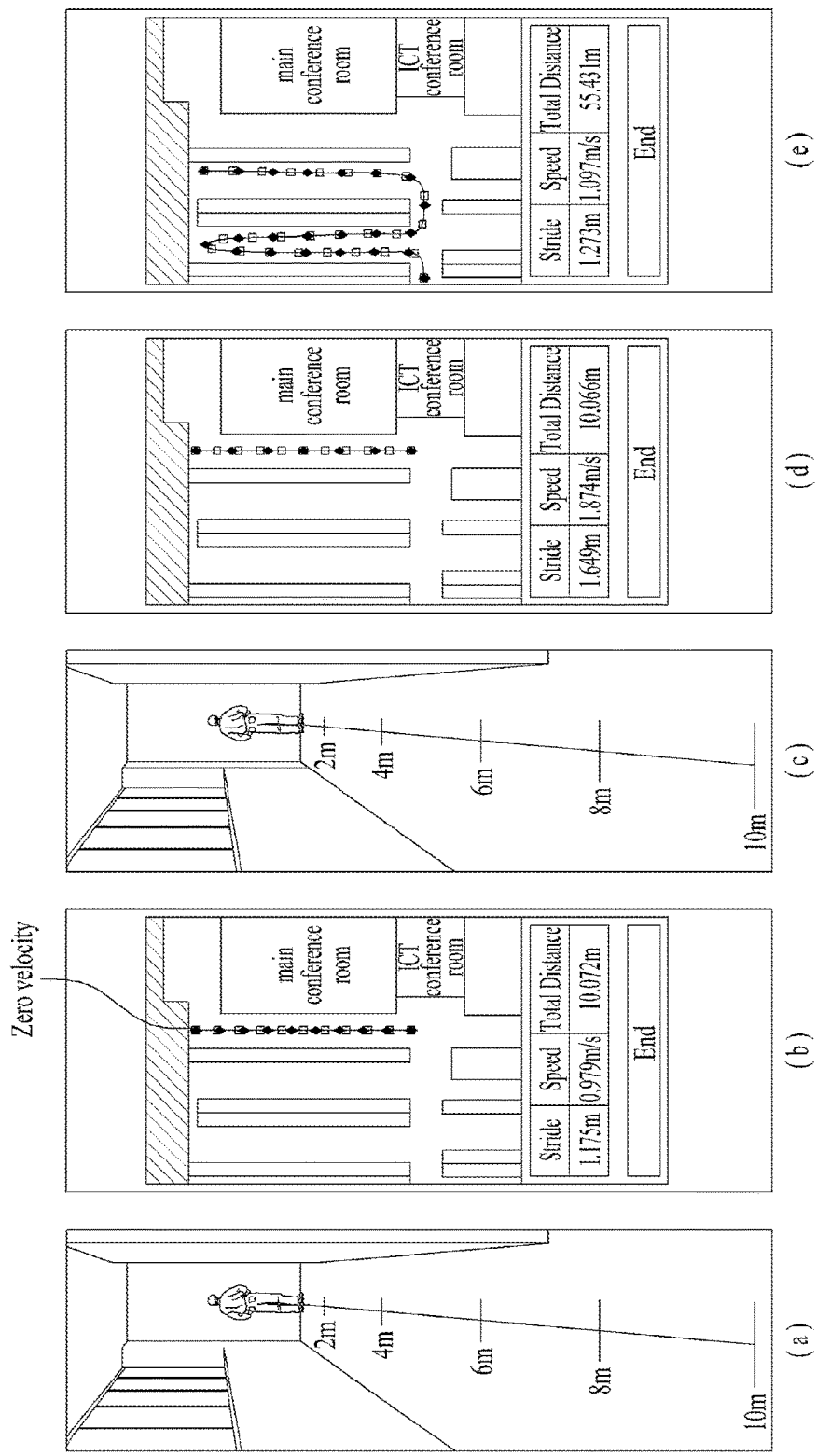
FIG. 17 is a view illustrating a UX of one example of a service scenario according to one embodiment of the present invention.

FIG. 17 is a view illustrating a UX of one example of a service scenario according to one embodiment of the present invention.

FIG. 17a illustrates a case that a wearer walks a moving distance of 10 m at an average velocity, and FIG. 17b is a UX of data acquired through the tracing data processor in FIG. 17a. In FIG. 17a, it is noted that the data acquired through the tracing data processor with respect to the moving distance of 10 m correspond to 10.072 m.

FIG. 17c illustrates a case that a wearer walks a moving distance of 10 m at a fast velocity, and FIG. 17d is a UX of data acquired through the tracing data processor in FIG. 17c. In FIG. 17c, it is noted that the data acquired through the tracing data processor with respect to the moving distance of 10 m correspond to 10.066 m.

In addition, FIG. 17e is a UX of stride, velocity and total distance data accumulatively acquired through the tracing data processor for a certain time.

Figure 18:
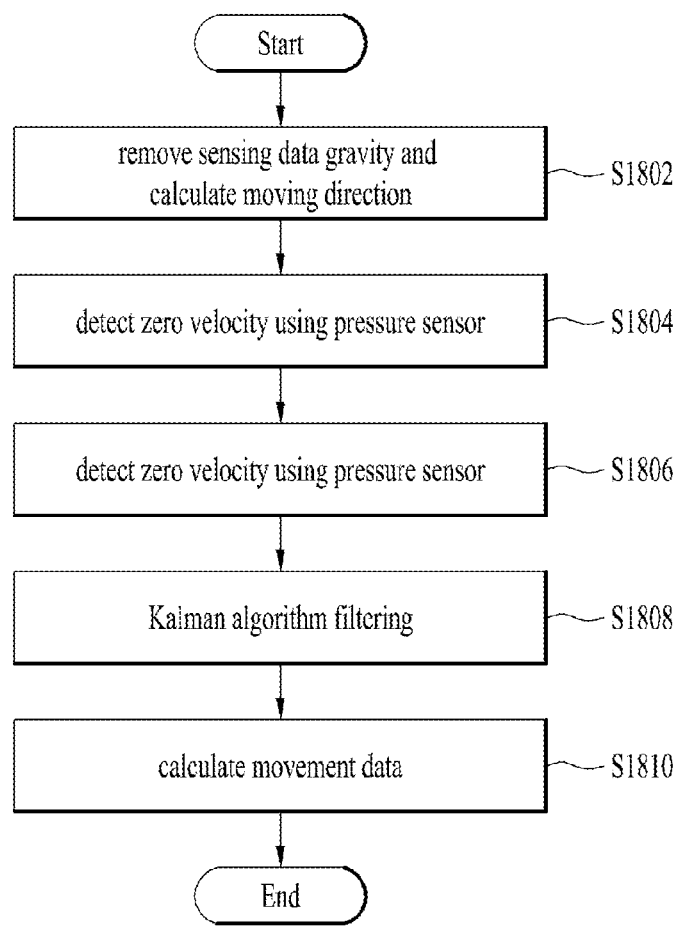
FIG. 18 is a flow chart illustrating a data processing method based on a tracing algorithm in a smart shoes system according to one embodiment of the present invention.

FIG. 18 is a flow chart illustrating a data processing method based on a tracing algorithm in a smart shoes system according to one embodiment of the present invention, According to the present invention, the tracing data processor of the smart shoes system receives sensing data from one or more first sensors (S1802), and detects zero velocity data by receiving the sensed data on the basis of an operation of a second sensor (S1804). In this case, the first sensors include the first sensor (acceleration sensor) and the second sensor (gyro sensor) of FIG. 13. Also, the second sensor includes the third sensor (pressure sensor) of FIG. 13.

The tracing data processor removes step noise of the sensing data received from the first sensors on the basis of the detected zero velocity data (S1806). The step noise means the noise 1410 shown in FIG. 14, and removal of the step noise means that the noise is processed as shown in FIG. 15.

The tracing data processor filters the sensing data from which the step noise is removed (S1808).

The tracing data processor acquires movement data of the smart shoes on the basis of the filtered sensing data and a predetermined threshold value (S1810). The predetermined threshold value may indicate a value according to data standardization based on filtering of the filtering unit. In this way, data standardization may be helpful for data management.

Figure 19:
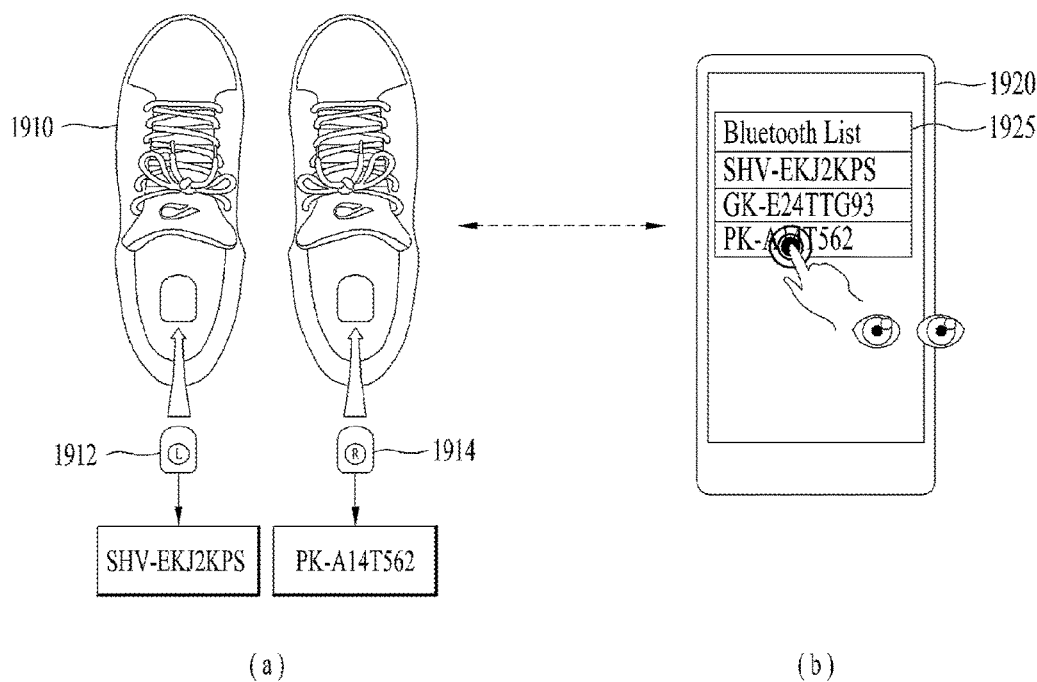
FIGS. 19 and 20 are views illustrating a pairing procedure between smart shoes and a mobile terminal in accordance with the present invention.
Figure 20:
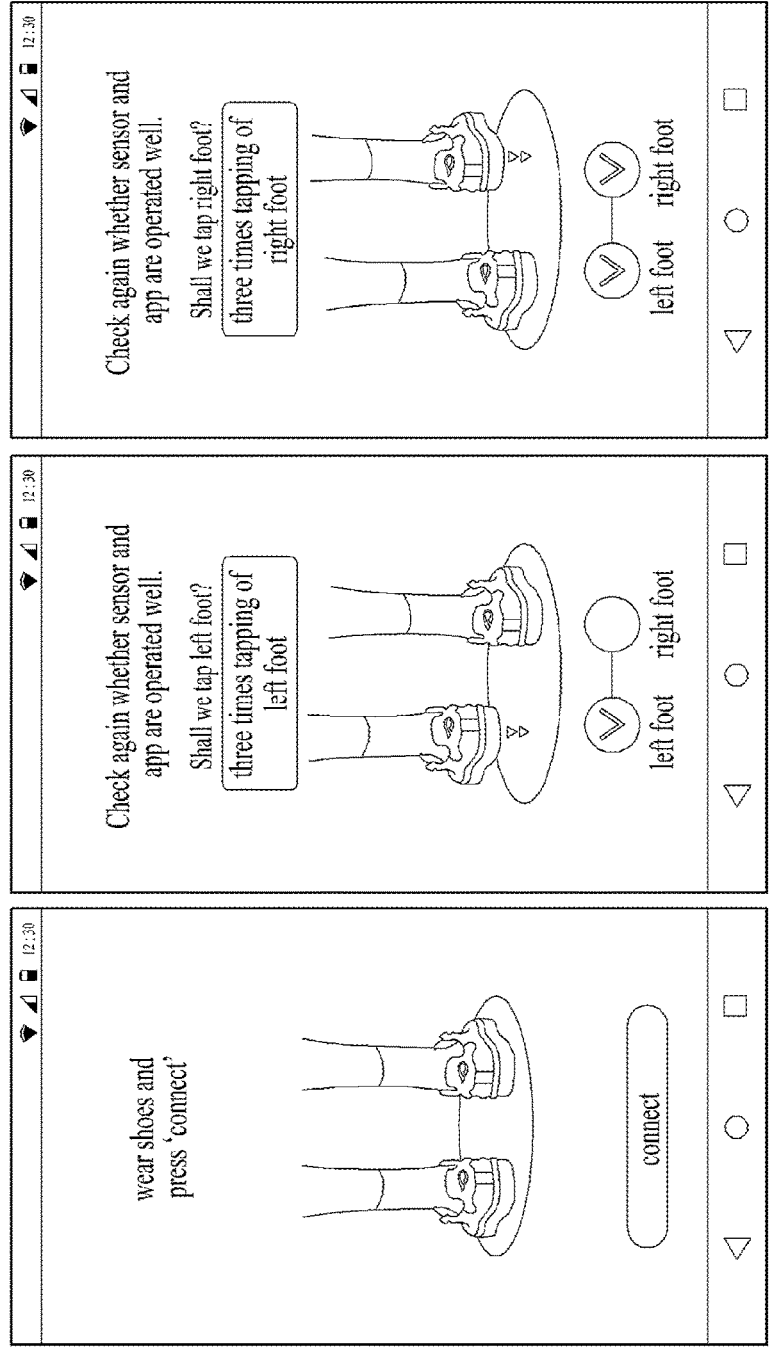

FIGS. 19 and 20 are views illustrating a pairing procedure between smart shoes and a mobile terminal in accordance with the present invention.

Based on the aforementioned embodiments, movement data may be sensed from smart shoes 1910, and a mobile terminal 1920 may acquire meaningful data from the data sensed from the smart shoes 1910. At this time, to actively perform data communication between the smart shoes 1910 and the mobile terminal 1920, a pairing procedure for data communication between them should be preceded.

For convenience, in this specification, it is assumed that the data communication is performed based on a Bluetooth communication protocol. Therefore, pairing for the data communication is performed in accordance with definition in the Bluetooth communication protocol. However, in this case, the communication protocol is not limited to the Bluetooth communication protocol, and may include all communication protocols currently defined for data communication, such as Wi-Fi, LTE, and ZigBee, or communication protocols which will be defined later.

Meanwhile, only one communication protocol is not used for the data communication. A plurality of communication protocols may be used in accordance with various criteria such as data amount and data attributes. For example, a predetermined communication protocol may exist for urgent data processing such as emergency alert message (EAS). In addition, another communication protocol may be used if data communication is not performed actively in accordance with a communication condition.

Referring to FIG. 19*a*, a first smart shoes sensor module 1912 is mounted in a left (L) smart shoe constituting the smart shoes, and a second smart shoes sensor module 1914 is mounted in a right (R) smart shoe. The first smart shoes sensor module 1912 and the second smart shoes sensor module 1914 may have their unique identification data in accordance with a communication protocol for data communication. For example, referring to FIG. 19*a*, the first smart shoes sensor module 1912 has unique identification data called 'SHV-EKJ2KPS' for data communication, and the second smart shoes sensor module 1914 has unique identification data called 'PK-A14TS62' for data communication.

The unique identification data may be given during a manufacturing step of the smart shoes in accordance with a manner scheduled or defined by a corresponding communication protocol in case of a predetermined communication protocol, for example, Bluetooth. Even though the unique identification data are given for a specific communication protocol, the unique identification data may be used when another communication protocol is used. The unique identification data may be given for common use from the time when the smart shoes are manufactured. Alternatively, the unique identification data may be changed randomly by a user for identification convenience of the user within the range that does not affect data communication or a manner defined in the communication protocol.

The mobile terminal 1920 may provide an available Bluetooth communication list 1925 on its screen as shown in FIG. 19*b* if the mobile terminal enables or turns on Bluetooth communication for data communication.

Therefore, the user may perform pairing by selecting a desired device from the list provided on the mobile terminal 1920. However, at this time, if a password is set to the selected device, the pairing procedure may be completed through password input together with appropriate UX. Also, when pairing is completed, it is difficult for the user to identify whether pairing has been performed normally. Therefore, smart shoes shaped UX may be provided on the screen of the mobile terminal in accordance with the system to allow the user to view the pairing procedure, or a feedback such as vibration may be given from the paired smart shoes to the user, whereby the user may easily recognize the result of the pairing.

Unlike FIG. 19, in FIG. 20, automatic pairing may be performed based on the result according to a predetermined activity of the smart shoes wearer without the separate list shown in FIG. 19*b*. This may be helpful for more intuitive and convenient pairing under various statuses that the user cannot touch or input the mobile terminal or it is difficult for the user to select a desired device due to too many device lists which are provided.

As shown in FIG. 20*a*, if the user wears the smart shoes and pushes or selects 'connect' in accordance with a guide on the UX, the mobile terminal 1920 requires additional operation for pairing as shown in FIGS. 20*b* and 20*c*. If a pairing request with the smart shoes is selected by the mobile terminal in FIG. 20*a*, the smart shoes wearer is requested to tap a left foot three times to identify whether a sensor and an application are operated well in FIG. 20*b*. If the smart shoes wearer performs the operation according to the request of the mobile terminal, the left (L) smart shoes sensor module and the mobile terminal are automatically registered and paired. Afterwards, if the smart shoes wearer performs the operation requested for the right (R) smart shoes sensor module in FIG. 20*c* like FIG. 20*b*, the mobile terminal automatically performs registration and pairing. FIGS. 20*b* and 20*c* are intended for registration and pairing of both the left and right smart shoes sensor modules, and the order of registration and pairing thereof is random and is not important. If the sensor module is mounted in any one of the smart shoes, any one of FIGS. 20*b* and 20*c* is performed.

In FIG. 20, the mobile terminal performs a previous identification function as to whether active data communication is performed as well as automatic registration and pairing of the sensor modules mounted in the smart shoes. Also, since it is difficult for the user to determine whether data sensing is performed normally if the operations shown in FIG. 20 are not performed, a calibration task for more exact data sensing may be performed. For example, through FIG. 20b or 20c, the user may intuitively recognize intensity or level of a pressure for recognizing a step of the smart shoes wearer, and an error operation of the sensor module may be determined. As a result, the user may calibrate sensing sensitivity of the sensor module as the case may be. In other words, the sensor module of the smart shoes may have predetermined sensing sensitivity and a threshold pressure reference on the basis of average data.

However, since the level of data sensing felt by the corresponding user may be varied even based on the reference, this may be easily calibrated through the procedure of FIG. 20b or 20c. For example, as described above, it is assumed that the user has performed the procedure shown in FIG. 20b or 20c for pairing. In this procedure, if the smart shoes wearer feels that data sensing is performed differently, the smart shoes wearer requests threshold pressure calibration, and the threshold pressure calibration is provided in the form similar to the UX provided in FIG. 20b or 20c, whereby the threshold pressure is controlled as desired by the user. In this case, the threshold pressure controlled or calibrated in FIG. 20b or 20c is transmitted from the mobile terminal to the smart shoes, and the controller of the smart shoes may control the sensor module based on the threshold pressure or re-classify or modify the data sensed by the sensor module.

Meanwhile, pairing has been performed through the operation such as tapping feet of the smart shoes wearer in FIG. 20, but the present invention is not limited to the number of times of tapping feet or tapping feet. Pairing may be performed through various operations that may be performed easily by the smart shoes wearer. Meanwhile, various operations in addition to the tapping feet, that is, a list for pairing may be provided and a pairing procedure may be performed in accordance with the operation selected by the user. In this case, the operation selected by the user may be used during execution of an application or for identification of the corresponding user. Alternatively, after paring request with the smart shoes, the mobile terminal may automatically pair with the smart shoes if a signal is continuously received in the smart shoes not a given pattern. Meanwhile, the mobile terminal may automatically pair with a device having the greatest signal intensity, that is, the smart shoes during pairing request.

Meanwhile, in respect of the present invention, the mobile terminal may identify the left (L) smart shoe from the right (R) smart shoe through a given gesture input if the sensor of the smart shoes, especially the gyro sensor has three axes. The mobile terminal may automatically identify the left (L) smart shoe from the right (R) smart shoe by comparing data received from each sensor module with each other without separate identification of the left (L) smart shoe from the right (R) smart shoe in case of 9-axis sensor (acceleration sensor of 3 axes, gyro sensor of 3 axes, and terrestrial magnetic sensor of 3 axes).

Moreover, if the mobile terminal registers a smart shoes application as a basic application, the mobile terminal may perform various operations such as lock and release of the mobile terminal, execution of a specific function, execution of a specific application, and control of the executed application based on a predetermined operation of the smart shoes wearer.

In addition, request, selection and function execution related to the smart shoes on the mobile terminal may be performed in various manners such as a voice, a gesture and an eye-tracking as well as a touch of the mobile terminal, or may be performed by combination of the above manners.

However, the procedure of FIG. 20 may be performed together with the procedure of FIG. 19. For example, after pairing in FIG. 19, start or end of actual data communication may be performed through the procedure of FIG. 20, or vice versa.

Meanwhile, referring to FIGS. 19 and 20, if the mobile terminal 1920 performs initial pairing with the smart shoes 1910 or performs pairing through the smart shoes application, the mobile terminal may perform automatic pairing based on pairing data which are previously stored. However, at this time, if the smart shoes application is used by the mobile terminal 1920, a list based on unique identification data of the smart shoes sensor modules shown in FIG. 19b is provided during initial pairing. However, unlike the aforementioned description, Bluetooth unique identification data of the mobile terminal not the smart shoes may be provided by filtering from the above list. Also, the aforementioned automatic pairing may acquire sensing data and calculate various movement data based on the tracing algorithm through setup or considering a previous use pattern of the user even without additional operation or input of the user and therefore automatically acquire and calculate the smart shoes data according to the acquired result and the calculated result and provide related UX.

Figure 21:
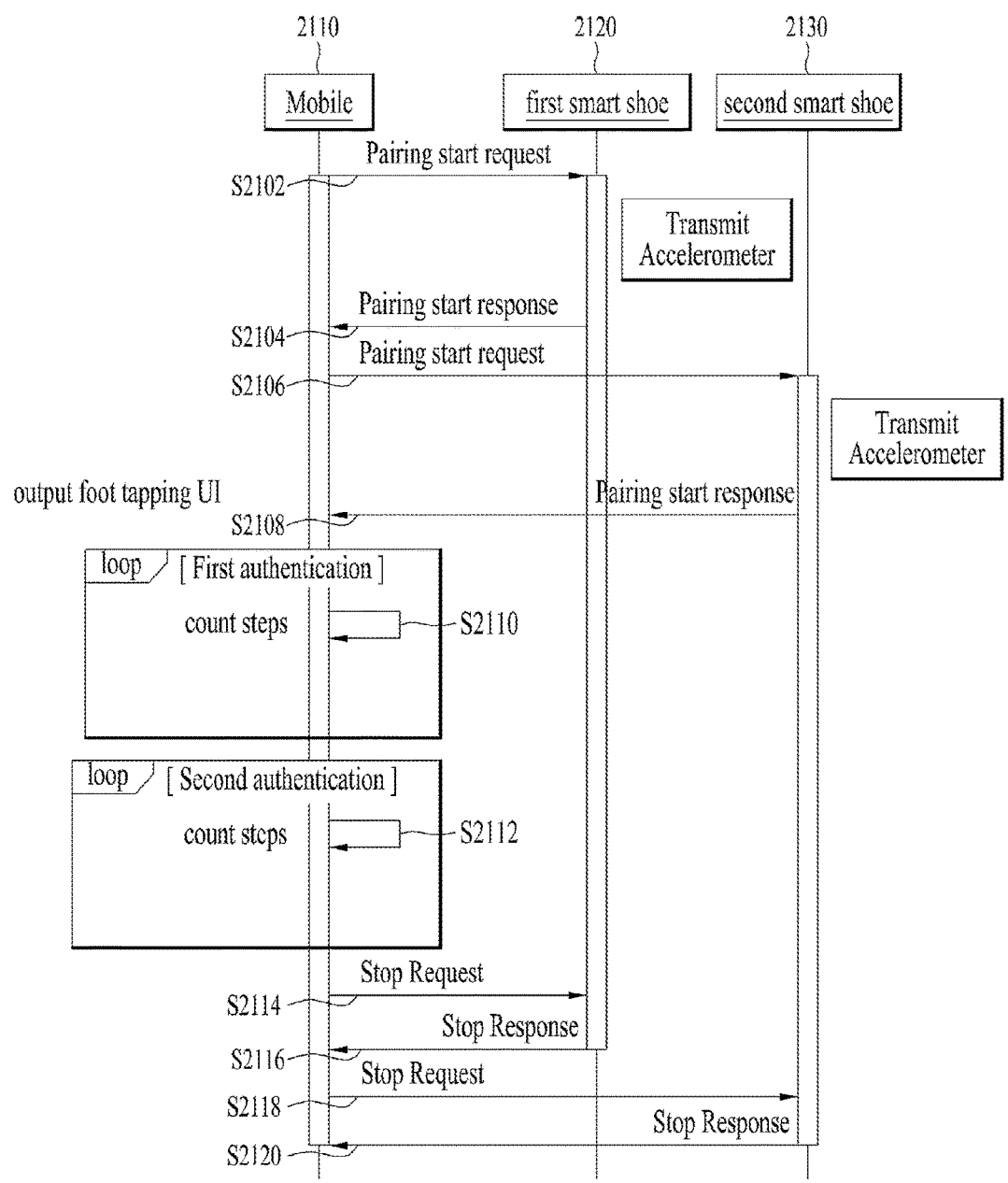
FIGS. 21 and 22 are sequence diagrams illustrating a procedure of automatically pairing smart shoes and a plurality of mobile terminals in accordance with one embodiment of the present invention.
Figure 22:
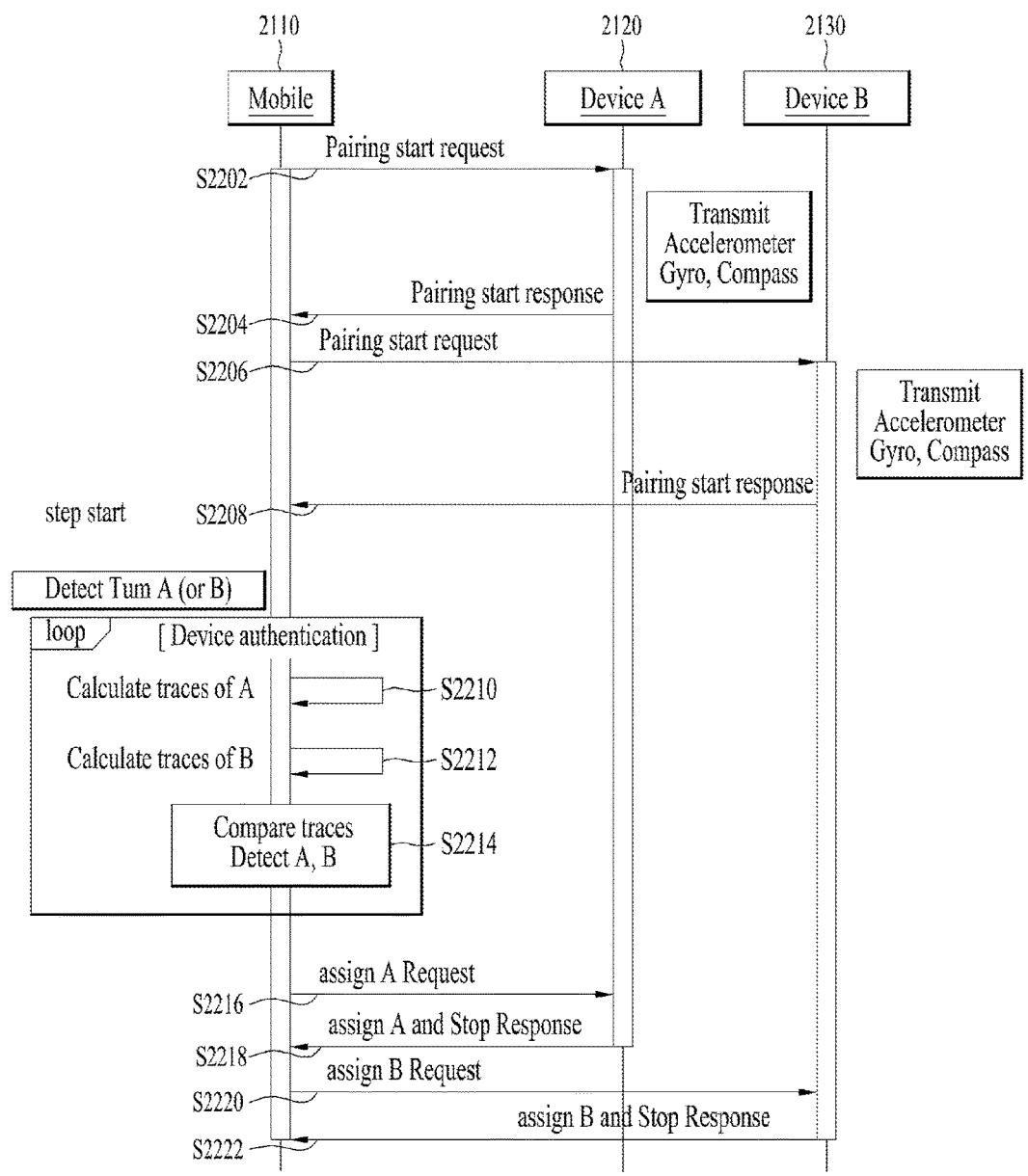

FIGS. 21 and 22 are sequence diagrams illustrating a procedure of automatically pairing smart shoes and a plurality of mobile terminals in accordance with one embodiment of the present invention.

For example, FIG. 21 illustrates a pairing procedure through a gesture between the mobile terminal and the smart shoes provided with a 3-axis sensor, and FIG. 22 illustrates a pairing procedure through a gesture between the mobile terminal and the smart shoes provided with a 9-axis sensor.

First of all, the pairing procedure through a gesture between the mobile terminal 2110 and the first and second smart shoes 2120 and 2130 will be described in more detail with reference to FIG. 21. At this time, the first smart shoe 2120 indicates a left (L) smart shoe that includes a 3-axis based smart shoes sensor module, and the second smart shoe 2130 indicates a right (R) smart shoe that includes a 3-axis based smart shoes sensor module.

The mobile terminal 2110 transmits a pairing start request signal to the first smart shoe 2120 (S2102). At this time, the first smart shoe 2120 enables the pairing start request signal of the mobile terminal 2110 by transmitting the pairing start request signal to the sensor module. The first smart shoe 2120 returns a pairing start response signal in response to the pairing start request signal of the mobile terminal 2110 (S2104). Generally, the returning pairing start response signal of the first smart shoe 2120 includes a response that agrees to the pairing start request.

Then, the mobile terminal 2120 transmits a pairing start request signal to the second smart shoe 2130 (S2106). At this time, the second smart shoe 2130 enables the pairing start request signal of the mobile terminal 2110 by transmitting the pairing start request signal to the sensor module. The second smart shoe 2130 returns a pairing start response signal in response to the pairing start request signal of the mobile terminal 2110 (S2108).

The steps S2102 to S2104 or the steps S2106 to S2108 are performed if the smart shoes sensor module is mounted in the corresponding shoe. Therefore, if the sensor module is mounted in both the smart shoes, all the steps S2102 to S2108 are performed. However, if the sensor module is mounted in any one smart shoe, either the steps S2102 to S2104 or the steps S2106 to S2108 may be performed. Also, the order of the steps S2102 to S2104 or the steps S2106 to S2108 may be different from the shown order.

The aforementioned steps S2102 to S2108 are connection steps for pairing, and may be regarded as pairing initial steps.

In this way, after the pairing initial steps are performed, the mobile terminal 2110 provides the UX shown in FIG. 19 or 20 to attempt pairing with the smart shoes.

In more detail, the mobile terminal 2110 performs an authentication procedure with the first smart shoe 2120. Referring to FIG. 20, this authentication procedure is performed through tapping foot of the smart shoes wearer with respect to the first smart shoe as much as the number of given times. At this time, the mobile terminal 2110 counts the number of times for tapping foot of the first smart shoe 2120 (S2110), and authenticates the corresponding smart shoe if tapping foot reaches the given count times. At this time, this step may be performed repeatedly in the form of loop until authentication is successfully performed.

Meanwhile, if authentication is failed a predetermined number of times or more or is not successfully performed within a predetermined time, the authentication procedure may be reset and then return to the pairing initial step or execution of the application for pairing on the mobile terminal 2110 may end.

The authentication procedure of the mobile terminal 2100 with respect to the first smart shoe 2120 is performed equally with respect to the second smart 2130.

If the pairing authentication procedure for both the smart shoes is completed through the steps S2110 and S2112, the mobile terminal 2110 transmits a pairing step request signal to each of the smart shoes 2120 and 2130 (S2114, S2118), and receives a response signal to the pairing step request signal from each of the smart shoes 2120 and 2130 (S2116, S2120).

Through the aforementioned procedure, the pairing procedure is completed, and data communication between the mobile terminal 2110 and the smart shoes 2120 and 2130 is performed.

Meanwhile, the procedure shown in FIG. 21 is not limited to the shown order. For example, the steps S2106 to S2108 may be performed after the step S2110 or the step S2114.

Next, the pairing procedure through a gesture between the mobile terminal 2110 and the first and second smart shoes 2120 and 2130 will be described in more detail with reference to FIG. 22. At this time, the first smart shoe 2120 indicates a left (L) smart shoe that includes a 9-axis based smart shoes sensor module, and the second smart shoe 2130 indicates a right (R) smart shoe that includes a 9-axis based smart shoes sensor module.

Since the procedure of FIG. 22 is the same as the pairing initial step between the mobile terminal 2110 and the smart shoes 2120 and 2130 in FIG. 21, its repeated description will be omitted. However, sensors enabled based on the 9-axis sensor at the pairing initial step of FIG. 22 may be more than those enabled based on the 3-axis sensor at the pairing initial step of FIG. 21.

Meanwhile, after the pairing initial step in FIG. 22, the pairing authentication step is different from that of FIG. 21. For example, the mobile terminal 2110 provides an authentication UX and thus receives a gesture input of the smart shoe in FIG. 21, whereas an authentication procedure different from that of FIG. 21 is used in FIG. 22. In other words, the mobile terminal 2110 detects at least one of the first smart shoe 2120 and the second smart shoe 2130 (S2210).

The mobile terminal 2110 authenticates the detected smart shoe. At this time, it is assumed that the first smart shoe 2120 and the second smart shoe 2130 have been detected. The mobile terminal 2110 calculates traces of the first smart shoe 2120 (S2212), and equally calculates traces of the second smart shoe 2130 (S2214). The mobile terminal 2110 compares the calculated traces of the first smart shoe 2120 with the calculated traces of the second smart shoe 2130 (S2216). In this case, the mobile terminal 2110 may compare a trace calculate value of each smart shoe, which is previously stored in the mobile terminal 2110 (or server, etc.) with the trace calculated value of each smart shoe, which is calculated through the steps S2212 and S2214, to perform authentication. However, the present invention is not limited to this case, and may use various targets, which may recognize or authenticate each smart shoe, in respect of the comparison.

As a result of the step S2216, if authentication of at least one of the smart shoes is failed, the mobile terminal 2110 may again perform the aforementioned authentication procedure for the corresponding shoe or both the smart shoes. In other words, the authentication procedure may be performed repeatedly in the form of a loop structure. Meanwhile, this repetition may be performed for a predetermined number of times, or may be re-performed by resetting the pairing procedure for the smart shoe of which authentication is finally failed or both the smart shoes.

As a result of the step S2216, if each smart shoe is authenticated, the mobile terminal 2110 advances to next procedure. Referring to FIG. 22, the mobile terminal 2110 transmits a 'LEFT' request allocation signal to the first smart shoe 2120 (S2218), and the first smart shoe 2120 returns a 'LEFT and Stop' response allocation signal (S2220). A request-response procedure of the first smart shoe is performed equally even with respect to the second smart shoe (S2222, S2224).

Through the aforementioned procedure, the pairing procedure between the mobile terminal 2110 and the smart shoes 2120 and 2130 provided with a 9-axis sensor may be completed, and after the pairing procedure is completed, data communication may be performed.

The pairing procedure between the smart shoes provided with the 3-axis sensor and the mobile terminal and the pairing procedure between the smart shoes provided with the 9-axis sensor and the mobile terminal in FIGS. 21 and 22 are only exemplary, and are not limited to the shown sequences. Also, each sequence of the paring procedures shown in FIGS. 21 and 22 may not be an essential sequence. At least one sequence may be omitted or skipped, whereas at least one sequence may be added depending on system or status.

The steps of the first smart shoe 2120 and the second smart shoe 2130 in the steps shown in FIG. 21 may be performed in reverse order. For example, in FIG. 21 the first smart shoe 2120 accesses the mobile terminal prior to the second smart shoe 2130, or vice versa. This may equally be applied to FIG. 22.

Meanwhile, in this specification, it is assumed that the sensor module is mounted in each of both the smart shoes. However, as shown in FIGS. 21 and 22, it is not required that pairing initialization and pairing authentication should be performed for both the smart shoes. For example, if the pairing procedure is completed with respect to any one smart shoe, the other smart shoe may be paired automatically as a set or pair without authentication. If an error or problem occurs during later data communication, authentication may newly be performed or re-authentication may be performed.

Hereinafter, in this specification, seamless data communication between smart terminals will be described. In this case, examples of the smart terminals include all terminals, which enable data communication through wire/wireless communication means, such as smart phones, tablet PCs, wearable devices, PCs, laptop computers, and digital TVs. For convenience of description, in this specification, at least one reference smart terminal and one or more smart shoes will be described. However, the smart terminal is not limited to the above examples.

Meanwhile, in this specification, the data communication procedure between the smart terminals is performed using data compression in accordance with various references. The data compression may be one example for implementing low power required in the smart terminals as well as enhancing system efficiency by reducing the time required for the data communication. Also, the present invention is intended to enhance convenience of smart terminal users and production purchase desire by providing a user interface, which is intuitive and has high visibility, on the basis of data acquired through data communication between the smart terminals.

Hereinafter, data communication between the smart terminals will be described in more detail with reference to the accompanying drawings. It is assumed that the smart terminals are basically registered in each other with reference to at least one of FIGS. 19 to 22.

Referring to FIGS. 13 to 18, movement data for indoor activity of the user who wears the smart shoes may be acquired, and various kinds of information may be provided by analyzing movement of the user based on the acquired movement data. Although outdoor activity of the user may be understood with reference to the embodiments of FIGS. 13 to 18, it is difficult to exactly calculate outdoor activity of the user with reference to only the embodiments of FIGS. 13 to 18. Therefore, hereinafter, various embodiments for providing information on the result of acquisition and analysis of movement data during outdoor activity of the smart shoes wearer will be described.

Particularly, in the present invention, GPS data may be used for data acquisition and analysis during outdoor activity of the smart shoes wearer. Especially, the GPS data include GPS velocity data. However, since the GPS data may have an error due to various GPS receiving conditions such as time, place and weather, if outdoor activity data of the smart shoes wearer are acquired by the GPS data only, an error may occur. Therefore, the present invention is intended to correct an error of the GPS data and more exactly calculate movement data of the user with reference to pressure sensor data acquired through the pressure sensor in the sensor module of the smart shoes according to the present invention together with the GPS data.

Figure 23:
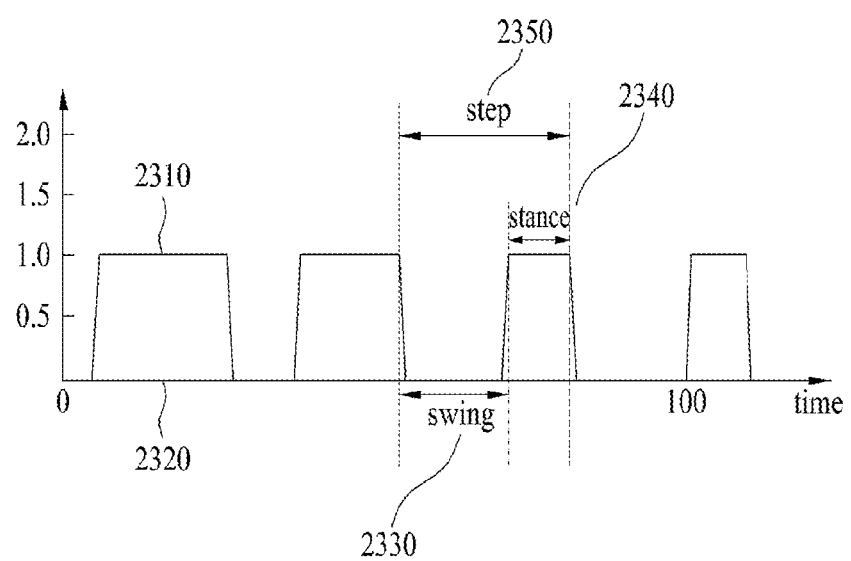
FIG. 23 is a graph illustrating smart shoes pressure sensor data related to the present invention.

FIG. 23 is a graph illustrating smart shoes pressure sensor data related to the present invention.

Referring to the graph of FIG. 23, a horizontal axis indicates a time, and a vertical axis indicates a pressure. In this case, the pressure of the vertical axis may be a pressure value sensed through the pressure sensor in the sensor module provided in the smart shoes. However, for convenience, in the present invention, the pressure of the vertical axis may be categorized into a case (1, 2310) having a pressure and a case (0, 2320) having no pressure in respect of movement data sensing.

Also, referring to FIG. 23, a swing interval 2330 is between off timing and on timing, a stance interval 2340 corresponds to on timing, and a step interval 2350 is between off timing and next off timing (or between one time and next on timing). In this case, the step interval 2350 corresponds to a plus interval of the swing interval 2330 and the stance interval 2340.

In the present invention, walking velocity of the user may be calculated from the graph of FIG. 23. The walking velocity may be calculated from correlation between actual waling velocity of the user and frequency of step from the graph of FIG. 23. In this case, frequency of step may mean at least one of a step rate (SR) and a swing/stance ratio (SSR).

Meanwhile, walking velocity of the user may be calculated even through FIG. 24 as well as data sensed from the pressure sensor of the smart shoes as shown in FIG. 23.

FIG. 24 is a GPS data graph according to the present invention. In this case, a horizontal axis may indicate a time, and a vertical axis may indicate a velocity.

In the drawings for description of the present invention, dots indicate GPS velocity data and sensor velocity data of the smart shoes and are obtained by receiving or calculating the GPS velocity data and the sensor velocity data at a predetermined time unit. For example, the predetermined time may be 5 seconds, or may be longer or shorter than 5 seconds. Meanwhile, it is not required that the timing for acquiring the GPS velocity data should be the same as the timing for acquiring sensor velocity data. However, it is preferable that the data of the same timing are used for convenience such as velocity data correction.

FIGS. 24*a* and 24*b* illustrate GPS velocity data graphs, and FIG. 24*c* illustrates a GPS Data GUI configured with reference to FIG. 24*a* or 24*b*.

Particularly, FIG. 24*a* illustrates that GPS reception is good, and FIG. 24*b* illustrates that GPS reception is not good.

Referring to data graphs of FIGS. 24*a* and 24*b*, sensor velocity data 2414 and 2424 based on sensing data of the pressure sensor of the smart shoes as well as GPS velocity data 2412 and 2422 are provided.

Meanwhile, referring to the vertical axis, that is, velocity, in the data graphs, it is noted that the GPS velocity data 2412 to the sensor velocity data 2414 have a similar data graph when GPS reception is good in FIG. 24*a*. However, it is noted that the GPS velocity data 2422 to the sensor velocity data 2424 have a very great deviation when GPS reception is not good in FIG. 24*b*. Therefore, if GPS velocity data of FIG. 24*b* are used as they are, an error may occur, whereby calibration may be required. This will be described in detail later.

In addition, FIG. 24*c* illustrates GUI that includes a trace of a user based on GPS data received on a GPS map. In this case, the GPS velocity may be calculated from data intervals 2432 and 2434 within the GUI. For example, the GPS velocity may be calculated from distance/time between the GPS data intervals 2432 and 2434. Each dot within the GUI may indicate a position of the GPS data received at a predetermined time unit.

The present invention may provide personalized services with reference to sensor velocity data sensed through the pressure sensor of the smart shoes and GPS velocity data.

FIG. 25 illustrates filtering technique for GPS velocity calibration in accordance with one embodiment of the present invention.

In the present invention, GPS velocity data are basically used as a reference, and if an error occurs in reliability of the GPS velocity data, the error may be filtered and calibrated with reference to sensor data of the smart shoes.

If it is apparent that an error occurs in the GPS velocity data, the error may be removed simply. However, it may not be easy to detect and remove the error of the GPS velocity data. If the GPS velocity data determined as an error is continuous or repeated, filtering of the corresponding interval may affect reliability of whole data. Therefore, the present invention is intended to calibrate GSP velocity by appropriately filtering an error at a point where the error occurs with reference to sensor velocity data acquired through the smart shoes while using whole GPS velocity data received through a GPS receiving unit provided in the smart terminal (or smart shoes) instead of simply removing GPS velocity data corresponding to the aforementioned error. Meanwhile, the present invention is characterized in that filtering common for all smart shoes is used and performed based on data personalized to be suitable for a user who wears the smart shoes.

A filtering/calibrating method used for data calibration in accordance with the present invention may be described based on equations shown in FIG. 25.

FIG. 25a illustrates a basic filtering equation. Referring to FIG. 25a, both velocity data (for convenience, sensor velocity) Velocitysensor of the smart shoes sensor and GPS velocity data Velocitygps are used. At this time, the filtering is performed with reference to the sensor speed data and the GPS speed data, and in this case, a weight value W is given to each data. A weight value 2510 of the sensor velocity data may be different from a weight value 2520 of the GPS velocity data.

Referring to FIG. 25a, for example, the weight value 2510 of the sensor velocity data is Wgps/(Wsensor+Wgps), and the weight value 2520 of the GPS velocity data is Wsensor/(Wsensor+Wgps). In other words, numerators Wgps and Wsensor of the weight value are arranged at a mutual reverse value such that the weight value becomes greater if an error becomes smaller, by minimizing an effect according to the GPS velocity data. Therefore, the weight value may be given to the sensor velocity data and the less weight value may be given to the GPS velocity data even in the case that the GPS velocity is increased unexpectedly. As a result, it may contribute to GPS velocity calibration through filtering.

In respect of the weight value, Wgps is shown in FIG. 25b as an example of an equation thereof, and Wsensor is shown in FIG. 25c as an example of an equation thereof. If this weight value becomes greater, reliability may be lowered. Basically, if the velocity deviation becomes smaller, values of the Wgps and the Wsensor become smaller. Also, GPS may be used by definition of parameters p1 and p2 so that the above values may be controlled in accordance with a receiving environment and reflected in the form of exponentiation to reference accuracy.

However, the equations shown in FIG. 25 are embodiments of the present invention, and the scope of the present invention is not limited to the equations of FIG. 25. Various equations or methods for GPS velocity data filtering or calibration based on sensor data according to the present invention also pertain to the scope of the present invention.

In the present invention, filtering/calibration of the GPS velocity data based on the equations of FIG. 25 frequently causes the possibility of an error in the GPS velocity data or a problem in reliability of the GPS velocity data. For example, GPS data may be jumped unexpectedly, a GPS angle may be changed, or GPS velocity data may be jumped unexpectedly from zero (0). Also, if the user who wears the smart shoes continues to perform outdoor activity, the case that GPS reception is good and the case that GPS reception is not good may be repeated due to various environmental factors such as time and position. However, regardless of reliability of GPS data, the present invention is characterized in that data may be supplied stably even in the case that GPS data reception is good or not when the user intends to use GPS velocity data.

Figure 26:
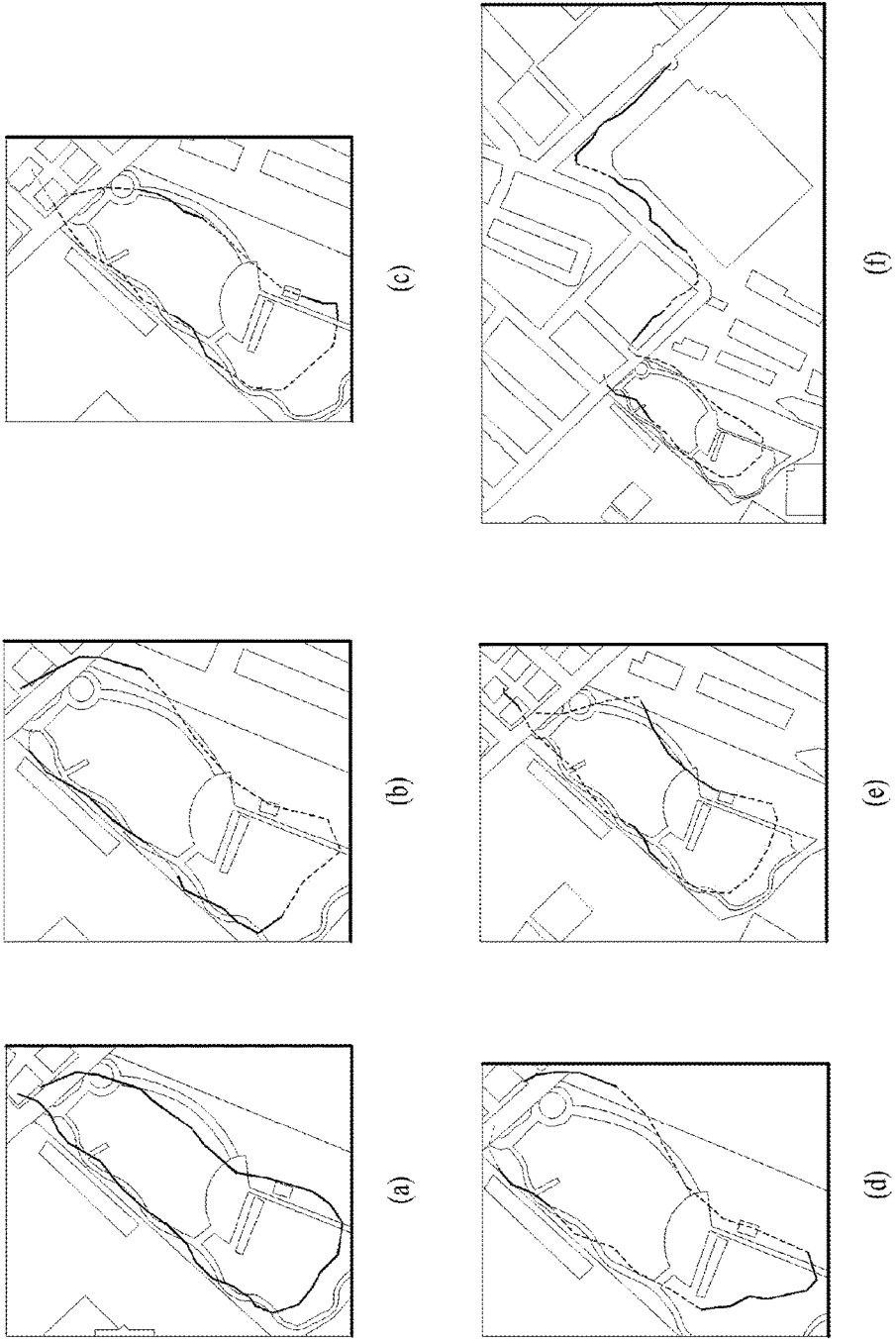
FIGS. 26 to 28 are views illustrating filtering results when reception of GPS data is good in accordance with one embodiment of the present invention.
Figure 27:
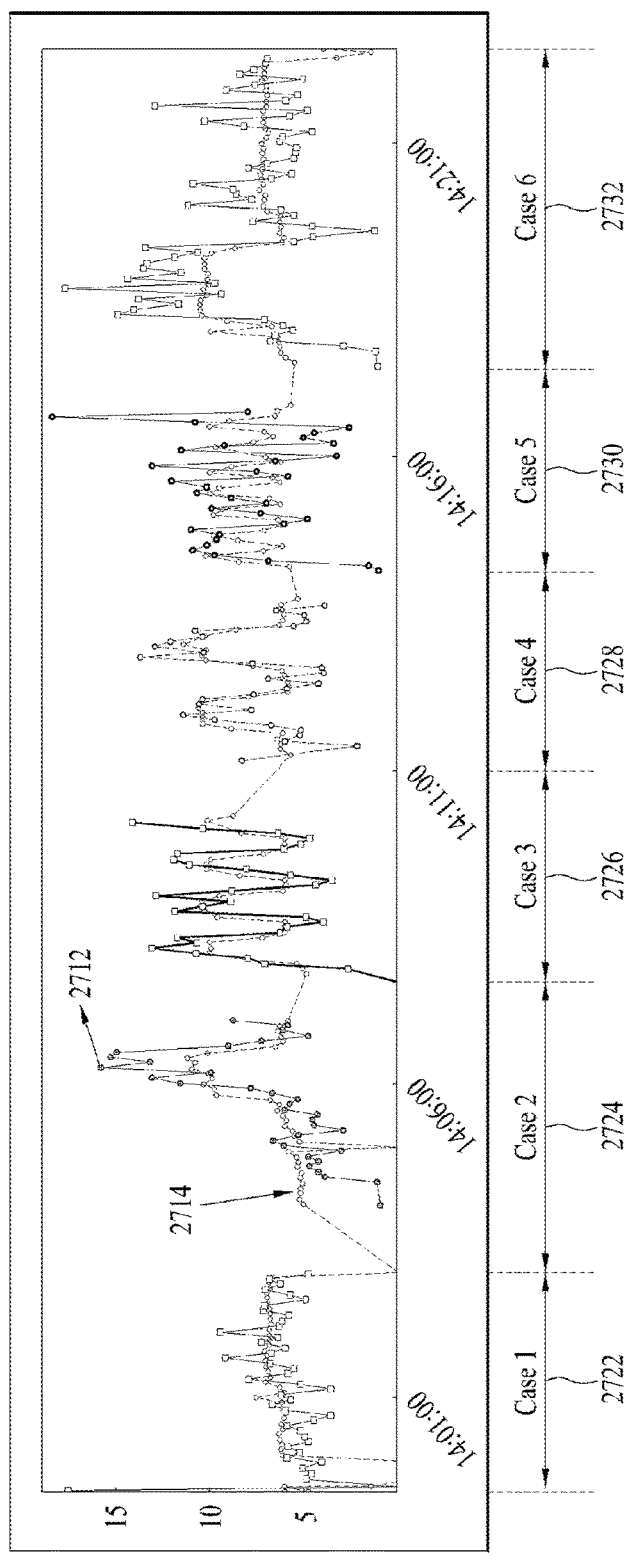
Figure 28:
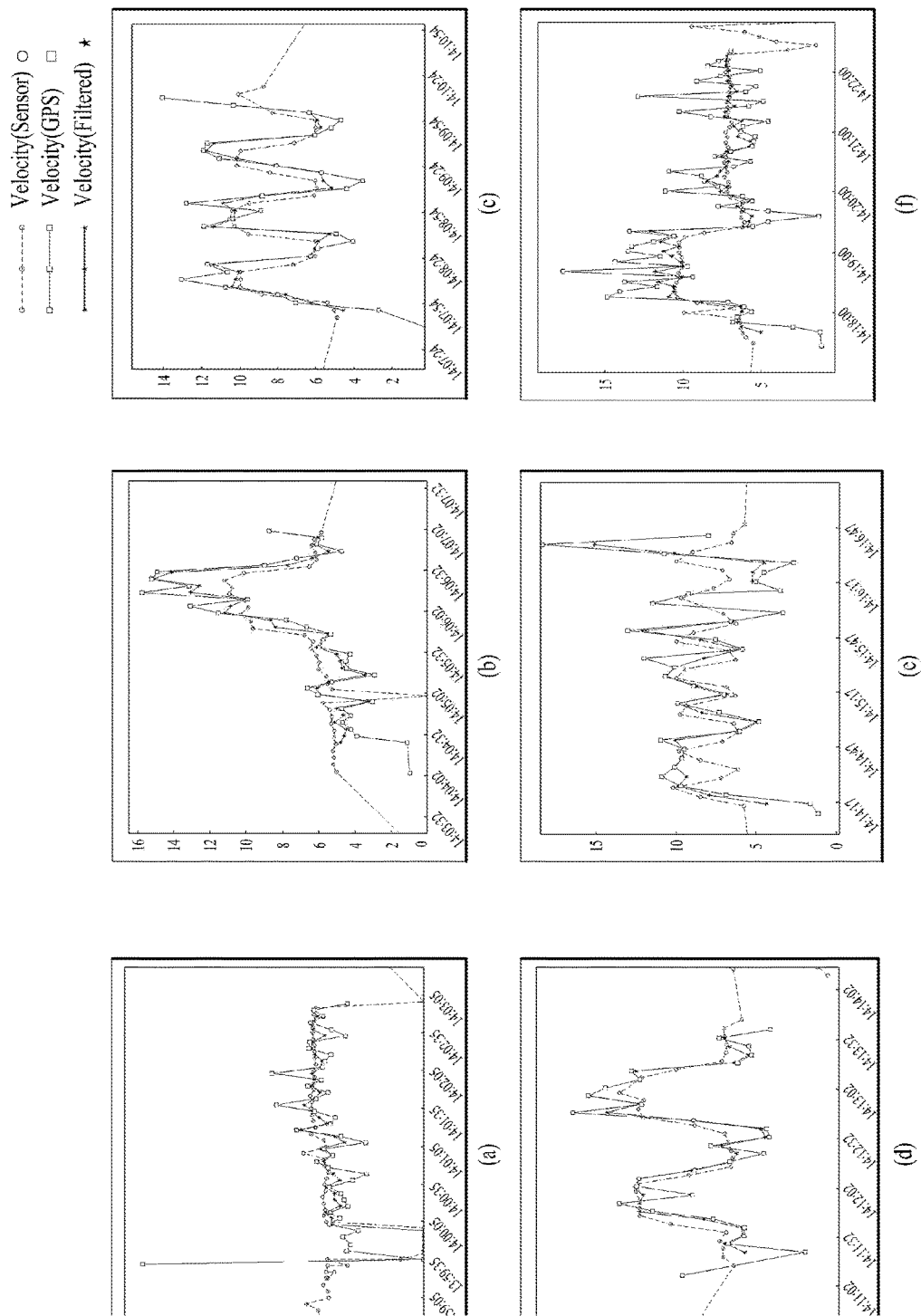

FIGS. 26 to 28 are views illustrating filtering results when reception of GPS data is good in accordance with one embodiment of the present invention.

FIGS. 26a to 26f illustrate movement of a user who wears smart shoes on a GPS map. Meanwhile, FIG. 27 illustrates a graph for GPS velocity data per time and sensor velocity data of smart shoes. In this case, a horizontal axis of FIG. 27 indicates a time, and a vertical axis thereof indicates a velocity. At this time, FIGS. 26a to 27f respectively correspond to case 1 to case 6 (2722 to 2732) of FIG. 27 in due order. In the data graph of FIG. 27, a line 2712 for connecting square shaped dots indicates GPS velocity data, and a line 2714 for connecting circular shaped dots indicate sensor velocity data sensed through the pressure sensor of the smart shoes. Meanwhile, FIGS. 28a to 28f illustrate movement of the user who wears smarts shoes on a GPS map as described above. In this case, a line for connecting star shaped dots means filtered velocity data or filtered GPS velocity data.

FIGS. 26 and 27 illustrate that GPS data reception is good as described above. In this case, movement data of the smart shoes wearer may be configured and analyzed based on the GPS velocity data. However, as described above, if the filtering scheme according to the present invention of FIG. 25 is used even though GPS data reception is good, it is noted that a movement data graph more improved than that of FIG. 27 may be acquired in FIG. 28.

Referring to FIGS. 26 and 27, it is noted that a velocity fluctuation range of the GPS velocity data for an interval of case 1 (2722) is smaller and constant than that of the sensor velocity data and a user moves at a certain velocity. Therefore, it is noted from the GPS velocity data and the sensor velocity data that the smart shoes wearer moves at a certain range for the interval of case 1 (2722). However, referring to velocity values, it may be inferred that the smart shoes wearer walks at a certain velocity for the corresponding interval 2722.

For an interval of case 2 (2724), the GPS velocity data form two kinds of patterns, which have a certain fluctuation range near a first velocity at the first of the corresponding interval and then have a certain fluctuation range near a second velocity. Likewise, it is noted that the sensor velocity data have a first velocity at the first of the corresponding interval, and then have a second velocity. Referring to velocity values in the graph of FIG. 27, the first velocity corresponds to a walking velocity, and a second velocity faster than the first velocity may be determined as a velocity faster than walking, that is, a running velocity. In short, for the interval of case 2 (2724), it may be construed that the user walks and then runs.

An interval of case 3 (2726) indicates that the GPS velocity data are repeated between the first velocity and the second velocity and the sensor velocity data are also repeated between the first velocity and the second velocity. This pattern of the velocity data may be regarded that the smart shoes wearer performs interval running. That is, this interval may be regarded as an interval where walking and running are repeated at a predetermined time interval.

An interval of case 4 (2728) indicates a velocity data graph pattern similar to that of the aforementioned case 3 (2726), and may be regarded as an interval where walking and running are repeated. However, it is noted that the number of times or frequency for repetition of walking and running in this case 4 is higher than that of the case 3 (2726). That is, the case 3 (2726) indicates interval movement of the smart shoes wearer at a short time unit, whereas the case 4 (2728) indicates interval movement of the smart shoes wearer at a relatively longer time unit than the case 3 (2726).

An interval of case 5 (2730) indicates a velocity data graph pattern similar to those of the case 3 (2726) and the case 4 (2728), and may be regarded as an interval where walking and running are repeated. However, it is noted that the number of times or width for velocity fluctuation in this case 5 is greater than that of each of the cases 3 and 4. Therefore, the interval of the case 5 (2730) indicates interval movement of the smart shoes wearer at a shorter time unit than that of each of the case 3 (2726) and the case 4 (2728).

Finally, an interval of case 6 (2732) indicates various velocity data graph patterns. That is, referring to velocity fluctuation through the GPS velocity data and the sensor velocity data, it is noted that the smart shoes wearer first walks and then runs and again walks. However, the interval of the case 6 (2732) has a velocity data pattern different from those of the case 3 to the case 5 (2726 to 2730), that is, velocity data pattern of interval movement. Meanwhile, the interval of the case 6 (2732) may be regarded as a walking interval in view of a velocity value, but may have a velocity faster than that of the interval of the case 1 (2722). This may be inferred that the smart shoes wearer walks at a faster step than a normal step.

Meanwhile, walking, fast walking, running, and interval may be identified by comprehensive determination of values such as GPS velocity data fluctuation, sensor velocity data fluctuation, fluctuation width, fluctuation size, and velocity for the interval of the case 1 to the case 6 (2722 to 2732). Also, this identification may calculate personalized data with reference to SR, SSR, etc. of the smart shoes wearer of FIG. 24. This identification may be performed more exactly considering age, sex, movement capability of the user.

Referring to FIG. 27, since the GPS velocity data and the sensor velocity data for each interval have certain type patterns, it may be regarded that GPS reception is good or the possibility of an error of the GPS velocity data is relatively low. However, a start point of each interval such as a start point of the interval of the case 1 (2722) or a jump interval of GPS velocity data such as an end point of the case 5 (2730) exists, whereby data different from the aforementioned movement pattern analysis of the smart shoes wearer may be received. The GPS velocity jump data may be disregarded but may cause a great error under a specific status. Therefore, as described above, even though GPS data reception is good, filtering may be required. This is because that an error may occur like the case that GPS data are not received unexpectedly, and this event may always occur considering properties of GPS data affected by various surrounding environments.

FIGS. 28a to 28f correspond to the intervals of the case 1 to the case 6 (2722 to 2732) of FIG. 27, and illustrate data graphs that include velocity data filtered using the method of FIG. 25.

Meanwhile, in FIGS. 28a to 28f, a horizontal axis, that is, a time axis is more subdivided than that of FIG. 28 to easily determine a filtering effect of the GPS velocity data.

As described above, if the time axis is divided into a shorter time unit to show the GPS velocity data and the sensor velocity data, it is noted that there is a difference between the GPS velocity data and the sensor velocity data at some timing points in each of FIGS. 28a to 28f. Therefore, if the data of the above timing points are not filtered in accordance with the method of FIG. 25 according to the present invention, it may affect data shortly before or after the points and also affect reliability of data. In the present invention, the above timing points may be filtered in accordance with the present invention, and all the corresponding intervals may be filtered even in case of the timing points. In FIG. 28, it is noted that data reliability is not affected by even at least one of the above timing points as all the corresponding intervals are filtered. Therefore, if GPS velocity data calibration according to the above filtering scheme is used, a movement pattern of the smart shoes wearer may be predicted exactly.

FIGS. 29 to 33 are views illustrating filtering results when reception of GPS data is not good in accordance with one embodiment of the present invention.

Unlike FIGS. 26 to 28, velocity data filtering in an environment that GPS data reception is not good relatively will be described with reference to FIGS. 29 to 33.

FIGS. 29 to 33 illustrate data graphs that include GPS velocity data, sensor velocity data, and filtered velocity data. In this case, a line connecting circular shaped dots indicates sensor velocity data, a line connecting square shaped dots indicates GPS velocity data, and a line connecting star shaped dots indicates filtered velocity data.

Figure 29:
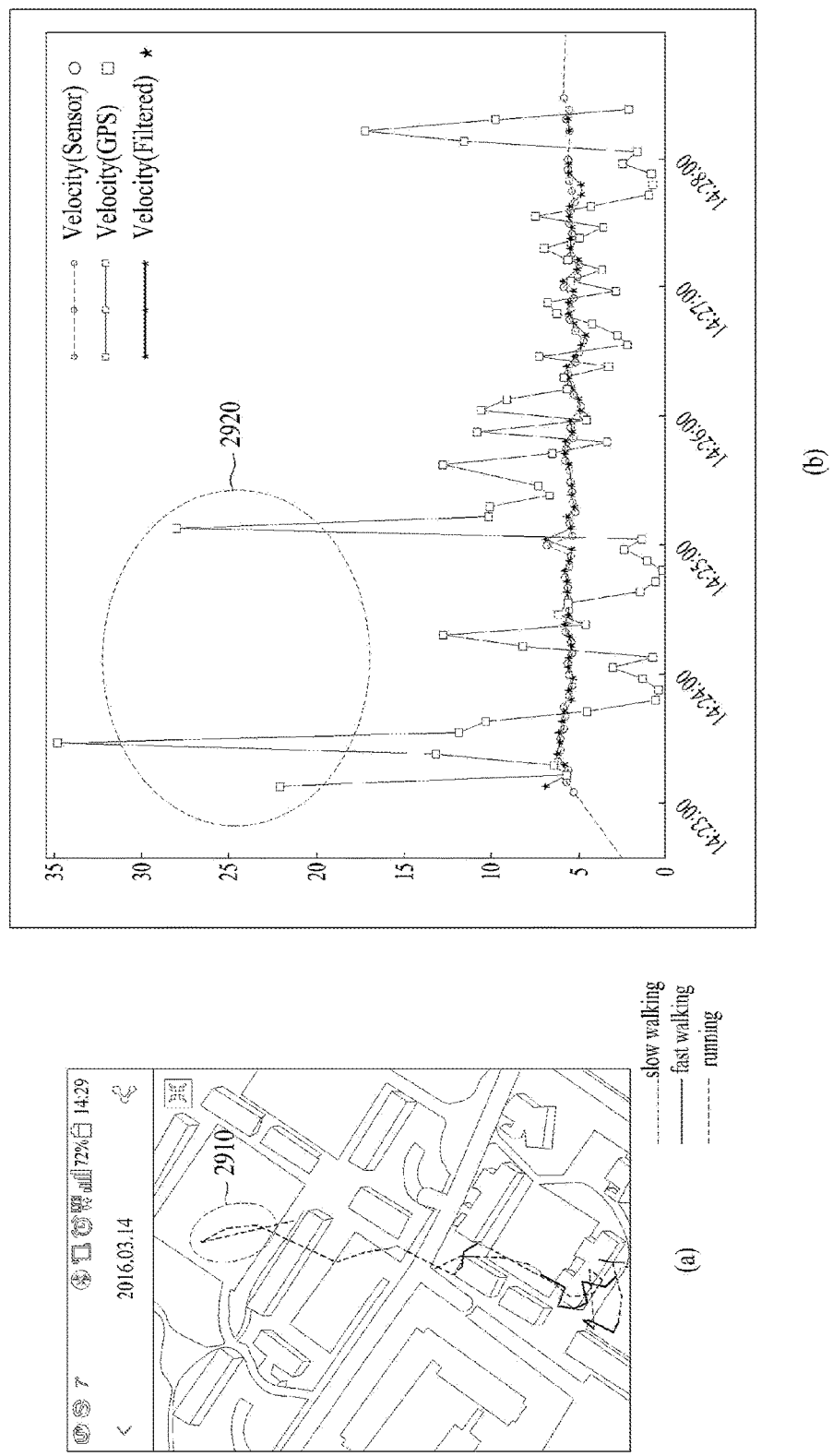
FIGS. 29 to 33 are views illustrating filtering results when reception of GPS data is not good in accordance with one embodiment of the present invention.
Figure 30:
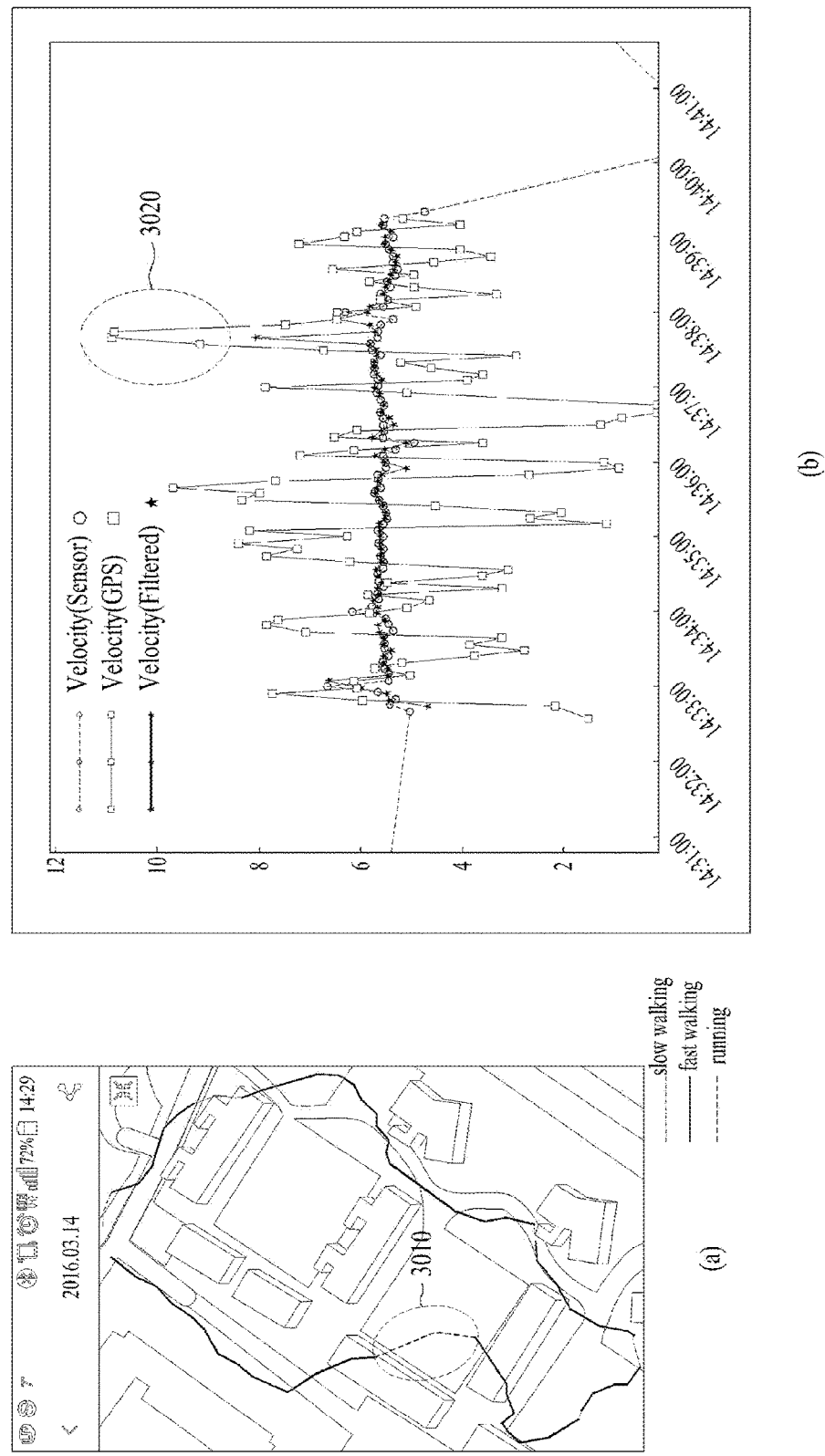
Figure 31:
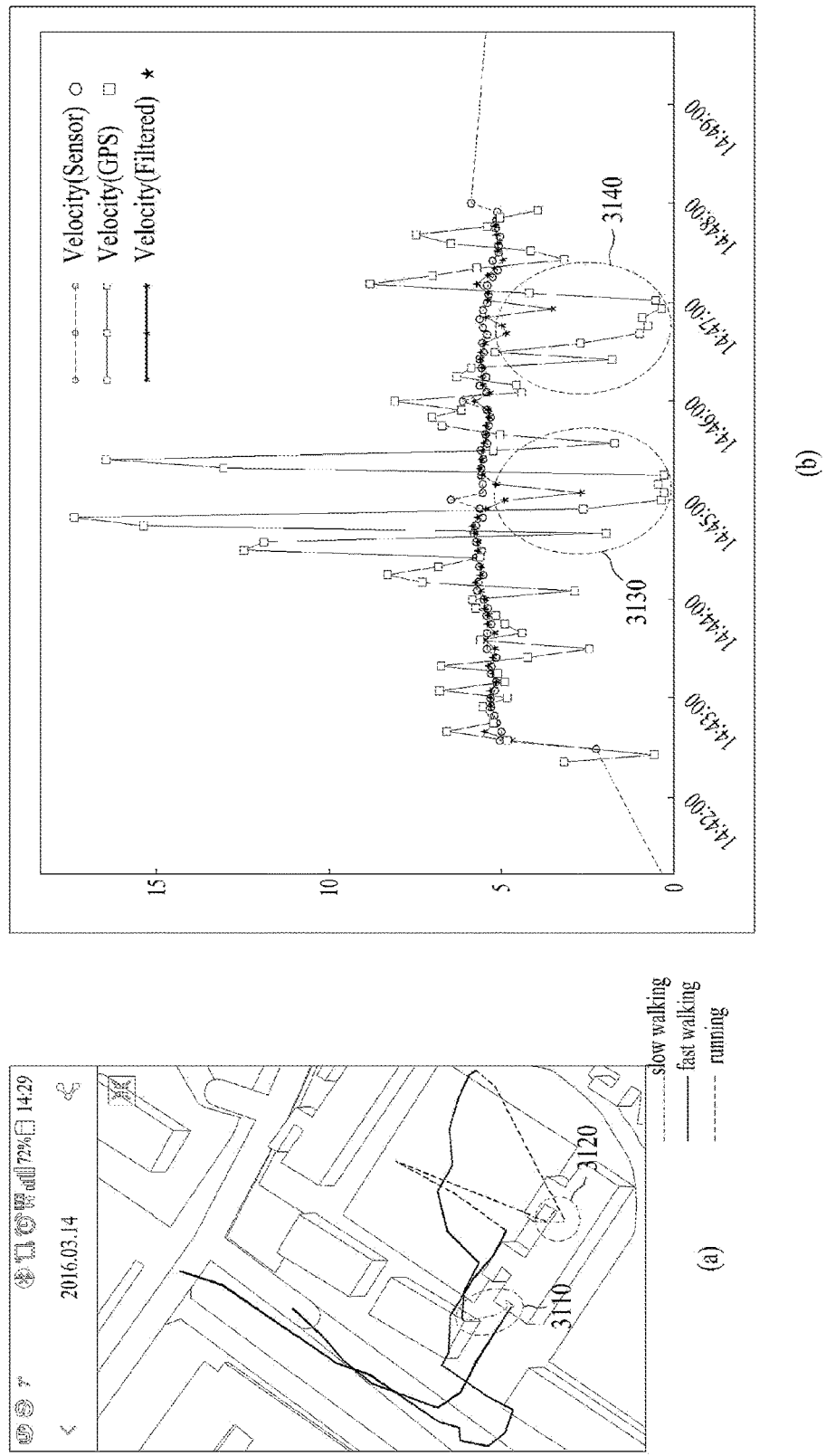
Figure 32:
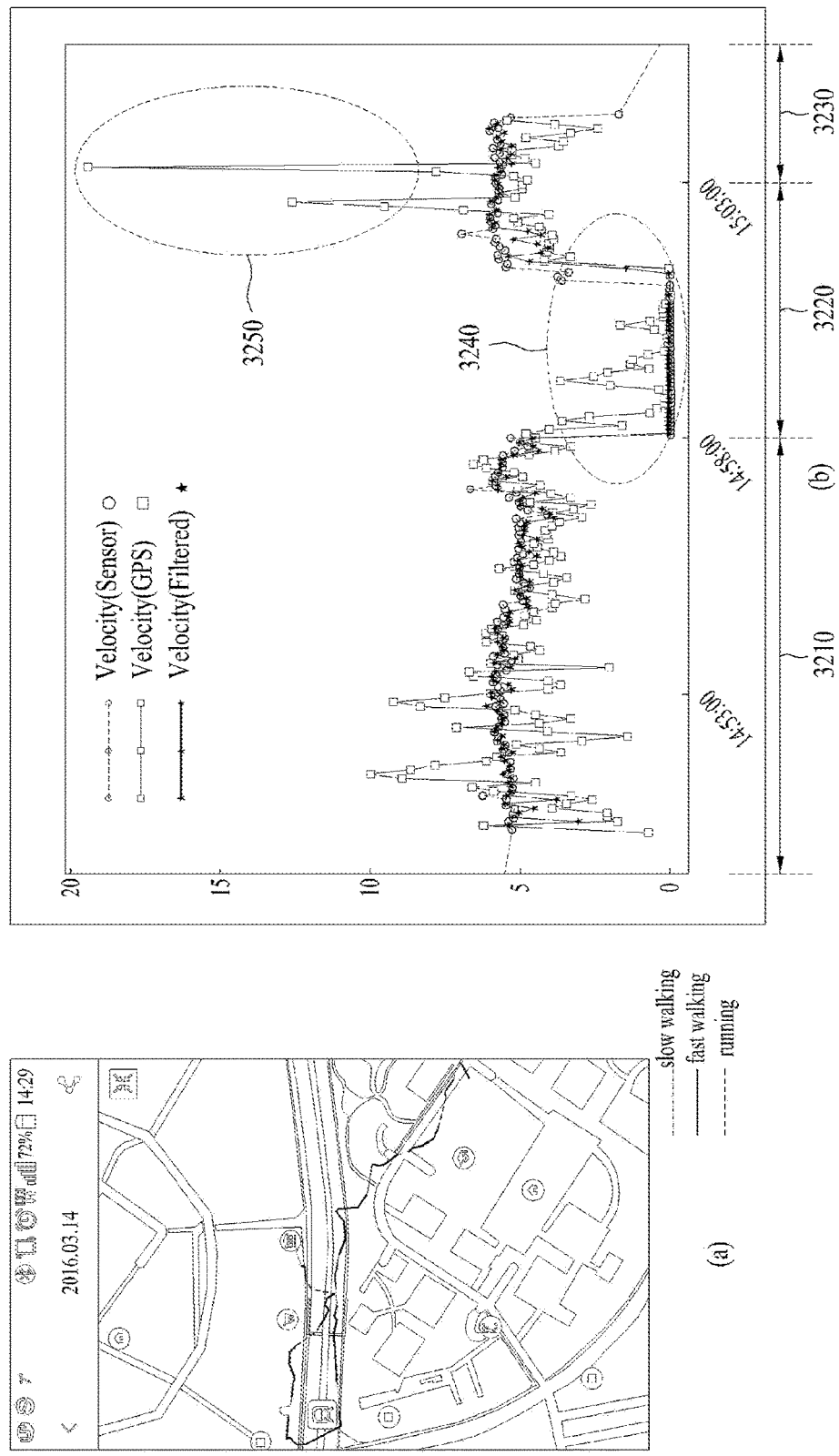
Figure 33:
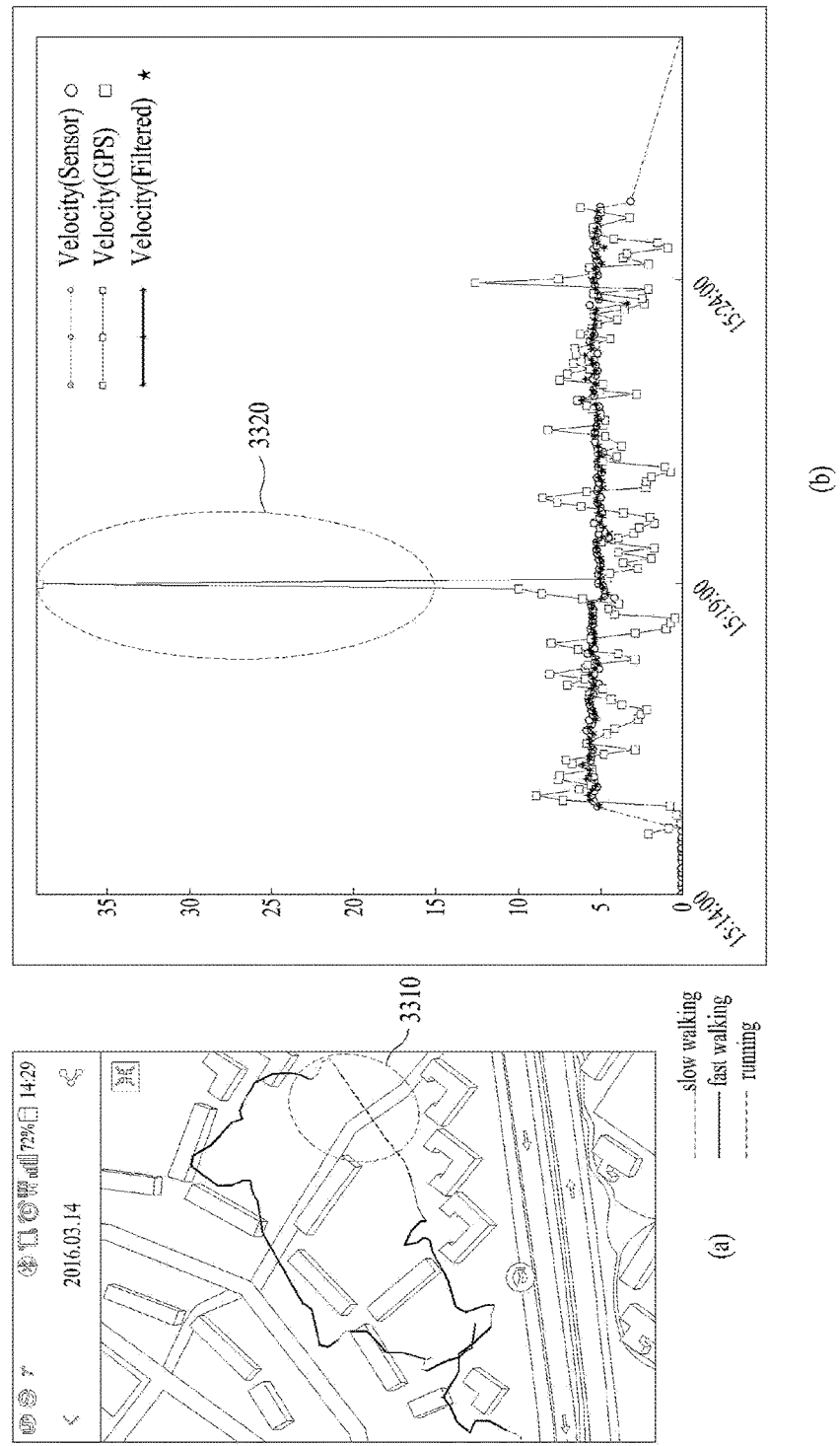

Particularly, referring to sensor velocity data in FIGS. 29 to 31, it is noted that the user who wears smart shoes moves at a certain velocity within a time interval of each graph.

First of all, FIG. 29a illustrates that movement of a user who wears smart shoes on a GPS map is shown as a GUI, and FIG. 29b illustrates a velocity data graph corresponding to the GUI of FIG. 29a.

Referring to sensor velocity data of FIG. 29b, it is noted that the user who wears smart shoes continues to walk at a certain velocity on the map of FIG. 29a from 14:23:00 to 14:28:00. That is, three is little change of velocity.

However, referring to GPS velocity data, it is noted that GPS velocity data of a point 2920 of FIG. 29b corresponding to a point 2910 of FIG. 29a have a pattern different from that of the sensor velocity data. As a result, it is noted that GPS data reception is not good at a corresponding point and it is difficult to rely on GPS velocity data received at the corresponding point. Also, it is noted that the movement data filtered with reference to the method of FIG. 25 have a graph almost similar to that of the sensor velocity data not the GPS velocity data due to the weight concentrated on Velocity-sensor.

Based on the sensor velocity data of FIG. 30b, the user who wears smart shoes maintains a walking operation at a certain velocity in the same manner as FIG. 29. However, referring the GPS velocity data, an upper and lower fluctuation range is very great and frequent based on the sensor velocity data as a horizontal axis. In other words, it is difficult to rely on the GPS velocity data in FIG. 30b. Particularly, at a point 3010 of FIG. 30a, the user increases a velocity a little more than before. In this case, referring to the graph of FIG. 30b, it is noted that the GPS velocity data reach a maximum value at a point 3020 but the sensor velocity has little change and becomes a little fast at an end of the corresponding point 3010. Therefore, if the method of FIG. 25 according to the present invention is used, the weight values of the GPS velocity data and the sensor velocity data are different from those in FIG. 29, and this difference may be inferred from filtered velocity data 3030 at the corresponding point 3020 of FIG. 30b. In this case, it is noted that the user who wears the smart shoes has moved at a velocity different from a previous velocity at the point 3010 of FIG. 30a based on the sensor velocity data and the filtered velocity data although the GPS velocity data have a rapid fluctuation range.

Referring to FIG. 31b, if the GPS velocity data are remarkably different from the sensor velocity data, it may affect velocity data filtering through the weight at a minimum range referring to FIG. 25. However, it is noted that although the difference between the sensor velocity data and the GPS velocity data at the first point 3110 and the second point 3120 of FIG. 31b is greater than that at previous points, the GPS velocity data are maintained at the corresponding points at a certain range for a random timing point. In this way, if the GPS velocity is maintained continuously without one-time or instantaneous jumping even though there is a difference between the GPS velocity data and the sensor velocity data, a value different from the weight value calculated in FIG. 25 is given unlike the aforementioned description. That is, the weight value of the GPS velocity data is more reflected than the previous embodiment or graph. Therefore, referring to FIGS. 31a and 31b, the filtered velocity data at the first point 3110, 3140 and the second point 3120, 3130 may be close to the GPS velocity data by departing from the graph of the sensor velocity data.

Referring to FIG. 32b, the graph may be categorized into three intervals, a first interval 3210, a second interval 3220, and a third interval 3230. At this time, the first interval 3210 and the second interval 3230 correspond to the case that the user who wears the smart shoes move at a certain velocity, and the second interval 3220 corresponds to the case that the user stops moving or takes a rest.

In this case, referring to FIG. 32b, there are a small amount of accumulated data in the first interval, and it is noted that the GPS velocity data are not jumped instantaneously even though there is a difference between the GPS velocity data and the sensor velocity data. Therefore, it is noted that the filtered velocity data of FIG. 32b are not matched with the sensor velocity data and reflects the GPS velocity data.

Meanwhile, in case of the second interval 3220, based on the sensor velocity data, it is regarded that the user who wears the smart shoes stops moving. However, the GPS velocity data continue to have certain velocity data. In this case, if the method of FIG. 25 is used, since the weight value of the GPS velocity becomes zero, the filtered velocity data are displayed as zero, that is, stopped, in the same manner as the sensor velocity data in spite of the GPS velocity data having a predetermined value.

Also, the third interval 3230 is similar to the first interval 3240. Since reset is performed at the second interval 3220 due to zero-base, there are no accumulated data in the third interval 3230 in the same manner as the first interval 3210 unlike the normal case, and the GPS velocity data may be reflected in the filtered velocity data if the GPS velocity data do not correspond to one-time jumping 3250.

Referring to FIG. 33b, the GPS velocity data 3320 of the first point 3310 in FIG. 33a are jumped one time, but are alternately changed based on the sensor velocity data used as a horizontal axis at the other points or intervals. However, since the GPS velocity data are maintained at a certain range with the sensor velocity data, it affects the weight value of FIG. 25, whereas the GPS velocity data of the first point little affect the weight value of FIG. 25 unlike shown in the previous drawing.

Figure 34:
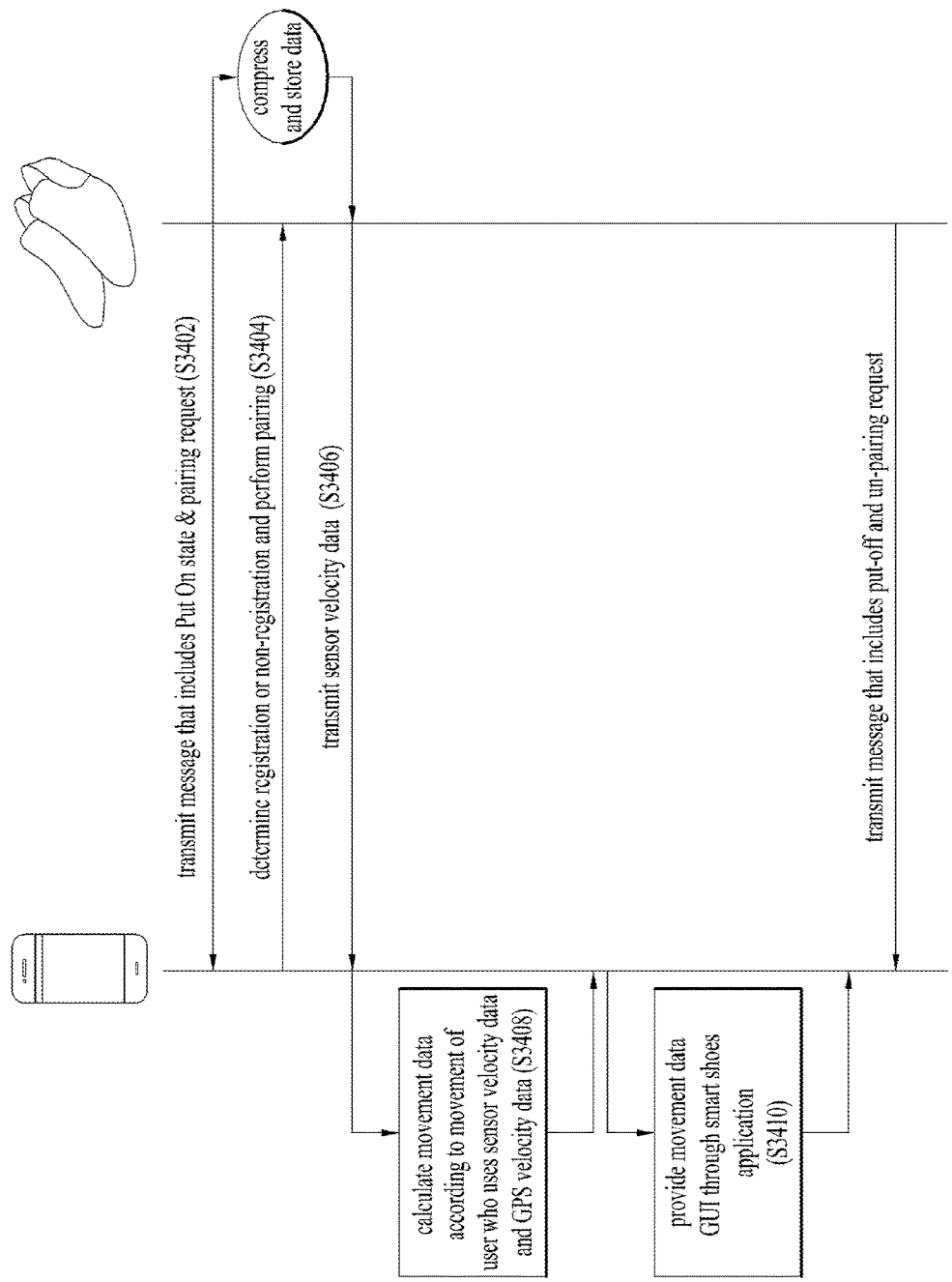
FIG. 34 is a flow chart illustrating a GPS velocity data filtering procedure according to one embodiment of the present invention.

FIG. 34 is a flow chart illustrating a GPS velocity data filtering procedure according to one embodiment of the present invention.

First of all, if the user wears the smart shoes provided with the pressure sensor, the smart shoes a message, which includes a foot-on state and pairing request, to the smart terminal through sensing of the pressure sensor (S3402).

If the above message is received, the smart terminal determines whether the corresponding smart shoes are registered therein, and as a result, grants or requests pairing if the smart shoes are the registered those (S3404). As a result of determination, if the smart shoes are not registered those, the smart terminal may perform the registration procedure of FIGS. 19 to 22 at this step.

If the smart shoes are paired with the smart terminal, the smart shoes collect the pressure sensor and transmit sensor velocity data compressed and stored in the memory to the smart terminal (3406).

If the sensor velocity data are received from the smart shoes, the smart terminal receives the GPS velocity data received through the GPS sensor and calculates movement data according to movement of the user who wears the smart shoes, based on the sensor velocity data and the GPS velocity data (S3408).

In this case, the filtering according to FIG. 25 may be performed during the calculating step.

If the smart shoes application is executed, the smart terminal configures a GUI based on the calculated movement data and provides the configured GUI (S3410). In this case, the smart terminal may perform the step S3408 after the smart shoes application is executed.

Although not shown, the user who wears the smart shoes may enter a place where GPS data are not received. In this case, if the user again enters a place where the GPS data are received, the GPS data may be received but have no correlation with the previously received GPS data or have a difference from the previously received GPS data. In the present invention, in this case, a path in case of missing or error reception of the GPS data may be calibrated appropriately using the PDR scheme that reflects data sensed through the pressure sensor of the smart shoes in FIG. 13. Meanwhile, in this case, in case of velocity calibration through filtering, since the sensor velocity data may be received through the pressure sensor even at a place where the GPS velocity data are not received, the sensor velocity data may be used for velocity calibration through filtering. At this time, the method of FIG. 25 may be applied as it is.

Also, although not shown, various nodes such as Wi-Fi and AP as well as the GPS data may be used in combination to perform path calibration and velocity calibration through filtering related to the present invention. For example, it is assumed that the user wears the smart shoes at home and walks to a walkway and then comes back home. Generally, the GPS data are not received at home. Therefore, another method different from the method of FIG. 25 should be used at home. For example, only data sensed through the pressure sensor of the smart shoes may be used at home, or may be calculated with data collected through AP or Wi-Fi at home, whereby path or velocity data may be calculated.

Hereinafter, data communication between the smart shoes and the smart terminal with respect to data collected by the smart shoes as well as the sensor velocity data sensed through the pressure sensor in the aforementioned smart shoes will be described in more detail.

This data communication between the smart terminals may be categorized into a case that there is no reference smart terminal or server and a case that there is a reference smart terminal or server.

The former case may mean data communication between the smart shoes.

In the latter case, the reference smart terminal may be a smart phone, a tablet PC, a laptop computer, a digital TV, a PC, etc. For convenience of description, in this specification, the smart phone will be described as an example of the reference smart terminal. Meanwhile, the smart phone may download and install applications (for example, smart shoes application) related to data processing of the smart shoes in accordance with the present invention.

Meanwhile, data communication between the smart terminals in this specification may be performed based on various wire/wireless communication protocols such as BT (Bluetooth), BLE (Bluetooth Low Energy), Zigbee, Wi-Fi, and Wi-Fi direct. For understanding of the present invention and convenience of description, a BLE communication protocol will be described exemplarily considering the smart terminals, especially a low power of the smart shoes.

Figure 35:
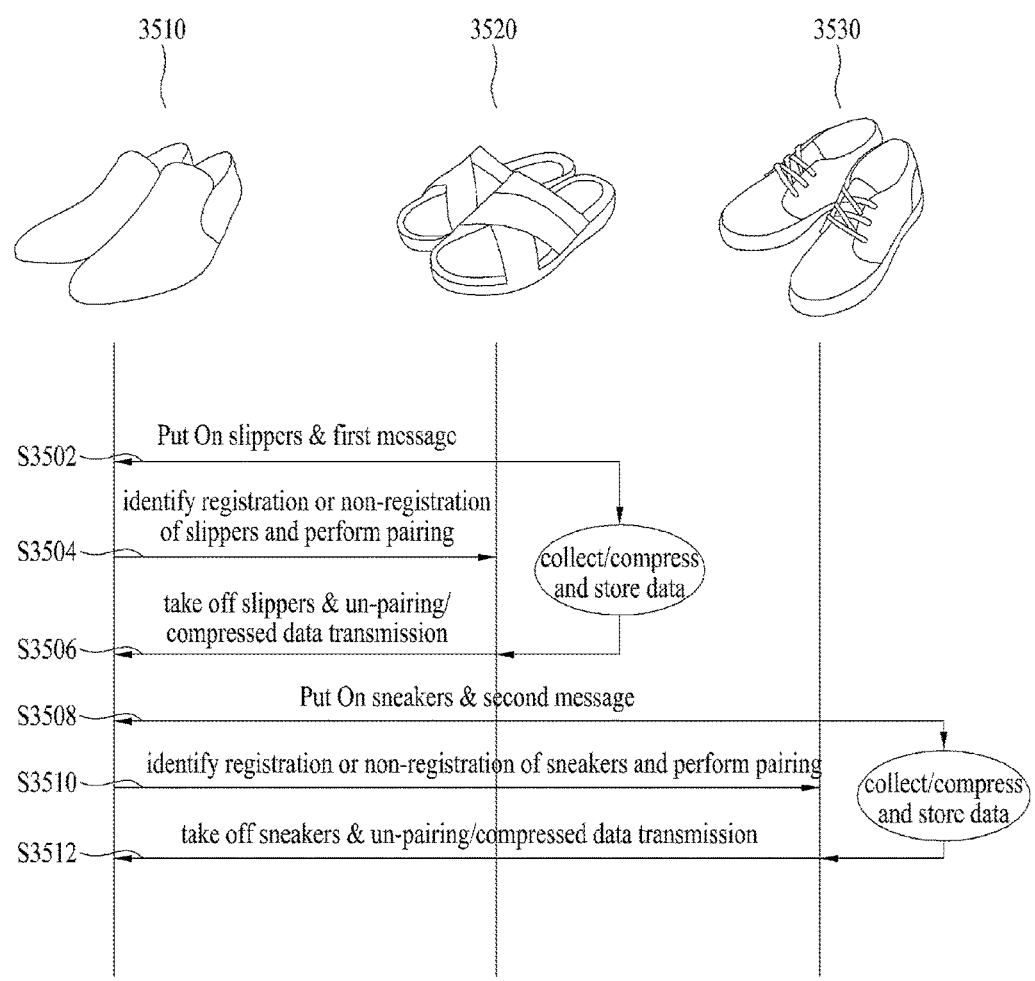
FIGS. 35 and 36 are views illustrating a data communication procedure between smart shoes in accordance with one embodiment of the present invention.
Figure 36:
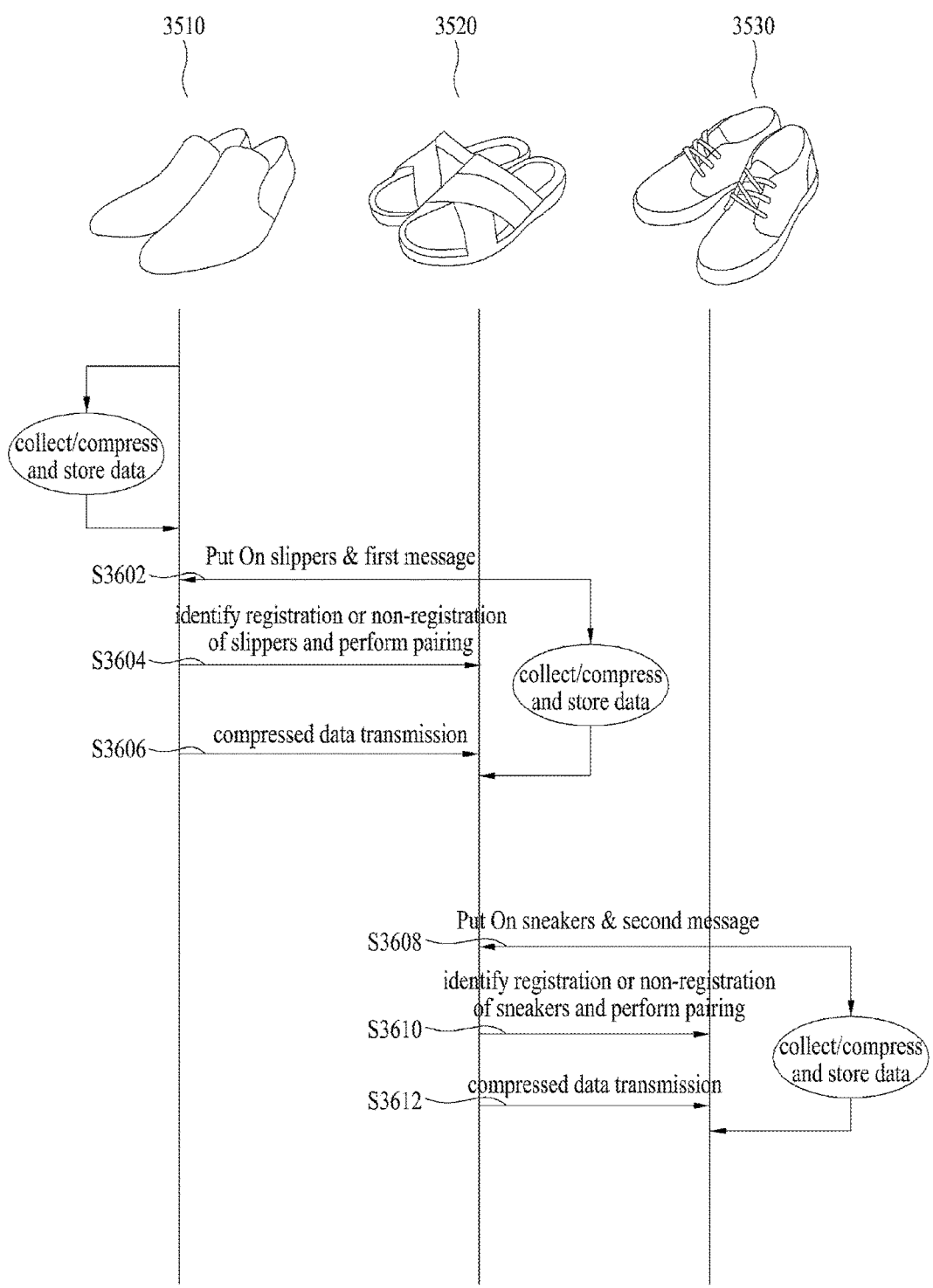

FIGS. 35 and 36 are views illustrating a data communication procedure between smart shoes in accordance with one embodiment of the present invention.

Data communication between the smart shoes may be performed by a contact/non-contact mode between the smart shoes. The contact mode means that smart shoes are in contact with another smart shoes. Also, the non-contact mode means that data are automatically transmitted and received between one smart shoe and another smart shoe as the user who wears the smart shoes performs in/out for a specific event or specific position, such as a gesture, button, voice, grip, and weight.

A scenario of data communication will be described briefly with reference to FIG. 35. For convenience of description, three pair of shoes of the user will be described exemplarily in FIGS. 35 and 36.

Referring to FIGS. 35 and 36, there are first smart shoes 3510, second smart shoes (slippers) 3520 and third smart shoes (sneakers) 3530, and it is assumed that the first to third smart shoes are those of the same user and the first smart shoes 3510 are reference smart shoes. The reference smart shoes may mean those that serve as a reference during data communication with another smart shoes or receive data of another smart shoes. Alternatively, the reference smart shoes may be those having memory capacity relatively greater than that of the other smart shoes.

Hereinafter, in this specification, 'put-on' means that movement data sensed by the pressure sensor provided in the smart shoes are collected in accordance with movement of the user who wears the smart shoes, and 'take-off' means a case opposite to the case of 'put-on'. In other words, 'take-off' means that movement data are not collected from the smart shoes any more as the user who wears the smart shoes has no movement or takes off the corresponding smart shoes.

First of all, the scenario of FIG. 35 will be described.

If the second smart shoes 3520 are put-on, the second smart shoes 3520 transmit a first message, which includes a request of at least one of put-on and pairing, to the first smart shoes 3510 (S3502). In this case, messages transmitted and received between the smart terminals may depend on the definition in a specific communication protocol. For example, the messages may be advertisement messages used by the BLE protocol. If the first message is received from the second smart shoes 3520, the first smart shoes 3510 parse or decode the first message and perform pairing with the second smart shoes 3520 (S3504). After put-on, the second smart shoes 3520 compress and store data collected through the sensors including the pressure sensor. Afterwards, the second smart shoes 3520 may request the first smart shoes 3510 of its take-off and un-pairing (S3506). At this time, the second smart shoes 3520 may transfer the compressed and stored data to the first smart shoes 3510 (or server) simultaneously with or prior to the step S3506, that is, un-pairing. In this case, the step S3506 may be performed in the form of the aforementioned message.

If the third smart shoes 3530 are put-on, the same procedure as data communication between the first smart shoes 3510 and the second smart shoes 3520 may be performed.

For example, if the third smart shoes 3530 are put-on, the third smart shoes 3530 transmit a second message, which includes a request of at least one of put-on and pairing, to the first smart shoes 3510 (S3508). If the second message is received from the second smart shoes 3530, the first smart shoes 3510 parse or decode the second message and perform pairing with the third smart shoes 3530 (S3510). Afterwards, the third smart shoes 3530 may request the first smart shoes 3510 of its take-off and un-pairing (S3512). Likewise, the third smart shoes 3530 may transfer the compressed and stored data to the first smart shoes 3510 (or server) simultaneously with or prior to the step S3512, that is, un-pairing. In this case, the step S3512 may be performed in the form of the aforementioned message.

Meanwhile, if the message is received from the second smart shoes 3520 or/and the third smart shoes 3530, the first smart shoes 3510 may perform registration and authentication of the corresponding smart shoes. In this case, if the corresponding smart shoes that have transmitted the message have not registered in the first smart shoes 3510 or have registered in the first smart shoes 3510 but its authentication is failed, the procedure of FIGS. 19 to 22 may be performed. However, the procedure of FIGS. 19 to 22 may not be performed and end without pairing if the corresponding smart shoes are failed in registration or authentication.

In FIG. 35, the third smart shoes 3530 transmit a message to the first smart shoes 3510 which are the reference smart shoes. However, if the smart shoes previously put on the user are the second smart shoes 3520, the third smart shoes 3530 may transmit the message to the second smart shoes 3520 not the first smart shoes 3510.

Meanwhile, in FIG. 35, pairing between the smart shoes may be for data transmission and reception between the smart terminals. Therefore, as described later, if there is a reference smart terminal not the smart shoes, message transmission and reception or pairing/un-pairing may not be performed in spite of the presence of the smart shoes.

The data communication procedure between the smart shoes in FIG. 36 is almost identical to the data communication procedure between the smart shoes in FIG. 35. However, the first smart shoes 3510 of FIG. 35 always serve as a reference terminal among the other smart shoes and receive compressed data, whereas smart shoes currently put on the user serve as a reference terminal in FIG. 36. Hereinafter, repeated steps of those of FIG. 35 will be omitted or briefly described in FIG. 36 and step(s) different from those of FIG. 35 will be described.

The first smart shoes 3510 stores data sensed and collected through the pressure sensor provided the smart shoes in accordance with movement of the user in the memory. At this time, movement data disclosed in this specification may be stored in the memory as raw data, or the raw data may be compressed or doubly compressed and then stored in the memory.

Steps S3602 to S3606 in FIG. 36 are almost identical to the steps S3502 to S3506 of FIG. 35. However, the second smart shoes 3520 may directly transmit a first message on its put-on and pairing request to the first smart shoes 3510 which are previously put-on, at step S3602, or may be batch broadcasted. In case of direct transmission, the second smart shoes 3520 should know that the previous put-on smart shoes are the first smart shoes 3510. In this respect, the first smart shoes 3510 may broadcast its take-off during take-off. Meanwhile, unlike FIG. 35, the second smart shoes 3520 may not notify the first smart shoes 3510 which are previously put-on, of its take-off in FIG. 36. As described above, since the smart shoes currently put-on serve as the reference smart terminal in FIG. 36, the second smart shoes 3520 may receive previously stored movement data from the first smart shoes 3510 in accordance with transmission of the first message (S3606). The second smart shoes 3520 may store movement data in the memory periodically/non-periodically after put-on. At this time, the second smart shoes 3520 may compress and store the movement data in the memory together with or separately from the compressed data received from the first smart shoes 3510 at the step S3606.

In the same manner, steps S3608 to S3612 of the smart shoes 3530 are almost identical to the steps S3602 to S3606. However, since the third smart shoes 3530 are currently put-on at the steps S3608 to S3612, the third smart shoes 3530 serve as a reference smart terminal, and the compressed data received from the second smart shoes 3520 may include the movement data of the first smart shoes 3510.

Meanwhile, referring to FIGS. 35 and 36, registration or data transmission between the smarts shoes may be performed manually or automatically in accordance with various events such as a gesture, a button, a voice, a grip, a weight, an LBS (local based system) or in-out for a specific location.

Figure 37:
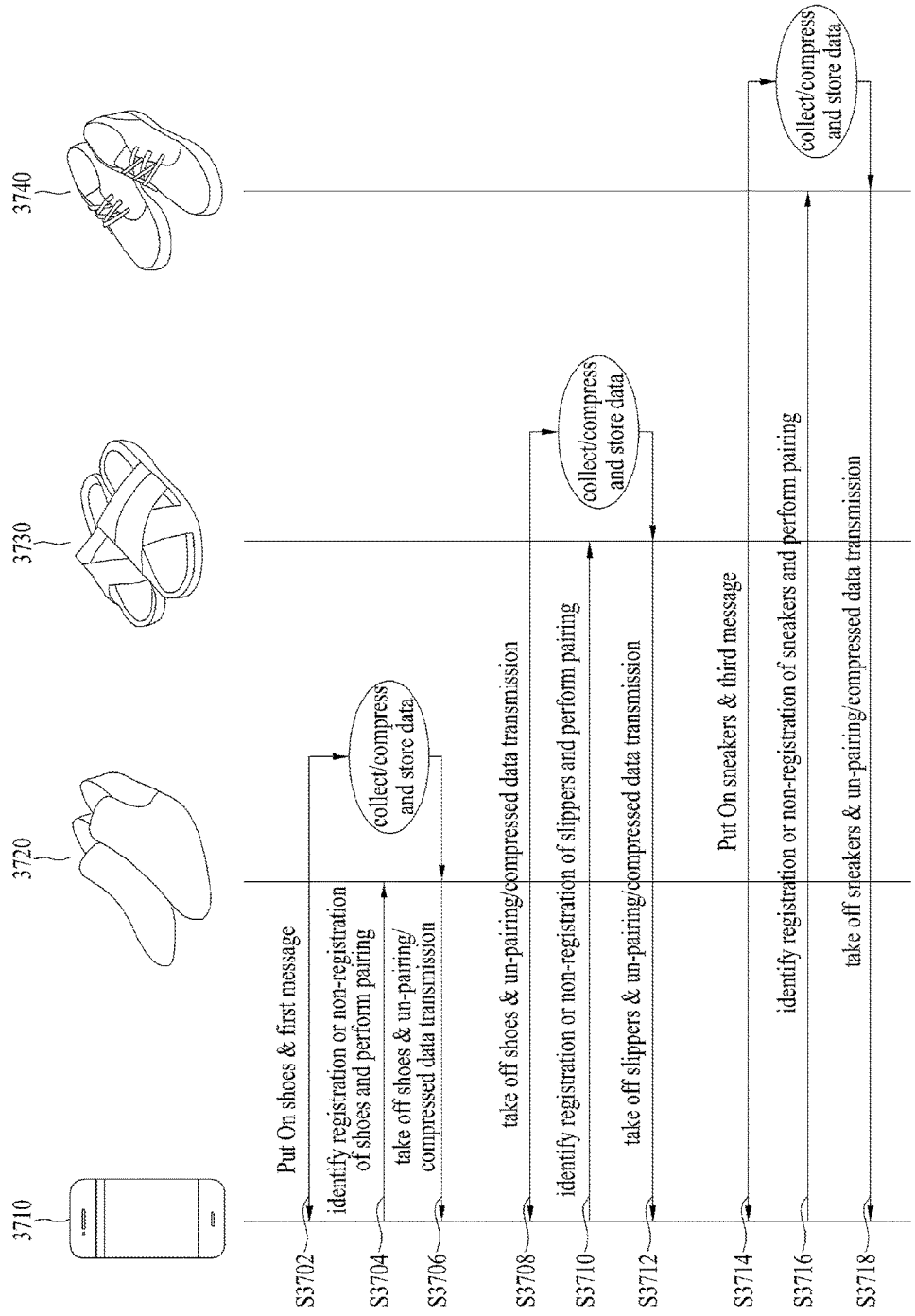
FIGS. 37 and 38 are views illustrating a data communication procedure between smart terminals in accordance with one embodiment of the present invention.
Figure 38:
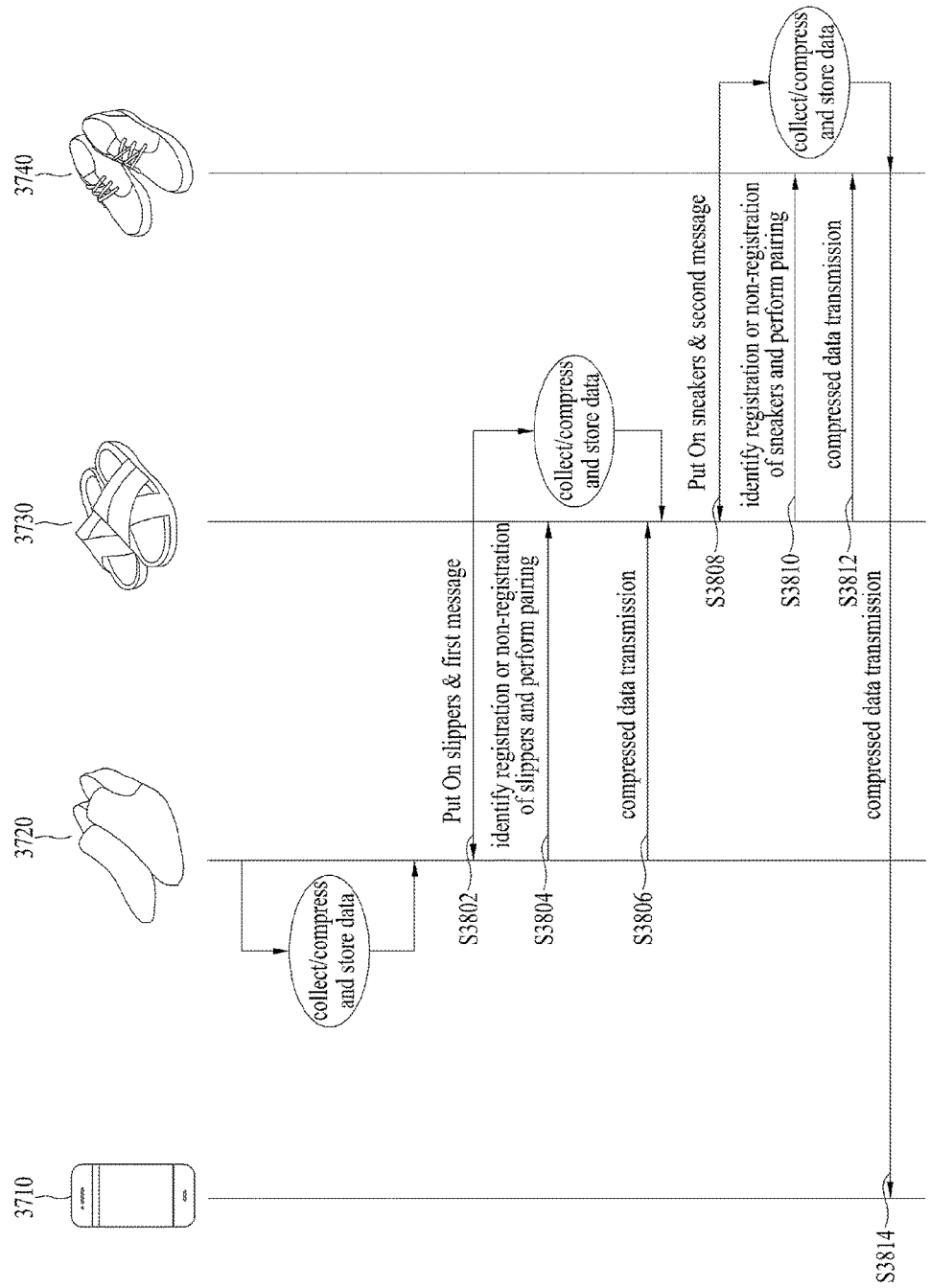

FIGS. 37 and 38 are views illustrating a data communication procedure between smart terminals in accordance with one embodiment of the present invention.

FIGS. 37 and 38 are views illustrating a method for data communication between smart shoes and a smart terminal, that is, a smart phone. In this case, the smart phone will be referred to as a reference smart terminal.

Referring to FIGS. 37 and 38, the smart terminal service system includes a reference smart terminal 3710, first smart shoes 3720, second smart shoes 3730, and third smart shoes 3740.

If a first message is received from the first smart shoes 3720, the reference smart terminal 3710 identifies registration or non-registration of the corresponding smart shoes and performs pairing with the corresponding smart shoes (S3704).

Afterwards, if the first smart shoes 3720 are taken-off, the first smart shoes 3720 notifies the reference smart terminal 3710 of their take-off, and requests un-pairing (S3706).

Meanwhile, the first smart shoes 3720 collect movement data simultaneously with put-on time or from second pressure sensing timing after initial pressure sensing until take-off and compress and store the collected movement data in the memory. For convenience, the movement data will be referred to as first data.

The first smart shoes 3720 may transmit the compressed and stored first data to the reference smart terminal 3710 simultaneously with or just before the take-off report and un-pairing timing.

The second smart shoes 3730 and the third smart shoes 3740 also perform the same procedure as the aforementioned data communication procedure between the first smart shoes 3720 and the reference smart terminal 3710.

In other words, if the second smart shoes 3730 are put-on, the second smart shoes 3730 transmit a second message to the reference smart terminal 3710 (S3708).

If the second message is received from the second smart shoes 3730, the reference smart terminal 3710 identifies registration or non-registration of the second smart shoes 3730 and then performs pairing with the second smart shoes 3730 (S3710).

The second smart shoes 3730 collect, compress and store their movement data in the same manner as the first smart shoes 3720. If the second smart shoes 3730 are taken-off, the second smart shoes 3730 report their take-off to the reference smart terminal 3710, and transmit previously stored movement data (second data) to the reference smart terminal 3710 together with an un-pairing request (S3712).

Also, if the third smart shoes 3740 are put-on, the third smart shoes 3740 transmit a third message to the reference smart terminal 3710 (S3714).

If the third message is received from the third smart shoes 3740, the reference smart terminal 3710 identifies registration or non-registration of the third smart shoes 3740 and then performs pairing with the third smart shoes 3740 (S3716).

The third smart shoes 3740 collect, compress and store their movement data in the same manner as the first smart shoes 3720 and the second smart shoes 3730. If the third smart shoes 3740 are taken-off, the third smart shoes 3740 report their take-off to the reference smart terminal 3710, and transmit previously stored movement data (third data) to the reference smart terminal 3710 together with an un-pairing request (S3718).

In FIG. 37, each smart shoes compress and store the movement data collected after put-on in the memory, and transmit movement data previously compressed and stored before un-pairing with the reference smart terminal to the reference smart terminal at their take-off timing.

Next, in FIG. 38, each smart shoes does not directly transmit compressed and stored movement data to the reference smart terminal like FIG. 37. That is, in FIG. 38, previously put-on smart shoes transmit their compressed and stored movement data to next put-on smart shoes and finally put-on smart shoes transmit the compressed and stored movement data received from the previous smart shoes and their movement data to the reference smart terminal 3710 at one time like FIG. 36. Meanwhile, if there are no put-on smart shoes within a predetermined time after the previously put-on smart shoes are taken off, the corresponding smart shoes may be determined as the finally put-on smart shoes. Alternatively, the finally put-on and/or taken-off smart shoes may be determined as the final smart shoes prior to a reference time based on a predetermined time, for example, 24 hours.

In this case, the steps S3802 to S3812 of FIG. 38 are identical to the steps S3602 to S3612 of FIG. 36. After the step S3812, if the corresponding smart shoes are determined as the final smart shoes, the corresponding smart shoes transmit the compressed and stored movement data to the reference smart terminal 3710 at a predetermined time (S3814). At this time, at least one or more movement data of the first smart shoes 3720 and the second smart shoes 3730 are further included in the movement data transmitted from the final smart shoes 3740, that is, the movement data of the third smart shoes 3740.

In FIGS. 37 and 38, data transmission may be performed simultaneously with or prior to un-pairing as the corresponding smart shoes are taken off as shown.

Meanwhile, in FIG. 37, each smart shoes do not transmit their stored movement data to the reference smart terminal simultaneously with or prior to their take-off and un-pairing, and if the reference smart terminal is taken off or a smart shoes application is inactive in the corresponding reference smart terminal at that time, the corresponding smart shoes may transmit their stored data to the server or next smart shoes as shown in FIG. 38 simultaneously with or prior to the un-pairing timing. Alternatively, in a state that the corresponding smart shoes store movement data, when the reference smart terminal is turned on, and the corresponding reference smart terminal executes the smart shoes application or the corresponding smart shoes again become the put-on state, the corresponding smart shoes may transmit the previously stored movement data to the reference smart terminal.

Figure 39:
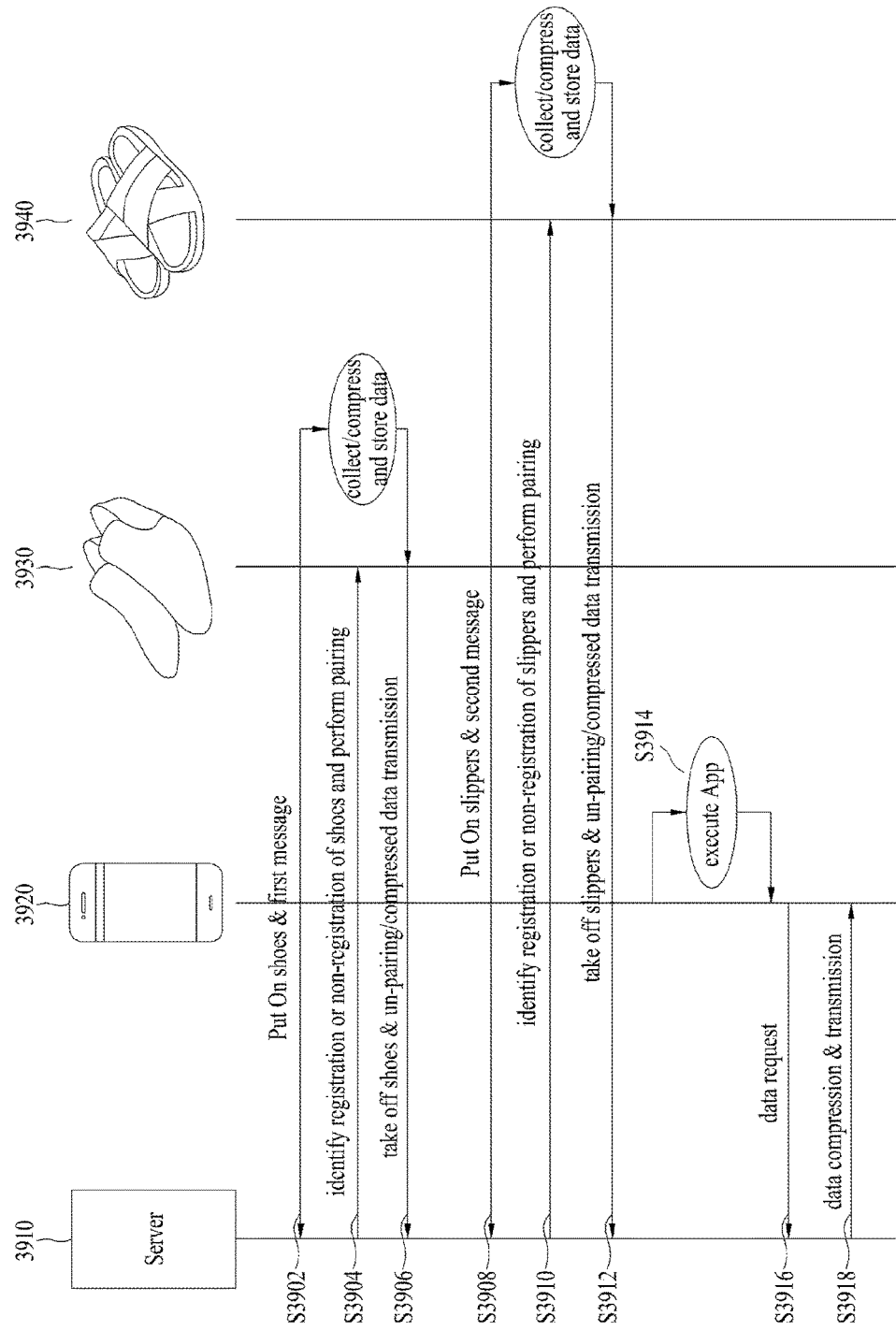
FIGS. 39 and 40 are views illustrating a data communication procedure between smart terminals in accordance with another embodiment of the present invention.
Figure 40:
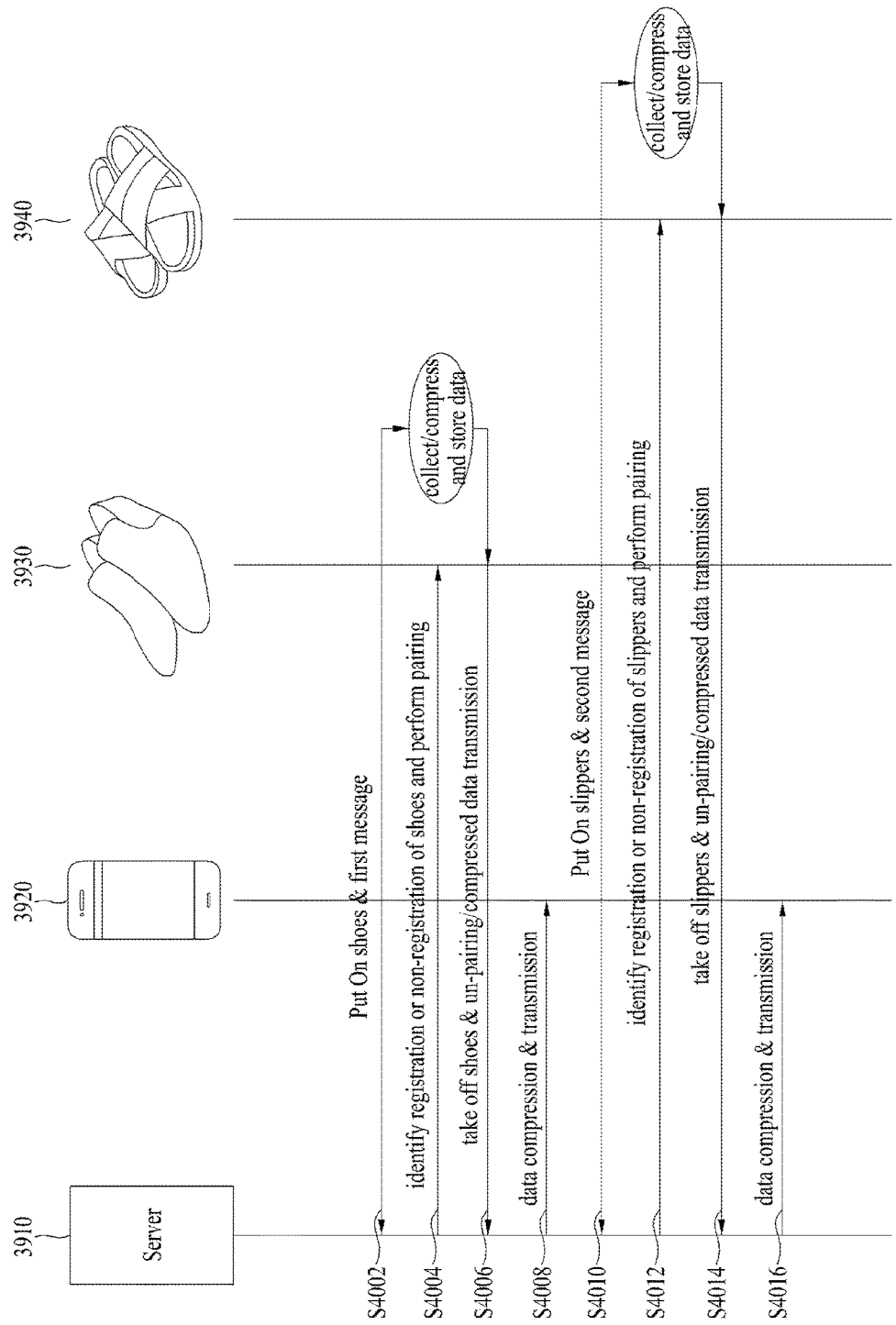

FIGS. 39 and 40 are views illustrating a data communication procedure between smart terminals in accordance with another embodiment of the present invention.

Referring to FIGS. 39 and 40, the smart terminal service system includes a server 3910, a smart phone 3920, and smart terminals 3930 and 3940. In this case, the server 3910 may correspond to the reference smart terminal in FIGS. 37 and 38. Meanwhile, the server 3910 includes a processor, which stores data and may perform communication, such as a cloud server.

Steps S3902 to S3912 in FIG. 39 are almost identical to the steps S3702 to S3712 of FIG. 37. However, instead of the smart phone (reference smart terminal) 3710 in FIG. 37, a server (reference smart terminal) 3910 may perform data communication with the smart shoes 3930 and 3940 in FIG. 39.

During or after data communication including movement between the server 3910 and the smart shoes 3930 and 3940, a smart shoes application is executed in the smart phone 3920 (S3914), and if the smart phone 3920 requests the server 3910 of data (S3916), the server 3910 transmits movement data of the smart shoes 3930 and 3940, which are previously received and compress-stored, to the smart phone 3920 (S3918).

Meanwhile, the server 3910 identifies registration or non-registration of the corresponding smart shoes which have transmitted a message, and performs a response to the identified result. At this time, the server 3910 may use the smart phone 3920 in respect of the registration. Meanwhile, the server 3910 may perform or control pairing with the first smart shoes 3930 directly or using at least one of the smart phone 3920, a relay (not shown), and other communication server.

In addition, the server 3910 may store data of the first smart shoes 3930 and the second smart shoes 3940 in a predetermined address through the steps S3902 to S3912 and then may be on standby. Afterwards, the if the reference smart terminal 3920 is turned on, the smart shoes application is executed in the reference smart terminal 3920 as shown (S3914) and then stored data of smart shoes are requested from the reference smart terminal 3920 (S3916), the server 3910 may transmit the stored data to the reference smart terminal 3920 (S3918).

In other words, in FIG. 39, the server 3910 transfers data stored at a predetermined time (for example, one time at nine o'clock p.m. in a day) or when there is a request of the reference smart terminal 3920 without transferring the data received from the smart shoes to the reference smart terminal 3920 every time.

The data transmission procedure between the server 3910 and the first smart shoes 3930/the second smart shoes 3940 in FIG. 40 is almost identical to that in FIG. 39. Since steps S4002 to S4006 and steps S4010 to S4014 in FIG. 40 respectively correspond to the steps S3902 to S3906 and the steps S3908 to S3913 in FIG. 30, their detailed description will be omitted.

However, in FIG. 40, the server 3910 may receive data from the first smart shoes 3930 and store the received data in a specific address. Then, the server 3910 may transfer at least one of the stored specific address information and the stored data to the smart phone 3920 (S4008). This may equally be applied to step S4016 of the second smart shoes 3940.

In other words, in FIG. 40, whenever data are received from the smart shoes, the server 3910 may store the received data and then transfer the data to the reference smart terminal 3920, or may immediately transfer the data to the reference smart terminal 3920 without storing the data. Meanwhile, this may equally be applied to even a case that a plurality of messages are received from one smart shoes.

In FIG. 40, if data are received as above, the reference smart terminal 3920 stores the data in the memory. Afterwards, if the smart shoes application is executed, the reference smart terminal 3920 may configure and provide a user interface (UI) as shown in FIG. 29 by reading out the data stored in the memory.

Meanwhile, although not shown, if each smart shoes which are put-on transmit a message to the server, the server may transfer the message to the smart phone, and the smart phone may determine registration and pairing of the corresponding smart shoes. Afterwards, the movement data of the smart shoes may be transferred to the smart phone directly or through the server. In other words, the server may receive the message of the smart shoes and receive and store the movement data, and the smart phone may process or determine registration and pairing of the smart shoes according to reception of the message. Alternatively, each smart shoes which are put-on may directly transmit and receive the message to and from the smart phone and performs identification of registration and pairing as shown in FIGS. 37 and 38. However, only the movement data may be uploaded to the server and then may be downloaded by a request of the smart phone or execution of the smart shoes application installed in the smart phone.

The smart terminals (including the reference smart terminal) transmit and receive data to and from each other through BLE communication protocol, and the server 3910 may use another communication mode. For example, the server 3910 stores the data received from the smart terminals in a specific address, and may transfer only xml (extensible markup language) address corresponding to the specific address to the reference smart terminal 3920 and may not transmit actual data. Therefore, the reference smart terminal 3920 may download and use the actual smart shoes data by accessing the transferred xml address.

Meanwhile, although not shown, data communication between the aforementioned smart terminals may be performed by combination of at least two or more of the methods shown in FIGS. 35 to 40.

Although two or three smart shoes of the smart terminals are illustrated in FIGS. 35 to 40, the present invention may be applied to smart shoes more than two or three equally or similarly without limitation to the examples of FIGS. 35 to 40. Also, although one server and one smart phone are illustrated as above, a plurality of servers and a plurality of smart phones may be provided. The aforementioned procedures may equally or similarly be applied to even a case that other smart terminals as well as the above smart shoes are associated together.

Figure 41:
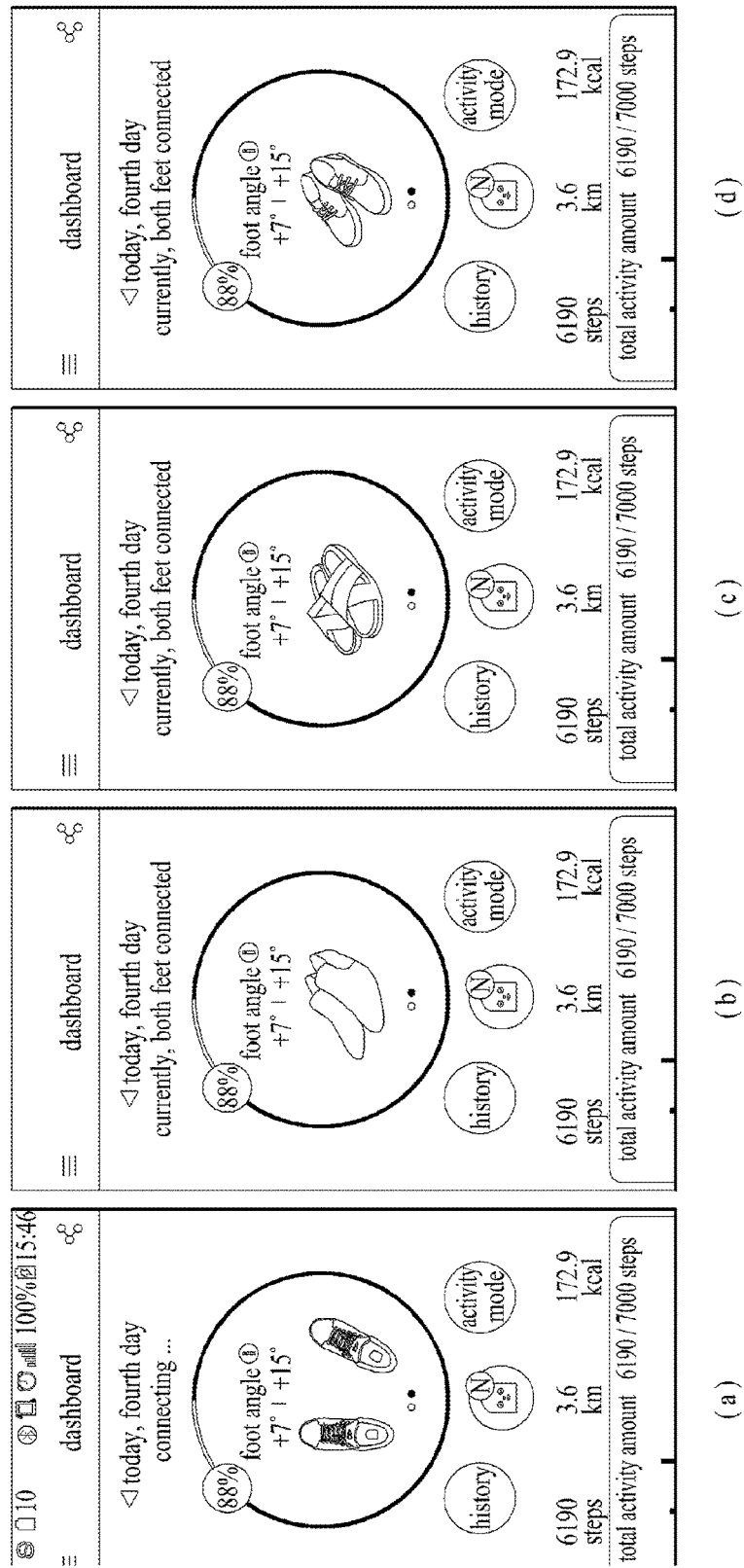
FIG. 41 is a view illustrating one example of a user interface provided by a smart terminal on the basis of smart shoes data in accordance with one embodiment of the present invention.

FIG. 41 is a view illustrating one example of a user interface provided by a smart terminal based on smart shoes data in accordance with one embodiment of the present invention.

FIG. 41 illustrates user interfaces configured based on data collected by at least one of FIGS. 35 to 40 through smart shoes if a smart shoes application is executed in a reference smart terminal.

FIG. 41a illustrates a screen on which a smart shoes application is executed in the reference smart terminal, that is, a user interface screen of the smart shoes application, which corresponds to a screen prior to connection of the smart shoes.

Meanwhile, FIG. 41b illustrates a user interface in a state that the first smart shoes are paired, FIG. 41c illustrates a user interface in a state that the second smart shoes are paired, and FIG. 41d illustrates a user interface in a state that the third smart shoes are paired. As described above, the second smart shoes are paired in FIG. 41c. In this case, data provided by the user interface may be provided based on movement data collected by the second smart shoes which are paired, or may be data including movement data collected by the first smart shoes which are previously paired. FIG. 41d may be identical to FIG. 41c.

Meanwhile, although not shown, only an icon indicating currently paired smart shoes is displayed on the screen in FIGS. 41b to 41d, whereas the icon indicating currently paired smart shoes may be provided together with icons indicating previously paired smart shoes in FIG. 41c or 41d. Therefore, that smart shoes put-on at a corresponding date may be identified in FIG. 41c or 41d at one time. At this time, previously put-on smart shoes except smart shoes currently worn by the user and paired are inactive and may be provided to identify smart shoes currently worn by the user. As a result, if another smart shoes not the smart shoes currently worn by the user are inactive, the user may intuitively identify such an error and immediately process an error of data. Also, the reference smart terminal may immediately identify movement data acquired through previously put-on smart shoes by accessing FIG. 41b or 41c in response to a left and right swipe type user input even in the case that the screen of FIG. 41d is currently provided through the smart shoes terminal.

Figure 42:
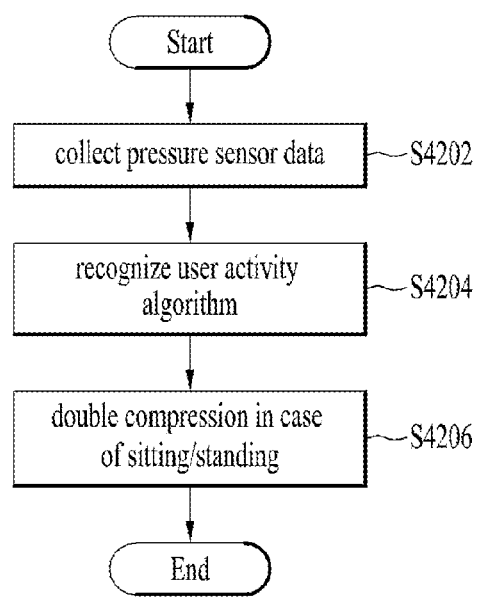
FIG. 42 is a flow chart illustrating a data communication procedure between smart terminals according to one embodiment of the present invention.

FIG. 42 is a flow chart illustrating an algorithm for collecting data from smart shoes according to one embodiment of the present invention and storing the collected data.

Referring to FIG. 42, the smart shoes collect movement data through the pressure sensor (S4202), and identify movement of the user from the collected movement data. At this time, the algorithm described in FIG. 13 may be used (S4204).

Afterwards, the smart shoes store the collected and identified movement data (S4206). At this time, the smart shoes store the movement data by compressing the movement data.

In this specification, data communication performed in a wireless environment (for example, BLE communication protocol) between smart terminals has been described as one embodiment. The BLE communication is particularly favorable for low power. However, since this BLE communication mode such as BLE beacon and BLE speaker has a bandwidth (BW) of 1/100 less than a normal BT, the time required for data transmission and reception may be longer. This may increase a consumed current, whereby power consumption may be increased. Therefore, this specification is intended to minimize restriction according to the bandwidth (BW) by compressing or doubly compressing the data collected from the smart shoes when the data are stored in the memory. In this case, the known compression technique may be used for the compression or double compression. Meanwhile, since the movement data collected through the smart shoes are binary data, compression efficiency is very good. For example, non-compressed raw data of the related art may be compressed as much as 98%. Preferably, the compression or double compression is a non-loss compression or double compression mode. Through the compression or double compression, in the case that data are not synchronized for a long time (for example, one month) or 10 seconds or more are required for transmission of raw data, the transmission time may be reduced remarkably to avoid hang process of an application and a transmission power having the greatest consumed current in a wireless environment may be minimized to contribute to a low power.

Meanwhile, in this specification, in case of data compression, all of raw data may not be compressed. In other words, if all of raw data are not compressed, a problem as to what data should be compressed may occur. The smart shoes may depend on various references with respect to a method how to sort data and a method how to extract meaningful data from the sorted data and compress the extracted data. In accordance with these references, data compression may be performed, and examples of these references may include positioning of the smart shoes at a specific position, entrance or entrance release of the smart shoes to a specific area, occurrence of a specific event in the smart shoes, unstable network environment or data transmission speed of a predetermined value or less, data amount of a predetermined value or more, battery residual of the smart shoes of a predetermined value or less, and other time zone (compression in the day time only, and raw data are used in the evening time). Also, corresponding data may be compressed by identification of a state change of the smart shoes wearer, such as sitting, standing, walking and running.

Meanwhile, data may be compressed or doubly compressed and stored prior to smart shoes battery discharge, and may be transmitted to the reference smart terminal or server. However, at this time, data which are not transmitted may be stored in a flash memory instead of the memory of the smart shoes, whereby there is no data loss even if data transmission is failed.

Meanwhile, the case that one of a plurality of smart shoes is turned on has been mainly described within this specification. However, the present invention is not limited to this case. In other words, at least two or more smart shoes may be turned on simultaneously for a predetermined time. In this case, the smart shoes may be processed in accordance with the procedures described through this specification. In addition, the left (L) smart shoe and the right (R) smart shoe, which constitute the smart shoes, have been described without separate classification, and may be processed using the aforementioned method.

According to each or combination of the aforementioned various embodiments of the present invention, the movement data of activity of the user who wear the smart shoes may be calculated exactly. Particularly, even though there is an error of GPS data for external activity movement of the user who wears the smart shoes, sensing data may be filtered through the pressure sensor provided in the smart shoes, whereby the movement data may be calculated exactly even under various statuses. As the movement data of the user who wears the smart shoes are calculated and provided exactly, satisfaction of the user may be improved.

It will be apparent to those skilled in the art that the present invention may be embodied in other specific forms without departing from the spirit and essential characteristics of the invention. Thus, the above embodiments are to be considered in all respects as illustrative and not restrictive. The scope of the invention should be determined by reasonable interpretation of the appended claims and all change which comes within the equivalent scope of the invention are included in the scope of the invention.

What is claimed is:

1. A smart terminal for performing data communication with smart shoes, the smart terminal comprising:
    a transceiver for transmitting and receiving a signal to and from the smart shoes;
    a receiver for receiving GPS (Global Positioning System) velocity data and sensor velocity data sensed by a pressure sensor provided in the smart shoes;
    a memory; and
    a controller for controlling an execution of a smart shoes application and calculating movement data of the smart shoes by filtering the received GPS velocity data and the sensor velocity data using weight values for velocity calibration,
    wherein the controller is further configured to control filtering to increase each of the weight values if an error between the received GPS velocity data and the sensor velocity data becomes smaller than a threshold, and to control adjusting a weight value factor related to the GPS velocity data among factors for the weight values in accordance with a status of the received GPS velocity data.

2. The smart terminal according to claim 1, further comprises an output unit, and wherein the controller configures GUI data related to at least one of a movement pattern, a path and a velocity of the smart shoes based on the movement data of the smart shoes, which are calculated by filtering, and controls the output unit to output the configured GUI data if the smart shoes application is executed.

3. The smart terminal according to claim 1, wherein the controller calculates movement data having no movement of the smart shoes regardless of the GPS velocity data if the sensor velocity data sensed by the pressure sensor provided in the smart shoes are zero,
    performs filtering using each of the weight values without removing a corresponding GPS velocity data value even in the case that the GPS velocity data value is jumped at a predetermined point or a GPS angle is changed, and
    calibrates a path by using a PDR (Pedestrian Dead Reckoning) scheme that considers the sensor velocity data and sensing data of the pressure sensor at an interval where the GPS velocity data are not received.

4. A smart terminal service system including smart shoes and a smart terminal, the smart terminal service system comprising:
    the smart shoes comprising:
    a memory;
    a pressure sensor sensed by an inputted pressure for a reference of the smart shoes; and
    a controller for calculating sensor velocity data on the basis of sensor data sensed by the pressure sensor and transmitting the calculated sensor velocity data to the smart terminal, and
    the smart terminal comprising:
    a transceiver for transmitting and receiving a signal to and from the smart shoes;
    a receiver for receiving GPS (Global Positioning System) velocity data and sensor velocity data sensed by a pressure sensor provided in the smart shoes;
    a memory; and
    a controller for controlling execution of a smart shoes application and calculating movement data of the smart shoes by filtering the received GPS data and the sensor velocity data using weight values for velocity calibration,
    wherein the controller is further configured to control filtering to increase each of the weight values if an error between the received GPS velocity data and the sensor velocity data becomes smaller than a threshold, and to control adjusting a weight value factor related to the GPS velocity data among factors for the weight values in accordance with a status of the received GPS velocity data.

5. The smart terminal service system according to claim 4, wherein the smart terminal further comprises an output unit, and wherein the controller of the smart terminal configures GUI data related to at least one of a movement pattern, a path and a velocity of the smart shoes based on the movement data of the smart shoes, which are calculated by filtering, and controls the output unit to output the configured GUI data if the smart shoes application is executed, or wherein the controller of the smart terminal calculates movement data having no movement of the smart shoes regardless of the GPS velocity data if the sensor velocity data sensed by the pressure sensor provided in the smart shoes are zero, performs filtering using each of the weight values without removing a corresponding GPS velocity data value even in the case that the GPS velocity data value is jumped at a predetermined point or a GPS angle is changed, and calibrates a path by using a PDR scheme that considers the sensor velocity data and sensing data of the pressure sensor at an interval where the GPS velocity data are not received.

6. A method of performing data in a smart terminal communicated with smart shoes, the method comprising:
    transmitting and receiving a signal to and from the smart shoes;
    receiving GPS (Global Positioning System) velocity data and sensor velocity data sensed by a pressure sensor included in the smart shoes;
    executing a smart shoes application; and
    calculating movement data of the smart shoes by filtering the received GPS velocity data and the sensor velocity data using weight values for velocity calibration,
    wherein the filtering is to increase each of the weight values if an error between the received GPS velocity data and the sensor velocity data becomes smaller than a threshold, and wherein a weight value factor related to the GPS velocity data among factors for the weight values is adjusted in accordance with a status of the received GPS velocity data.

7. The method of claim 6, further comprising:
    outputting the calculated movement data of the smart shoes;
    configuring GUI data related to at least one of a movement pattern, a path and a velocity of the smart shoes based on the movement data of the smart shoes, which are calculated by filtering; and
    outputting the configured GUI data if the smart shoes application is executed.

8. The method of claim 6, further comprising:
    calculating movement data having no movement of the smart shoes regardless of the GPS velocity data if the sensor velocity data sensed by the pressure sensor included in the smart shoes are zero;
    performing to filter using each of the weight values without removing a corresponding GPS velocity data value even in the case that the GPS velocity data value is jumped at a predetermined point or a GPS angle is changed; and calibrating a path by using a PDR (Pedestrian Dead Reckoning) scheme that considers the sensor velocity data and sensing data of the pressure sensor at an interval where the GPS velocity data are not received.

9. A method of processing data in a smart terminal service system including smart shoes and a smart terminal, the method comprising:

sensing an inputted pressure for a reference of the smart shoes;

calculating sensor velocity data based on the sensed predetermined pressure of the smart shoes;

transmitting the calculated sensor velocity data to the smart terminal;

transmitting and receiving a signal to and from the smart shoes;

receiving GPS (Global Positioning System) velocity data and sensor velocity data sensed by a pressure sensor included in the smart shoes;

executing a smart shoes application; and calculating movement data of the smart shoes by filtering the received GPS velocity data and the sensor velocity data using weight values for velocity calibration, wherein the filtering is to increase each of the weight values if an error between the received GPS velocity data and the sensor velocity data becomes smaller than a threshold, and wherein a weight value factor related to the GPS velocity data among factors for the weight values is adjusted in accordance with a status of the received GPS velocity data.

10. The method of claim 9, further comprising:

outputting the calculated movement data of the smart shoes;

configuring GUI data related to at least one of a movement pattern, a path and a velocity of the smart shoes based on the movement data of the smart shoes, which are calculated by filtering;

outputting the configured GUI data if the smart shoes application is executed, or calculating movement data having no movement of the smart shoes regardless of the GPS velocity data if the sensor velocity data sensed by the pressure sensor provided in the smart shoes are zero;

performing to filter using each of the weight values without removing a corresponding GPS velocity data value even in the case that the GPS velocity data value is jumped at a predetermined point or a GPS angle is changed; and calibrating a path by using a PDR scheme that considers the sensor velocity data and sensing data of the pressure sensor at an interval where the GPS velocity data are not received.

* * * * *